US012582604B2

(12) United States Patent
Zhang et al.

(10) Patent No.: US 12,582,604 B2
(45) Date of Patent: Mar. 24, 2026

(54) STABLE SOLID DISPERSION OF A B-RAF KINASE DIMER INHIBITOR, METHODS OF PREPARATION, AND USES THEREFOR

(71) Applicant: BEIGENE, LTD., Grand Cayman (KY)

(72) Inventors: Guoliang Zhang, Beijing (CN); Changyou Zhou, Princeton, NJ (US); Huangbin Sun, Beijing (CN)

(73) Assignee: BeiGene, Ltd., Grand Cayman (KY)

( * ) Notice: Subject to any disclaimer, the term of this patent is extended or adjusted under 35 U.S.C. 154(b) by 641 days.

(21) Appl. No.: 17/423,600

(22) PCT Filed: Jan. 23, 2020

(86) PCT No.: PCT/CN2020/073944

§ 371 (c)(1),
(2) Date: Jul. 16, 2021

(87) PCT Pub. No.: WO2020/151756

PCT Pub. Date: Jul. 30, 2020

(65) Prior Publication Data

US 2022/0105033 A1 Apr. 7, 2022

(30) Foreign Application Priority Data

Jan. 25, 2019 (WO) ................ PCT/CN2019/073254
Jul. 9, 2019 (WO) ................ PCT/CN2019/095227

(51) Int. Cl.
*A61K 9/14* (2006.01)
*A61K 31/4375* (2006.01)
(Continued)

(52) U.S. Cl.
CPC .......... *A61K 9/146* (2013.01); *A61K 31/4375* (2013.01); *A61K 47/38* (2013.01); *C07B 2200/13* (2013.01); *C07D 471/04* (2013.01)

(58) Field of Classification Search
CPC .... A61K 9/146; A61K 31/4375; A61K 47/38; A61K 9/0095; A61K 9/20; A61K 9/48;
(Continued)

(56) References Cited

U.S. PATENT DOCUMENTS 6,350,786 B1 2/2002 Albano et al.
6,548,555 B1 4/2003 Curatolo et al.
(Continued)

FOREIGN PATENT DOCUMENTS

CN 102361870 2/2012
CN 104936589 9/2015
(Continued)

OTHER PUBLICATIONS

Hannan, Enda J et al. "The significance of BRAF V600E mutation status discordance between primary cutaneous melanoma and brain metastases: The implications for BRAF inhibitor therapy." Medicine vol. 96,48 (2017): e8404. doi:10.1097/MD.0000000000008404 (Year: 2017).*

(Continued)

*Primary Examiner* — Marianne C Seidel
*Assistant Examiner* — Joshua A Atkinson
(74) *Attorney, Agent, or Firm* — Foley & Lardner LLP

(57) ABSTRACT

Disclosed herein is a physically stable solid dispersion comprising Compound 1, i.e., the B-RAF kinase dimer inhibitor 1-((1S, 1aS, 6bS)-5-((7-oxo-5, 6, 7, 8-tetrahydro-1, 8-naphthyridin-4-yl)oxy)-1a,6b-dihydro-1H-cyclopropa [b] benzofuran-1-yl)-3-(2, 4, 5-trifluorophenyl) urea and a specific stabilizing polymer, the method for preparing the same, and the uses of the solid dispersion. Also disclosed herein is the crystalline form of Compound 1.

4 Claims, 25 Drawing Sheets

(51) Int. Cl.
*A61K 47/38* (2006.01)
*C07D 471/04* (2006.01)

(58) Field of Classification Search
CPC ...... A61K 9/14; A61K 31/4427; A61K 47/61; C07B 2200/13; C07D 471/04; C07D 405/14; A61P 35/00
See application file for complete search history.

(56) References Cited

U.S. PATENT DOCUMENTS

| | | | | | |
|---|---|---|---|---|---|
| 9,670,203 | B2 | 6/2017 | Zhou et al. | | |
| 9,670,231 | B2 | 6/2017 | Zhou et al. | | |
| 9,920,055 | B2 * | 3/2018 | Zhou | A61P 35/00 | |
| 10,208,038 | B2 | 2/2019 | Zhou et al. | | |
| 10,562,899 | B2 | 2/2020 | Zhou et al. | | |
| 2008/0293787 | A1 | 11/2008 | Chatterji et al. | | |
| 2010/0197924 | A1 | 8/2010 | Gould et al. | | |
| 2010/0310659 | A1 * | 12/2010 | Desai | F01N 13/1888 | 546/113 |
| 2011/0118245 | A1 * | 5/2011 | Abraham | C07D 239/88 | 514/266.3 |
| 2014/0128373 | A1 * | 5/2014 | Ibrahim | A61P 35/00 | 544/122 |
| 2015/0265616 | A1 * | 9/2015 | Caponigro | A61P 43/00 | 514/266.4 |
| 2016/0159820 | A1 * | 6/2016 | Zhou | A61P 35/00 | 514/249 |
| 2016/0368914 | A1 * | 12/2016 | Zhou | A61P 1/16 | |
| 2017/0112799 | A1 * | 4/2017 | Srinivasan | A61K 9/146 | |
| 2017/0233391 | A1 * | 8/2017 | Zhou | A61K 31/496 | 514/230.5 |
| 2019/0144446 | A1 | 5/2019 | Zhou et al. | | |

FOREIGN PATENT DOCUMENTS

| | | | |
|---|---|---|---|
| CN | 105452223 | | 3/2016 |
| JP | 2004529112 | A | 9/2004 |
| JP | 2009519908 | A | 5/2009 |
| JP | 2009537524 | A | 10/2009 |
| JP | 2012522791 | A | 9/2012 |
| JP | 2014-189462 | A | 10/2014 |
| JP | 2016505029 | A | 2/2016 |
| JP | 2016523269 | A | 8/2016 |
| KR | 1020150097792 | | 8/2015 |
| KR | 1020160039187 | A | 4/2016 |
| WO | WO-02070516 | A2 | 9/2002 |
| WO | WO-2004021969 | A2 | 3/2004 |
| WO | WO-2005062795 | A2 | 7/2005 |
| WO | WO-2006066913 | A2 | 6/2006 |
| WO | WO-2007067444 | A1 | 6/2007 |
| WO | WO-2007136572 | A2 | 11/2007 |
| WO | WO-2008028617 | A1 | 3/2008 |
| WO | WO-2008079906 | A1 | 7/2008 |
| WO | WO-2008079909 | A1 | 7/2008 |
| WO | WO-2009012283 | A1 | 1/2009 |
| WO | WO-2010064722 | A1 | 6/2010 |
| WO | WO-2010114928 | A2 | 10/2010 |
| WO | WO-2011025947 | A1 | 3/2011 |
| WO | WO-2011092088 | A1 | 8/2011 |
| WO | WO-2011/115069 | A1 | 9/2011 |
| WO | WO-2013097224 | A1 | 7/2013 |
| WO | WO-2014114575 | A1 | 7/2014 |
| WO | WO-2014206343 | A1 | 12/2014 |
| WO | WO-2014206344 | A1 | 12/2014 |
| WO | WO-2020151756 | A1 | 7/2020 |

OTHER PUBLICATIONS

Ashland. "AquaSolveTM." AquaSolve Hydroxypropylmethylcellulose, Sep. 18, 2017, www.ashland.com/file_source/Ashland/Industries/Pharmaceutical/Links/PC-12624.6_AquaSolve_HPMCAS_Physical_Chemical_Properties.pdf. (Year: 2017).*

Ashland File Source Directory. Index of /File_source/Ashland/Industries/Pharmaceutical/Links, www.ashland.com/file_source/Ashland/Industries/Pharmaceutical/Links/. Accessed Apr. 26, 2024.), (Year: 2024).*

Tanno et al, "Evaluation of Hypromellose Acetate Succinate (HPMCAS) as a Carrier in Solid Dispersions", Drug Development and Industrial Pharmacy, 2004, vol. 30, No. 1, pp. 9-17 (Year: 2004).*

Shin-Etsu, Shin-Etsu Aqoat, pp. 1-19, retrieved 2025 from http://www.elementoorganika.ru/files/aqoat.pdf (Year: 2025).*

Iqbal et al, "FTIR Spectroscopic Study of Poly(Ethylene Glycol)-Nifedipine Dispersion Stability in Different Relative Humidities", Jour of Pharm Sciences, 2015, col. 104, issue 1, pp. 280-284 (Year: 2015).*

Pharma Excipients, Eudragit L 100-55, retrieved 2025 from https://www.pharmaexcipients.com/product/eudragit-l-100-55/ (Year: 2025).*

Zhao et al, "Solid dispersion in the development of a nimodipine delayed-release tablet formulation", Asian Jour Pharm Sci, 2013, vol. 9, issue 1, pp. 35-41 (Year: 2013).*

Brittain, Harry G. Polymorphism in Pharmaceutical Solids. Drugs and the Pharmaceutical Sciences, 192. 2009, 70 pages.

Sun Huan et al., "Synthesis of Lenvatinib", Journal of Chinese Pharmaceutical Industry, pp. 507-510, 2014.

Extended European Search Report in European Application No. 20744694.9, dated Oct. 7, 2022, 9 pages.

Carter, J. et al., "Non-p.V600E BRAF Mutations Are Common Using a More Sensitive and Broad Detection Tool," Am. J. Clin Pathol., Oct. 2015;144:620-628.

Extended European Search Report for European Application No. 14816633.3, mailed Nov. 7, 2016, 4 pages.

Extended European Search Report for European Application No. 14818636.4, mailed Jan. 10, 2017, 4 pages.

Gould, A. E. et al., "Design and Optimization of Potent and Orally Bioavailable Tetrahydronaphthalene Raf Inhibitors," Journal of Medicinal Chemistry, 54(6):1836-1846 (Mar. 2011).

International Search Report and Written Opinion for International Application No. PCT/CN2014/080983, mailed Oct. 9, 2014, 12 pages.

International Search Report and Written Opinion for International Application No. PCT/CN2014/080986, mailed Sep. 30, 2014, 11 pages.

International Search Report and Written Opinion for International Application No. PCT/CN2020/073944, mailed Apr. 22, 2020, 15 pages.

Serajuddin, A. T. M., "Solid dispersion of poorly water-soluble drugs: early promises, subsequent problems, and recent breakthroughs," J. Pharm. Sci. 88(10):1058-1066 (Oct. 1999).

Shah, N. et al., "Development of novel microprecipitated bulk powder (MBP) technology for manufacturing stable amorphous formulations of poorly soluble drugs," International Journal of Pharmaceuticals, 438(1-2):53-60 (Nov. 2012).

Wang, R. et al., "Application of hydroxypropyl methylcellulose acetate succinate to preparation of solid dispersions," Chinese Journal of Pharmaceuticals, vol. 47, No. 1, Dec. 2016, pp. 111-116 (with English abstract).

Wang et al., "Application of hypromellose acetate succinate in the preparation of solid dispersions", Chinese Journal of Pharmaceuticals, 47(1), 13 pages (2016).

Shah et al., "Improved Human Bioavailability of Vemurafenib, a Practically Insoluble Drug, Using an Amorphous Polymer-Stabilized Solid Dispersion Prepared by a Solvent-Controlled Coprecipitation Process", Journal of Pharmaceutical Sciences, vol. 102, No. 3, pp. 967-981 (Mar. 2013).

* cited by examiner

STABLE SOLID DISPERSION OF A B-RAF KINASE DIMER INHIBITOR, METHODS OF PREPARATION, AND USES THEREFOR

CROSS-REFERENCE TO RELATED APPLICATIONS

This application is a U.S. National Stage Application under 35 U.S.C. § 371 of International Application No. PCT/CN2020/073944, filed Jan. 23, 2020, which claims the benefit of International Patent Application Nos. PCT/CN2019/095227 (CN), filed on Jul. 9, 2019 and PCT/CN2019/073254 (CN), filed on Jan. 25, 2019, the disclosures of each of which is hereby incorporated by reference in its entirety for all purposes.

FIELD OF THE INVENTION

Disclosed herein is a physically stable solid dispersion comprising Compound 1, i.e., the B-RAF kinase dimer inhibitor 1-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(2,4,5-trifluorophenyl)urea and a specific stabilizing polymer, the method for preparing the same, and the uses of the solid dispersion. Also disclosed herein is a stable crystalline form of Compound 1, i.e., Form A, and a neat amorphous form of Compound 1, the methods of preparing the same. Also disclosed herein is a method of mass production of the B-RAF kinase dimer inhibitors disclosed herein.

BACKGROUND OF THE INVENTION 1-((1S,1aS,6b S)-5-((7-oxo-5,6,7,8-tetrahydro-1,8-naphthyridin-4-yl)oxy)-1a,6b-dihydro-1H-cyclopropa[b]benzofuran-1-yl)-3-(2,4,5-trifluorophenyl)urea (sometimes referred to as Compound 1 throughout the application) has been disclosed as a second generation of B-RAF inhibitor (See WO 2014/206343 A1). The structure of Compound 1 is shown below:

Compound 1

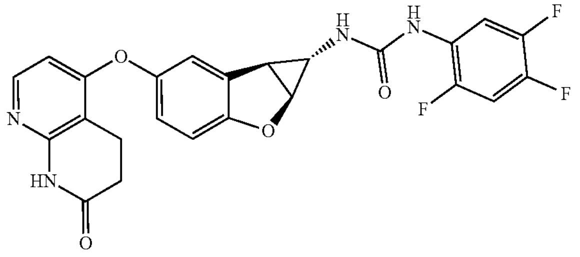

The B-RAF inhibitor of WO 2014/206343 A1 was prepared from the reaction of the 1a, 6b-dihydro-1H-cyclopropa[b]benzofuran-1-carbonyl azide (Intermediate I) and substituted aniline. However, in the synthetic route of WO 2014/206343 A1 (e.g., the preparation of the compound of Formula I from Compound 10 and aniline on page 34 or in particular Step K on page 51) reported, a dimer impurity, i.e., Impurity-1, was always produced with quantity ranging from a few percent to even 50% and could not completely removed by common recrystallization process.

Impurity-1

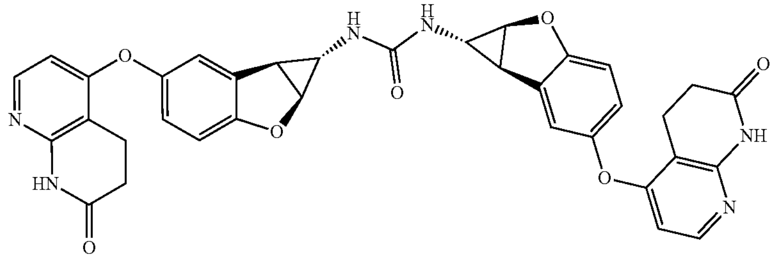

The major cause of Impurity-1 formation was found to be attributed to the moisture existed in the reaction system. Even the moisture content in the reaction system was strictly controlled, the amount of Impurity-1 was found to be significant (>>1%). In addition, Impurity-1 has very low solubilities in water and other common recrystallization solvents so that it cannot be controlled to be below 0.5% (a minimum requirement of good API quality) by recrystallization procedures. A repetitive column chromatography procedure had to be utilized to completely remove Impurity-1 from Compound 1 due to the polarity similarity of Compound 1 and Impurity-1. This costly and laborious chromatography process can only produce the pure Compound 1 in a small scale (milligrams or grams). To manufacture Compound 1 in large industrial scale with high quality, a new process without utilizing column chromatography is highly desired.

As a $2^{nd}$ generation B-RAF inhibitor, Compound 1 has demonstrated potent inhibitory activity against RAF family of serine/threonine kinases, especially against BRAF/CRAF dimers. It is a molecularly targeted therapeutic agent for the treatment of cancers with aberrations in the MAPK pathway including B-RAF mutations and K-RAS/N-RAS mutations, and has demonstrated improvement over the 1st generation B-RAF inhibitors, e.g., vemurafenib and dabrafenib.

However, Compound 1 per se, either in a crystalline form or in a neat amorphous form, has shown to have poor solubility in water or in various solutions including 0.1 HCl, and buffer solutions of different pH values. Compound 1 in a crystalline form also shows moderate hygroscopicity, as evidenced in a DVS test showing that Compound 1 in a crystalline form of hydrate is moderately hygroscopic with a sample weight gain of 4.96% at 80% relative humidity.

In addition, the preliminary drug metabolism and pharmacokinetics (DMPK) studies showed that the oral absorption of a crystalline form of Compound 1 was relatively poor in rats with a bioavailability at ~20%. A systematic screening for a suitable salt form of Compound 1 with better bioavailability was carried out. Unfortunately, it also failed to identify a stable crystalline salt, probably due to the weak basicity of Compound 1.

For poorly water-soluble compounds, crystalline nanoparticles of such compounds, upon storage, can act as seeds that induce crystallization resulting in an increase in the structural order over time and decrease in solubility. For some poorly water-soluble compounds, the amorphous form thereof may have high crystallization tendency so that they easily crystallize in miniaturized experiments, for example, at large-scale manufacturing.

Several technologies have been developed to improve the desired properties of those poorly soluble pharmaceutical compounds, including but not limited to, particle size reduction (micronization), lipid formulation, cosolvents, complexation, co-crystallization, and solid dispersions.

Among other technologies, a solid dispersion, in which the poorly soluble active pharmaceutical compound is dispersed in a polymer matrix in solid state, has been reported to provide a fast dissolution rate and/or apparent solubility in the gastric and intestinal fluids. See, e.g., A T M Serajuddin, J. Pharm. Sci. 88(10): 1058-1066 (1999) and M J Habib, Pharmaceutical Solid Dispersion Technology, Technomic Publishing Co., Inc. 2001. The active pharmaceutical compound may exist in amorphous or microcrystalline form in the mixture. Different processes have been used to prepare solid dispersions, including co-precipitation and spray drying. Although solid dispersions prepared by different processes may result in different physicochemical properties, no evidence in the literature suggests the superiority of one method over another to achieve the desired pharmacokinetic profile. See, US20080293787A1.

In particular, an amorphous form of solid dispersion comprising a poorly soluble compound dispersed in a polymer matrix has been reported to provide a stable amorphous formulation, e.g., U.S. Pat. No. 6,350,786; or to provide improved solubility and better bioavailability, e.g., U.S. Pat. No. 6,548,555.

However, there are many critical factors, which may influence the stability of amorphous form of solid dispersion. For example, Navnit Shah, et.al, (International Journal of Pharmaceutics, 438 (2012) 53-60, "Development of novel microprecipitated bulk powder (MBP) technology for manufacturing stable amorphous formulations of poorly soluble drugs") summarizes the key determinants of the stability of amorphous form as follows:

API properties e.g. Tg, Tm, log P, heat of fusion, molecular weight and ionic nature;

Properties of the stabilizing polymer e.g. ionic nature, Tg, molecular weight, hydrogen bond donors/acceptors and potential for interaction;

Drug loading in the solid dispersion;

Choice of process e.g. solubility of API and polymer in organic solvents, rate of precipitation/solidification, feasibility of interaction, physical properties of amorphous material (bulk density, porosity and particle size.

US20080293787A1 discloses a pharmaceutical composition the poorly soluble drug, i.e., (2S,3S)-2-{(R)-4-[4-(2-hydroxy-ethoxy)-phenyl]-2,5-dioxo-imidazolidin-1-yl}-3-phenyl-N-(4-propionyl-thiazol-2-yl)-butyramide (HEP) dispersed in a polymeric matrix. US20080293787A1 discloses that the solid dispersion prepared by different processes may have different properties. For example, the solid dispersion prepared by spray drying did not provide the amorphous form of the drug. The solid dispersion comprising the API and HPMCAS prepared by hot-melt extrusion showed higher bioavailability, superior dose proportionality and physical stability as compared to solid dispersions containing the same components prepared by co-precipitation. In fact, the API started to crystallize in the co-precipitation product in aqueous suspension (2% hydroxypropyl cellulose).

WO2010114928A3, also published as EP 2955180A1, disclosed solid dispersions comprising the API, propane-1-sulfonic acid {3-[5-(4-chloro-phenyl)-1H-pyrrolo[2,3-b]pyridine-3-carbonylJ-2,4-difluoro-phenyl}-amide and different polymers at different ratios may form stable amorphous solid dispersions.

Despite the variety of formulation tools available in the pharmaceutical industry, it may not be possible to easily determine whether an active pharmaceutical compound with some excipient can be formed into a stable amorphous formulation, which also demonstrates improved bioavailability and long-time stability and can be produced in a mass scale.

There is a great need for a new form of the particular poorly water-insoluble compound, i.e., Compound 1, which shows better bioavailability and has chemical and physical stability during formulation and storage of this drug. There is also a need for one form of Compound 1 (e.g., a crystalline form or an amorphous form) which has a stable physicochemical properties and is suitable for pharmaceutical manufacture, and a need for a method of mass production of the B-RAF kinase dimer inhibitors disclosed herein. Consequently, there is also a need for a new process of preparing Compound 1, which can be used to prepare Compound 1 in a mass scale with the content of impurity-1 to be controlled to be below 0.5%, even less than 0.05%, and reduce the production cost enormously by preventing the use of the costly column chromatography.

SUMMARY OF THE INVENTION

The inventors of the present application have found that the amorphous solid dispersion comprising Compound 1 as a poorly water-soluble drug and a stabilizing polymer prepared by microprecipitation bulk powder (MBP) technology shows excellent oral bioavailability (above 90%) compared with the crystalline form of Compound 1 or the neat amorphous form of Compound 1. The amorphous solid dispersion of the present application also possesses unexpected and extraordinary long-term physicochemical stability (e.g., almost up to 2 years at RT) and pharmaceutical processability (e.g., high Tg and good flowability). The high bioavailability, long-time stability, and extraordinary pharmaceutical processability of the amorphous solid dispersion prepared by MBP of the present application suggests that the amorphous solid dispersion as MBP are suitable for manufacturing drug products in clinical studies and commercial uses of large scale.

In the first aspect, disclosed herein is a stable amorphous solid dispersion comprising Compound 1 and a stabilizing polymer, wherein Compound 1 is molecularly dispersed within a polymer matrix formed by the stabilizing polymer in its solid state.

In the second aspect, disclosed herein is a complex of Formula (I) comprising Compound 1 and HPMCAS, Formula I

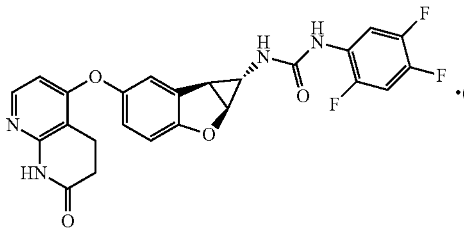

•(HPMCAS)$_m$, wherein HPMCAs is hydroxypropyl methylcellulose acetate succinate, Compound 1 is

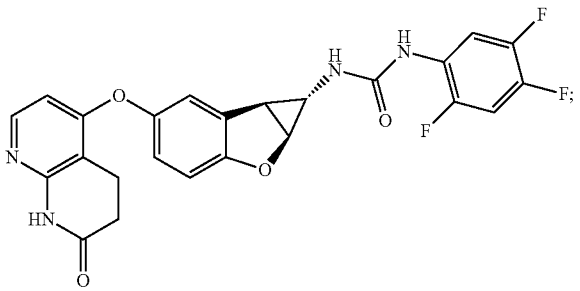 [SMILES: O=C1CCc2c(Oc3ccc4c(c3)[C@H]3[C@H](NC(=O)Nc5cc(F)c(F)cc5F)[C@H]3O4)ccnc2N1]

and m is a number so that the weight ratio of Compound 1 in the form of freebase and HPMCAS within the complex is between about 1:9 and about 9:1.

In the third aspect, disclosed herein is a crystalline form of Compound 1.

In the fourth aspect, disclosed herein is a method for preparing the stable amorphous solid dispersion or the complex disclosed herein, comprising step co-precipitating Compound 1 and HPMCAS.

In the fifth aspect, disclosed herein is an amorphous form of Compound 1.

In the sixth aspect, disclosed herein is a process for preparing the amorphous form of Compound 1.

In the seventh aspect, disclosed herein is a method of mass production of B-RAF kinase dimer inhibitors disclosed herein.

In the eighth aspect, disclosed herein is a method for treating or preventing a disease or disorder in a subject, comprising administering to said subject a therapeutically effective amount of Compound 1, wherein Compound 1 is in the amorphous solid dispersion as disclosed herein or in the complex as disclosed herein or the crystalline form disclosed herein or the neat amorphous form disclosed herein.

BRIEF DESCRIPTIONS OF THE DRAWINGS

DETAILED DESCRIPTION OF THE INVENTION

Figure 1:
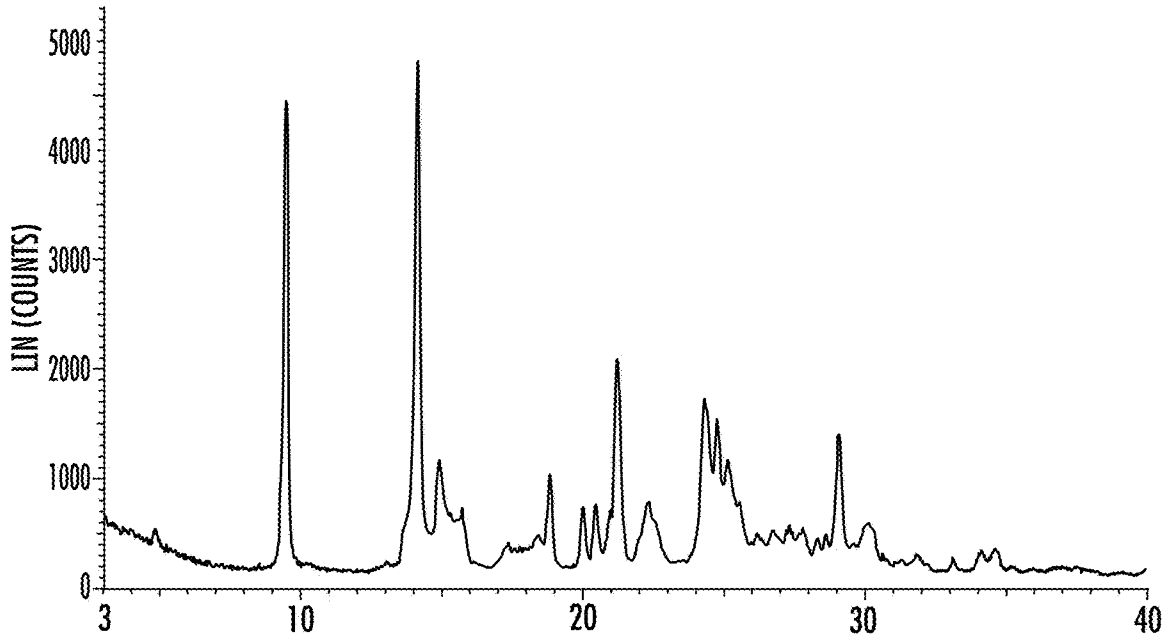
FIG. 1 shows an XRPD pattern of one crystalline form of Compound 1 (Form A) (crystallization from isopropanol/water).

In the first aspect, disclosed herein is a stable amorphous solid dispersion comprising Compound 1 and a stabilizing polymer, wherein Compound 1 is molecularly dispersed within a polymer matrix formed by the stabilizing polymer in its solid state.

A number of polymers have been reported as stabilizing polymeric excipients for pharmaceutical formulation. See, US20080293787A1, U.S. Pat. Nos. 6,350,786, and 6,548,555. Those polymers for this purpose are either cationic or anionic polymers, have a molecular weight of above about 80,000 D, a glass transition temperature equal to or greater than about 50° C., are relatively insoluble in water and preferably have pH-dependent solubility. Examples of such polymers include polyacrylates (e.g. Eudragit®, Rohm America), chitosan, Carbopol® (BF Goodrich), polyvinyl acetate phthalate, cellulose acetate phthalate, polycyanoacrylates, hydroxypropylmethyl cellulose phthalate, cellulose acetate terphthalate, hydroxypropyl methyl cellulose acetyl succinate, carboxy methyl cellulose and low substituted hydroxy propyl cellulose. However, the properties of API per se may influence on the properties of the resultant solid dispersion.

The inventors of the present application found that Compound 1 disclosed herein cannot even be disperse in Eudragit® L100-55 (methacrylic acid and ethyl acrylate copolymer), although it is a conventional stabilizing polymeric excipient.

Unexpectedly, the inventors of the present application found that HPMCAS (Hypromellose acetate succinate or hydroxypropyl methylcellulose acetate succinate), as an enteric coating material for enteric or sustained release formulations, can be co-precipitated with the particular API, Compound 1 disclosed herein, to form a stable amorphous solid dispersion as MBP, which exhibits high bioavailability, long-time stability, and extraordinary pharmaceutical processability.

The structure of HPMCAS is shown as follow:

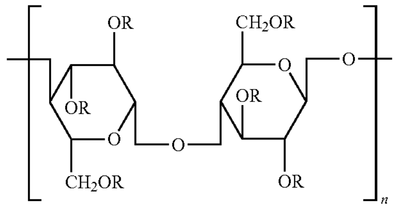

R = —H, —$CH_3$, —$COCH_3$, —$CH_2CH(CH_3)OH$, —$COCH_2CH_2COOH$, —$CH_2CH(CH_3)OCOCH_3$, —$CH_2CH(CH_3)OCOCH_2CH_2COOH$

With various contents of acetyl and succinoyl groups in the polymer, there are several types of HPMCAS, which dissolve at different pH levels. Type LF has a high ratio of succinoyl substitution to acetyl substitution (S/A ratio), while type HF has a low S/A ratio and type MF has a medium S/A ratio. With a high S/A ratio, HPMCAS-LF dissolves at a lower pH (≥5.5), compared with pH≥6.0 for type MF and pH≥6.8 for type HF. Type LF usually has 5.0-9.0% of acetyl group and 14.0-18.0% of succinoyl group; Type MF usually has 7.0-11.0%% of acetyl group and 10.0-14.0% of succinoyl group; and Type HF usually has 10.0-14.0% of acetyl group and 4.0-8.0% of succinoyl group.

The specific compositions of LF, MF and HF are summarized as follows:

| Substituents | HPMCAS-LF | HPMCAS-MF | HPMCAS-HF |
|---|---|---|---|
| —$CH_3$ | 20.0-24.0% | 21.0-25.0% | 22.0-26.0% |
| —$CH_2CH(CH_3)OH$ | 5.0-9.0% | 5.0-9.0% | 6.0-10.0% |
| —$COCH_3$ | 5.0-9.0% | 7.0-11.0% | 10.0-14.0% |
| —$COCH_2CH_2COOH$ | 14.0-18.0% | 10.0-14.0% | 4.0-8.0% |

In one embodiment, the stabilizing polymer is hydroxypropyl methylcellulose acetate succinate (HPMCAS), preferably HPMCAS with a high ratio of succinoyl substitution to acetyl substitution (S/A ratio). In other embodiment, the stabilizing polymer is any one of HPMCAS-LF, HPMCAS-MF, or HPMCAS-HF, or a mixture of two or more of the above substances.

In one embodiment, the weight ratio of Compound 1 in the form of freebase and the polymer is between about 1:9 and about 9:1; preferably between about 1:4 to about 2:3; preferably about 3:7 or about 1:4; more preferably about 1:4. Unless indicated otherwise, the ratio of Compound 1:HPMCAS is weight/weight (w/w).

In one embodiment, the stable amorphous solid dispersion has a drug-loading content of about 10% to 40%. In a preferred embodiment, the weight ratio of Compound 1 and the polymer is about 1:4 and the drug loading of the resulting dispersion is about 20%. In an even more preferred embodiment, the stable amorphous solid dispersion comprises Compound 1 in the form of freebase and HPMCAS-MF in a weight ratio of 3:7; or Compound 1 in the form of freebase and HPMCAS-MF in a weight ratio of 2:3; Compound 1 in the form of freebase and HPMCAS-MF in a weight ratio of 1:4; Compound 1 in the form of freebase and HPMCAS-LF in a weight ratio of 1:9; Compound 1 in the form of freebase and HPMCAS-LF in a weight ratio of 1:4; Compound 1 in the form of freebase and HPMCAS-LF in weight ratio of 3:7; Compound 1 in the form of freebase and HPMCAS-LF in a weight ratio of 2:3; or Compound 1 in the form of freebase and HPMCAS-HF in a weight ratio of 1:4.

In one embodiment, the stable amorphous solid dispersion is prepared by microprecipitated bulk powder (MBP) technology.

In one embodiment, the stable amorphous solid dispersion has a glass transition temperature of about 110-115° C., preferably about 111° C.

In one embodiment, the stable amorphous solid dispersion is formulated into an orally administrated formulation, e.g., tablet or capsule.

In the second aspect, disclosed herein is a complex of Formula (I) comprising Compound 1 and HPMCAS, Formula I

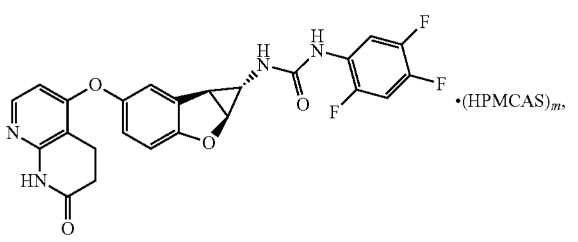

wherein HPMCAs is hydroxypropyl methylcellulose acetate succinate, Compound 1 is

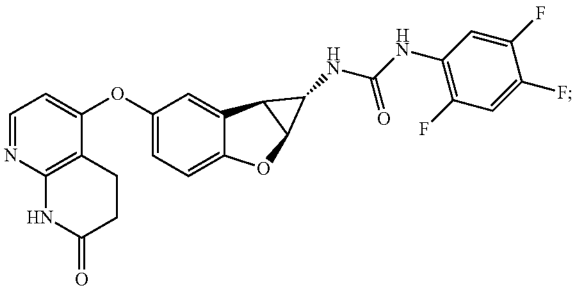 [SMILES: O=C1CCc2c(Oc3ccc4c(c3)[C@H]3[C@H](NC(=O)Nc5cc(F)c(F)cc5F)[C@H]3O4)ccnc2N1]

and m is a number so that the weight ratio of Compound 1 in the form of freebase and HPMCAS within the complex is between about 1:9 and about 9:1.

In one embodiment, HPMCAS has a high ratio of succinoyl substitution to acetyl substitution (S/A ratio). In other embodiment, HPMCAS is HPMCAS-LF, HPMCAS-MF, or HPMCAS-HF, or a mixture of two or more of the above substances.

In one embodiment, m is a number so that the weight ratio of Compound 1 in the form of freebase and the polymer within the complex is preferably between about 1:4 to about 2:3; preferably about 3:7 or about 1:4; more preferably about 1:4. In an even more preferred embodiment, the complex comprises Compound 1 in the form of freebase and HPMCAS-MF in a weight ratio of 3:7; or Compound 1 in the form of freebase and HPMCAS-MF in a weight ratio of 2:3; Compound 1 in the form of freebase and HPMCAS-MF in a weight ratio of 1:4; Compound 1 in the form of freebase and HPMCAS-LF in a weight ratio of 1:9; Compound 1 in the form of freebase and HPMCAS-LF in a weight ratio of 1:4; Compound 1 in the form of freebase and HPMCAS-LF in weight ratio of 3:7; Compound 1 in the form of freebase and HPMCAS-LF in a weight ratio of 2:3; or Compound 1 in the form of freebase and HPMCAS-HF in a weight ratio of 1:4.

In one embodiment, the complex is in an amorphous form.

In one embodiment, the complex is prepared by microprecipitated bulk powder (MBP) technology.

In one embodiment, the complex has a glass transition temperature of about 110-115° C., preferably about 111° C.

In one embodiment, the complex is formulated into an orally administrated formulation, e.g., tablet or capsule.

In the third aspect, disclosed herein is a crystalline form of Compound 1, which exhibits a long-term stability. For example, the stable crystalline form of Compound 1 does not show any significant chemical purity change when stored at 25° C.° C./60% RH for up to 12 months and no optical purity changes when stored at 25° C.° C./60% RH for up to 12 months and at 40° C./75% RH condition for up to 6 months, indicating that the stable crystalline form is a good candidate for purifying API and used as the starting materials for manufacturing the amorphous solid dispersion.

In one embodiment, the crystalline form is Form A, characterized by an XRPD pattern comprising at least three, four, five, or six diffraction peaks having 2θ angle values independently selected from the group consisting of: 4.7±0.2, 9.4±0.2, 13.6±0.2, 14.0±0.2, 14.9±0.2, and 15.6±0.2 degrees. Preferably, the crystalline form is Form A, characterized by an XRPD pattern comprising at least three, four, five, or six diffraction peaks having 2θ angle values independently selected from the group consisting of: 4.7±0.2, 9.4±0.2, 13.6±0.2, 14.0±0.2, 14.9±0.2, 15.6±0.2, 21.2±0.2, 24.3±0.2, 24.7±0.2, 25.1±0.2, and 29.1±0.2 degrees. More preferably, the crystalline form is Form A characterized by an XRPD pattern comprising diffraction peaks having 2θ angle values independently selected from the group consisting of: 4.7±0.2, 9.4±0.2, 10.2±0.2, 13.6±0.2, 14.0±0.2, 14.9±0.2, 15.6±0.2, 17.2±0.2, 17.4±0.2, 18.7±0.2, 20.0±0.2, 20.4±0.2, 21.2±0.2, 22.3±0.2, 24.3±0.2, 24.7±0.2, 25.1±0.2, 25.5±0.2, 26.8±0.2, 27.4±0.2, 27.8±0.2, 28.6±0.2, 29.1±0.2, 30.2±0.2, 31.8±0.2, 32.0±0.2, 33.1±0.2, 34.1±0.2, and 34.6±0.2 degrees.

In one embodiment, the crystalline form is Form A, substantially characterized by an XRPD pattern as shown in FIG. 1.

In other embodiment, the crystalline form is Form A*, characterized by an XRPD pattern comprising at least three, four, five, or six diffraction peaks having 2θ angle values independently selected from the group consisting of: 9.2±0.2, 14.0±0.2, 15.4±0.2, 18.7±0.2, 20.5±0.2, 24.0±0.2, and 24.9±0.2 degrees. Preferably, the crystalline form is Form A* characterized by an XRPD pattern comprising diffraction peaks having 2θ angle values independently selected from the group consisting of: 9.2±0.2, 10.8±0.2, 12.3±0.2, 14.0±0.2, 15.4±0.2, 16.5±0.2, 18.1±0.2, 18.7±0.2, 19.3±0.2, 19.8±0.2, 20.5±0.2, 21.6±0.2, 22.3±0.2, 23.2±0.2, 24.0±0.2, 24.9±0.2, 26.7±0.2, 27.8±0.2, 28.7±0.2, 29.4±0.2, 30.9±0.2, 33.2±0.2, 37.9±0.2, and 38.2±0.2 degrees.

In one embodiment, Form A has a starting temperature of 168.7° C. in DSC.

In one embodiment, Form A has a particle size distribution of $D_{90}$ within about 50 to about 70 μm, preferably about 62 μm.

Figure 19:
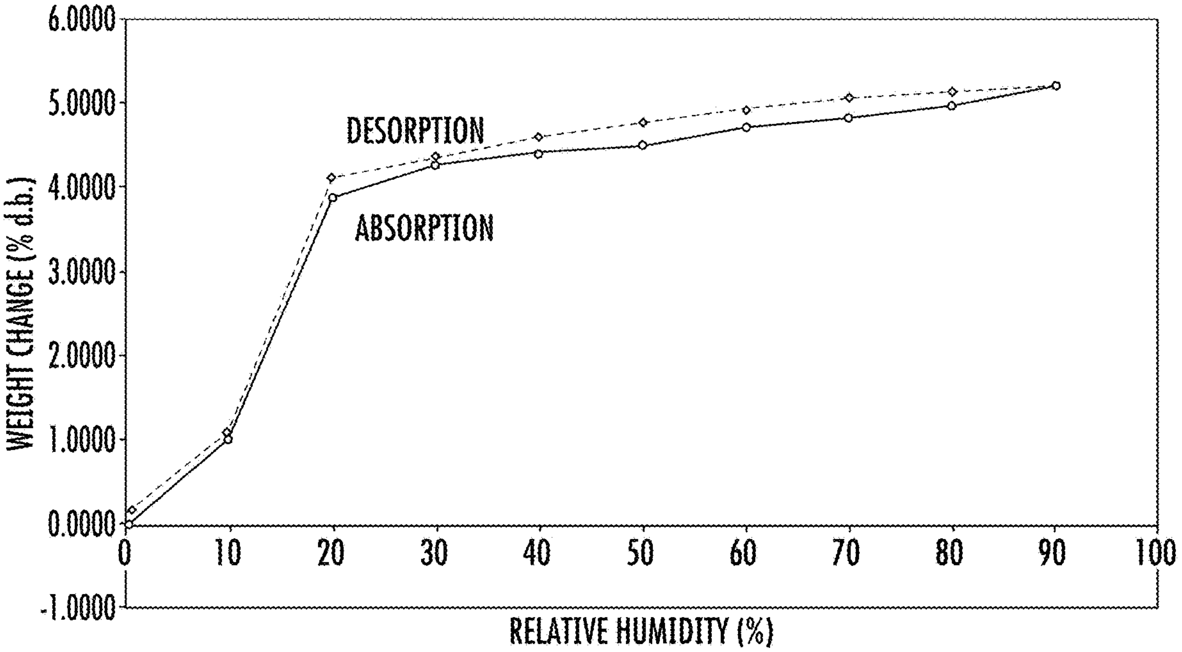
FIG. 19 shows hygroscopicity (i.e., moisture sorption) of crystalline form of Compound 1 (Form A) by DVS.

In one embodiment, Form A is substantially characterized by a DVS as shown in FIG. 19.

Figure 2:
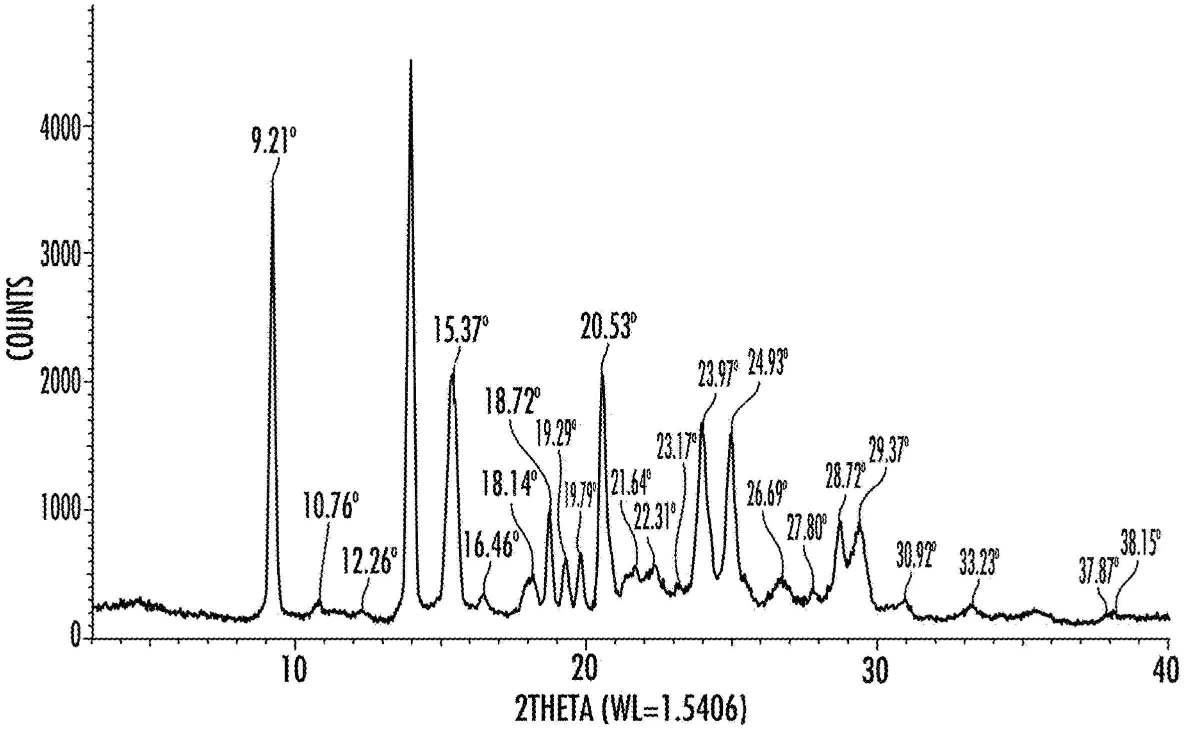
FIG. 2 shows an XRPD pattern of another crystalline form of Compound 1 (Form A*)

In one embodiment, the crystalline form is Form A*, substantially characterized by an XRPD pattern as shown in FIG. 2.

In one embodiment, the crystalline form is Form A, which is a single crystal as substantially illustrated in FIGS. 3-6**.

Figure 6:
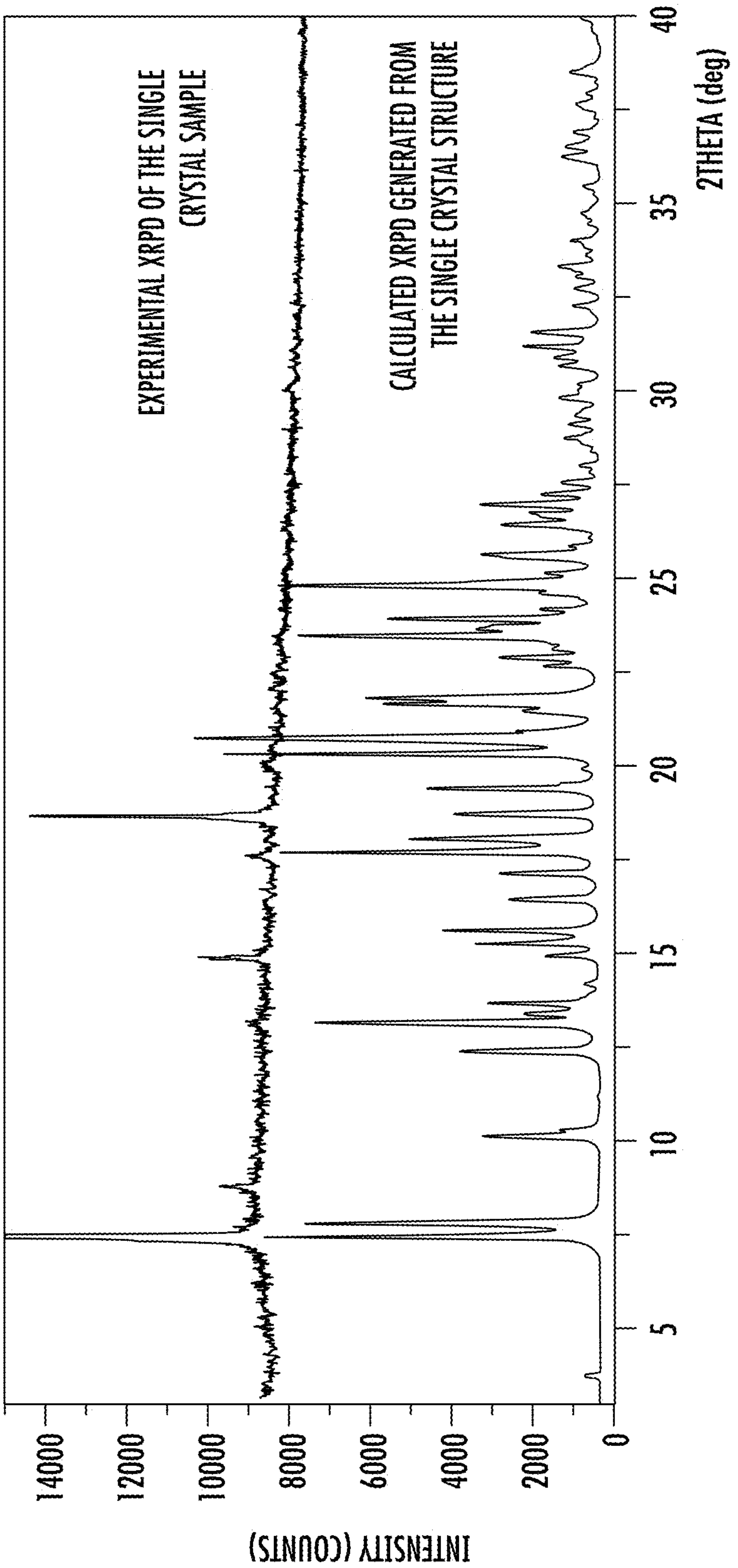
FIG. 6 shows a theoretical XRPD pattern of single crystalline of Compound 1 (Form A**) calculated using the MERCURY software.

In one embodiment, the crystalline form is a single crystal, i.e., Form A, substantially characterized by an experimental or calculated XRPD pattern as shown in FIG. 6**.

In one embodiment, the single crystal Form A** has the following cell parameters:

a=8.7232(5) Å
b=12.9311(7) Å
c=24.0303(14) Å
a=90°
β=99.513 (2)°
γ=90°.

In one embodiment, the single crystal Form A** has the cell space of monoclinic $P2_1$.

In one embodiment, Compound 1 is in neat amorphous form, which is characterized by an XRPD pattern comprising no diffraction peaks having 2θ angle values.

Also disclosed is a method for preparing crystalline Form A. The method of preparing the crystalline Form A includes crystallization (including cooling crystallization, evaporation crystallization, vacuum crystallization, reaction and salting out crystallization), recrystallization, fractional crystallization, and the like. In one embodiment, crystalline Form A is prepared by a scurrying process, comprising slurrying Compound 1 in a solvent. The method further comprises stirring during the slurrying process, such as stirring for 1-4 hours, or longer, preferably stirring for at least 4 hours, such as 5 hours, and the like. The method also includes separating the slurry material containing the precipitate of Compound 1. In one embodiment, the solvent is a polar solvent such as an ether, a carboxylic acid ester, a nitrile, a ketone, an amide, a sulfone, a sulfoxide or a halogenated hydrocarbon; more preferably, the polar solvent include, but are not limited to, acetic acid, acetone, acetonitrile, benzene, chloroform, carbon tetrachloride, dichloromethane, dimethyl sulfoxide, 1, 4-dioxane, ethanol, ethyl acetate, butanol, Tert-butanol, N, N-dimethylacetamide, N, N-dimethylformamide, formamide, formic acid, heptane, hexane, isopropanol, methanol, methyl ethyl ketone, 1-Methyl-2-pyrrolidone, mesitylene, nitromethane, polyethylene glycol, propanol, 2-propanone, pyridine, tetrahydrofuran, toluene, xylene, mixtures thereof and the like.

In one embodiment, the present invention provides a Crystalline Form of Compound 1 (Form A) prepared or purified according to the procedures depicted in the Scheme 1. Notably, the methods disclosed herein are especially suitable for reproducible, commercial-scale manufacture of Compound 1 in high quality and good yields.

Scheme 1

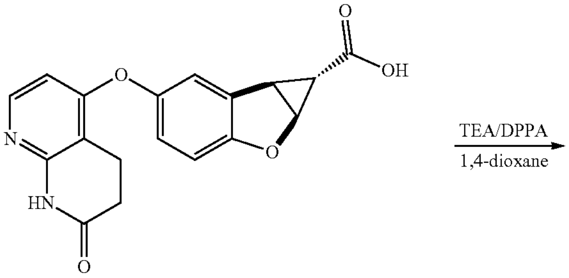

INTQ-15

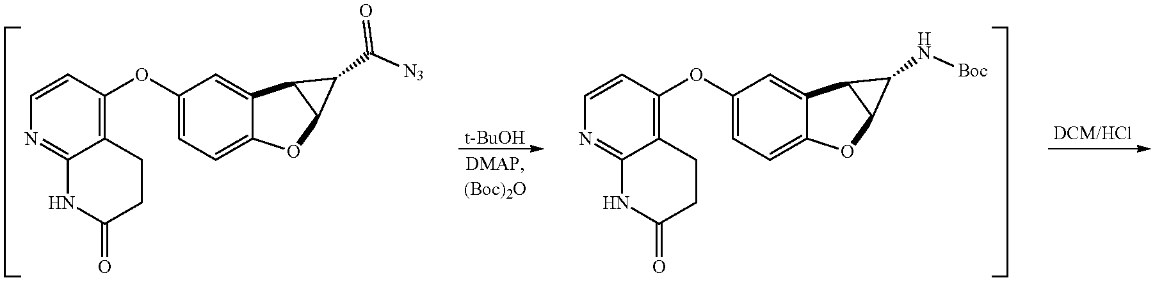

INTQ-16 INTQ-17

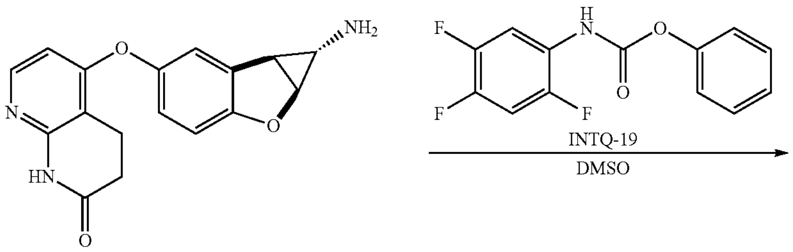

INTQ-18

-continued

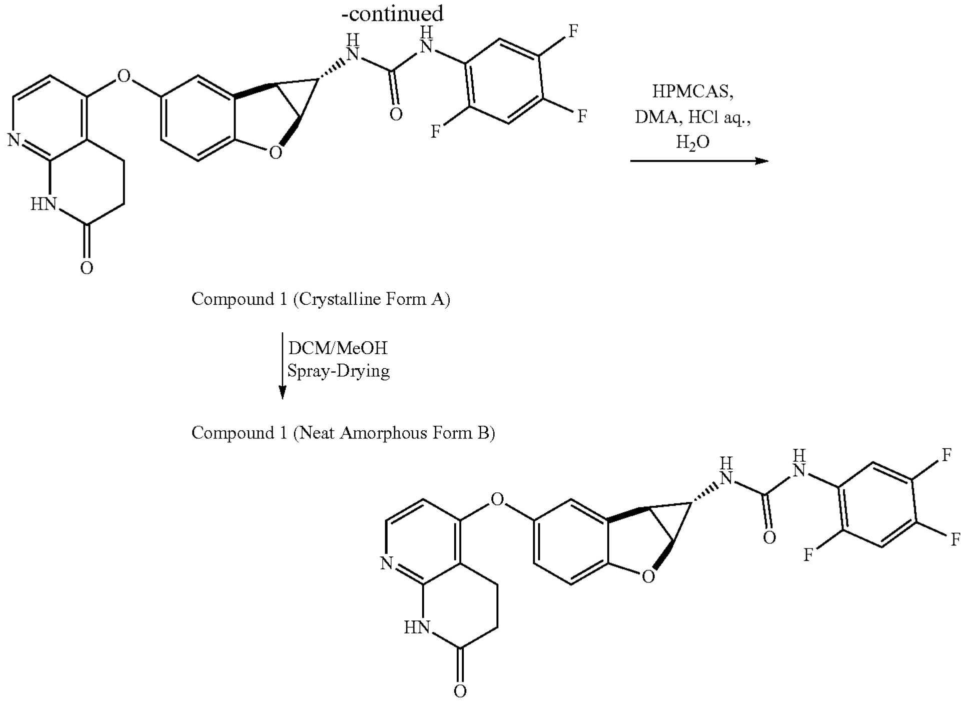

Compound 1 (Crystalline Form A)

Compound 1 (Neat Amorphous Form B)

Formula I: (HPMCAS)$_m$:
MBP Forms C, D, E, F, G and H

The freebase of Compound 1 was obtained in the Crystalline Form A during synthetic process, which is moderately hygroscopic with 4.96% water gain from 0 to 80% RH. The Crystalline Form A was changed to the Crystalline Form A* after dynamic vapor sorption (DVS).

The crystallization of the crystalline forms of the present invention can also be conducted in an appropriate solvent system containing at least one solvent by evaporation of solvent, cooling and/or by addition of anti-solvents (solvents that are less able to solubilize the Compound 1, including but not limited to those described herein) to achieve supersaturation in the solvent system.

Crystallization may be done with or without seed crystals, which is described in the present invention.

The individual crystalline forms provided by the present invention develop under specific conditions dependent on the particular thermodynamic and equilibrium properties of the crystallization process. Therefore, a person skilled in the art will know that the crystals formed are a consequence of the kinetic and thermodynamic properties of the crystallization process. Under certain conditions (e.g., solvent, temperature, pressure, and concentration of the compound), a particular crystalline form may be more stable than another crystalline form (or in fact more stable than any other crystalline forms). However, the relatively low thermodynamic stability of particular crystals may have advantageous kinetic stability. Additional factors other than kinetics, such as time, impurity distribution, stirring, and the presence or absence of seed crystals, etc., may also affect the crystalline form.

In the fourth aspect, disclosed herein is a method for preparing the stable amorphous solid dispersion or the complex disclosed herein, comprising step co-precipitating Compound 1 and HPMCAS.

In one embodiment, Compound 1 and HPMCAS simultaneously precipitate out to form a molecular dispersion of Compound 1 in the matrix formed by HPMCAS.

In one embodiment, the method comprises the step of a solvent controlled precipitation.

In a preferred embodiment, the method comprises the step of microprecipitated bulk powder (MBP) technology.

In one embodiment, HPMCAS has a high ratio of succinoyl substitution to acetyl substitution (S/A ratio). In other embodiment, HPMCAS is HPMCAS-LF, HPMCAS-MF, or HPMCAS-HF, or a mixture of two or more of the above substances.

In one embodiment, Compound 1 is in a crystalline form or amorphous form. In a preferred embodiment, Compound 1 is Form A as disclosed herein.

In one embodiment, the weight ratio of Compound 1 in the form of freebase and HPMCAS is between about 1:9 to about 9:1, preferably between about 1:4 to about 2:3; preferably about 3:7 or about 1:4; more preferably about 1:4.

In one embodiment, HPMCAS is HPMCAS-LF, or HPMCAS-MF, or HPMCAS-HF; and Compound 1 in the form of freebase and HPMCAS-MF is in a weight ratio of 3:7; or Compound 1 in the form of freebase and HPMCAS-MF is in a weight ratio of 2:3; Compound 1 in the form of freebase and HPMCAS-MF is in a weight ratio of 1:4; Compound 1 in the form of freebase and HPMCAS-LF is in a weight ratio of 1:9; Compound 1 in the form of freebase and HPMCAS-LF is in a weight ratio of 1:4; Compound 1 in the form of freebase and HPMCAS-LF is in weight ratio of 3:7; Compound 1 in the form of freebase and HPMCAS-LF is in a weight ratio of 2:3; or Compound 1 in the form of freebase and HPMCAS-HF in a weight ratio of 1:4.

In one embodiment, the method comprises dissolving Compound 1 and HPMCAS in an organic solvent. In a preferred embodiment, the organic solvent is N,N-dimethylformamide (DMF), N,N-dimethylacetamide (DMAc), dimethyl sulfoxide (DMSO) or N-methyl-2-pyrrolidone (NMP).

In one embodiment, the resulting solution of Compound 1 and HPMCAS is added into water or an acidic aqueous solution, whereby Compound 1 and HPMCAS simultaneously precipitate out to form a solid dispersion or a complex disclosed herein. In a preferred embodiment, the acidic aqueous solution is aqueous hydrochloric acid (HCl). In a preferred embodiment, water or the acidic aqueous solution is optionally cooled. In an even preferred embodiment, water or the acidic aqueous solution is optionally cooled to 2-8° C.

In one embodiment, the resulting solid is dried to give the amorphous solid dispersion as MBP or the complex.

In one embodiment, the resulting solid is further optionally micronized by, e.g., jet-milling to give a powder with a particle size suitable for drug formulation, e.g., of $D_{90}$ less than 150 μm or 200 μm.

In one embodiment, the solid dispersion or the complex is in an amorphous form.

In one embodiment, the solid dispersion or the complex has a glass transition temperature of about 110-115° C., preferably about 111° C.

In one embodiment, the method disclosed herein comprises:

a) dissolving Compound 1 and HPMCAS in an organic solvent;

b) co-precipitating Compound 1 and HPMCAS by adding the solution of a) into water or an acidic aqueous solution; and c) washing the resulting solid with water and/or aqueous hydrochloric acid to remove the organic solvent.

In one embodiment, the amorphous solid dispersion disclosed herein can also be prepared by spray-drying.

In the fifth aspect, disclosed herein is a neat amorphous form of Compound 1. The neat amorphous form of Compound 1 disclosed herein has a potential use in pharmaceutical formulation because (1) it does not show any change of crystalline form during a test period of 14 days, i.e., does not show crystalline peaks at 14 days; and (2) it shows a relative higher bioavailability than the crystalline Form A.

Figure 7:
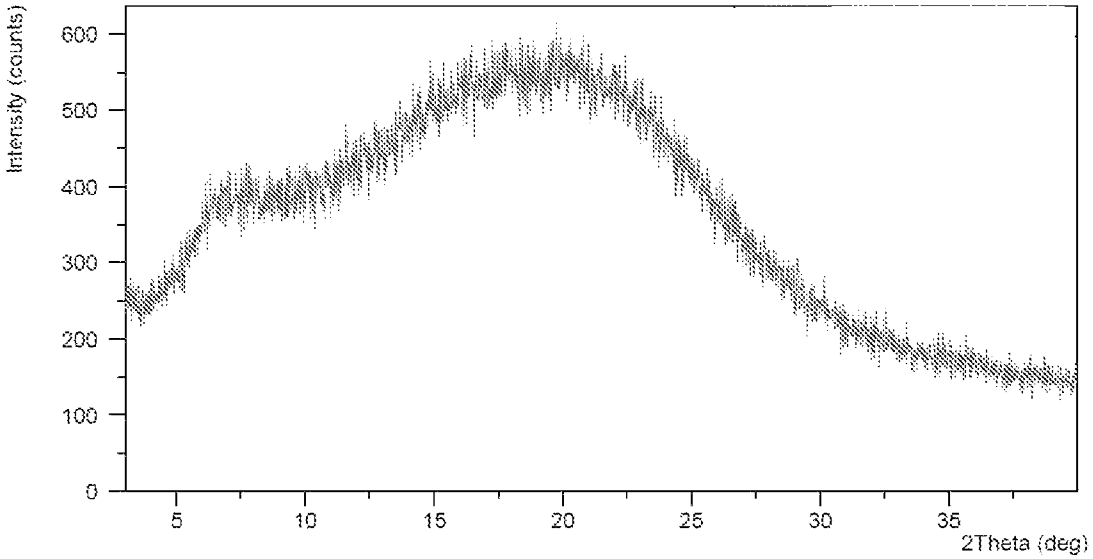
FIG. 7 shows an XRPD pattern of the neat amorphous form of Compound 1 (Form B).

In one embodiment, the neat amorphous form of Compound 1 disclosed herein is substantially characterized by an XRPD pattern as shown in FIG. 7 having no peak diffraction angels.

Figure 21:
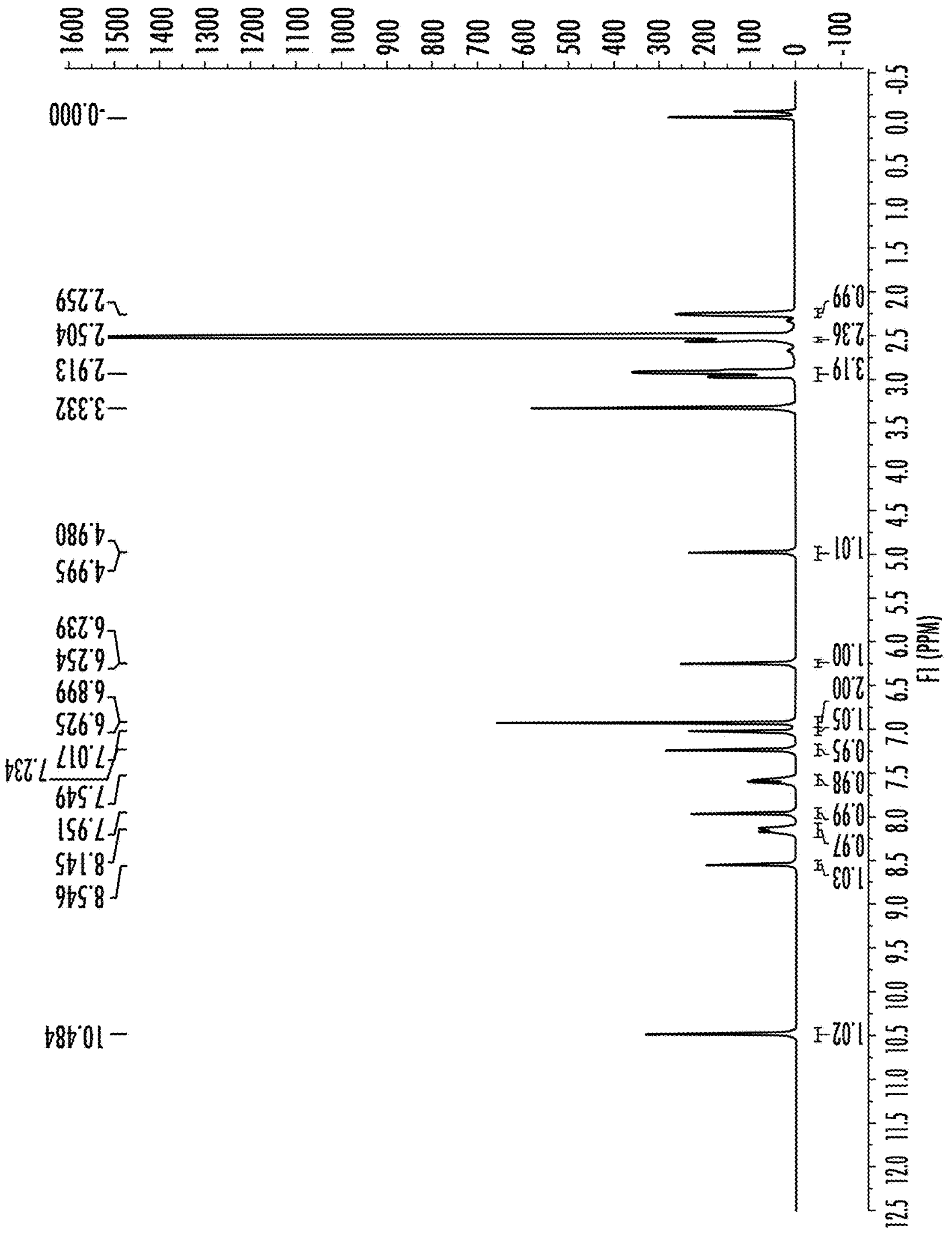
FIG. 21 shows a $^{1}$H-NMR spectrum of neat amorphous form of Compound 1 (Form B)

In one embodiment, the neat amorphous form of Compound 1 disclosed herein is substantially characterized by $^1$H-NMR pattern as shown in FIG. 21.

In one embodiment, the neat amorphous form of Compound 1 disclosed herein has a glass transition temperature of between about 135 to 143° C., preferably about 138.3° C.

In one embodiment, the neat amorphous form of Compound 1 disclosed herein has a particle size distribution of $D_{90}$ within about 60 to about 80 μm, a particle size distribution of $D_{50}$ within about 2 to about 6 μm, a particle size distribution of $D_{10}$ within about 1 to about 2 μm; preferably a particle size distribution of $D_{90}$ of about 69.9 μm, a particle size distribution of $D_{50}$ of 3.5 μm, a particle size distribution of $D_{10}$ of 1.4 μm.

Also disclosed herein is a method for preparing the neat amorphous form of Compound 1, comprising spray-drying a crystalline form of Compound 1 in a polar solvent to obtain a powdery substance.

Preferably, the polar solvent comprises an ether, a carboxylic acid ester, a nitrile, a ketone, an amide, a sulfone, a sulfoxide or a halogenated hydrocarbon. More preferably, the polar solvent comprises, but not limited to, acetic acid, acetone, acetonitrile, benzene, chloroform, carbon tetrachloride, dichloromethane, dimethyl sulfoxide, 1, 4-dioxane, ethanol, ethyl acetate, butanol, uncle Butanol, N, N-dimethylacetamide, N, N-dimethylformamide, formamide, formic acid, heptane, hexane, isopropanol, methanol, methyl ethyl ketone, 1-methyl-2-pyrrolidone, mesitylene, nitromethane, polyethylene glycol, propanol, 2-propanone, pyridine, tetrahydrofuran, toluene, xylene, mixtures thereof, etc. Preferably, the polar solvent is a mixture of halogenated hydrocarbons/amides, such as a mixture of DCM/MeOH.

Preferably, the spray drying is performed by a spray dryer. Preferably, the inlet temperature of the spray dryer is set to about 50 to 70° C., and the outlet temperature of the spray dryer is set to about 25 to 45° C. More preferably, the inlet temperature of the spray dryer is set to about 60° C., and the outlet temperature of the spray dryer is set to about 35° C.

In the seventh aspect, disclosed herein is a method of mass production of B-RAF kinase dimer inhibitors disclosed herein. In particular, the method disclosed herein is suitable for preparation of the B-RAF kinase dimer inhibitors disclosed herein, especially Compound 1, in a high quality, high yield reproducible, commercial scale manner. The method disclosed herein reduces the production cost enormously by preventing the use of the costly column chromatography and controls the content of impurity-1 to be below 0.5% under the conditions disclosed herein, even less than 0.05% under the optimized conditions.

In one embodiment, the method comprise: an amine of Formula Ia and a protected carbamoyl compound of Formula Ib are subjected to a condensation reaction to obtain a compound of Formula I or a pharmaceutically acceptable salt thereof,

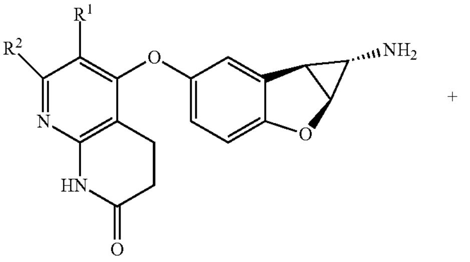

Ia

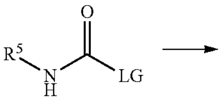

Ib

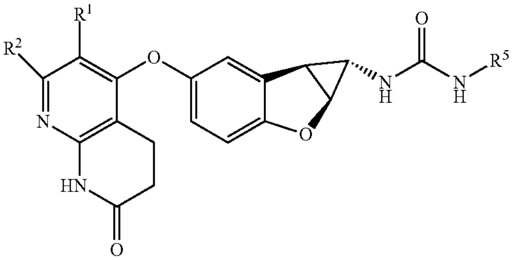

I wherein, $R^1$ and $R^2$, which may be the same or different, are each independently selected from hydrogen, halogen, alkyl, alkenyl, cycloalkyl, aryl, heterocyclyl, heteroaryl, alkynyl, —CN, —$NR^6R^7$, —$OR^6$, —$COR^E$, —$CO_2R^6$, —$CONR^6R^7$, —C(=$NR^6$)$NR^7R^8$, —$NR^6COR^7$, —$NR^6CONR^7R^8$, —$NR^6CO_2R^7$, —$SO_2R^6$, —$NR^6SO_2NR^7R^8$, —$NR^6SO_2R^7$ and —$NR^6SO_2$aryl, wherein said alkyl, alkenyl, alkynyl, cycloalkyl, heterocyclyl, heteroaryl, aryl and heterocyclyl are each independently optionally substituted with one or two or three substituents $R^9$;

$R^5$ is selected from alkyl, cycloalkyl, heterocyclyl, aryl and heteroaryl, each of which is independently optionally substituted with one or two or three substituents $R^9$;

LG is a leaving group;

$R^6$, $R^7$ and $R^8$, which may be the same or different, are each independently selected from H, alkyl, alkenyl, alkynyl, cycloalkyl, heterocyclyl, aryl and heteroaryl; or ($R^6$ and $R^7$) and/or ($R^7$ and $R^8$) together with the atom(s) to which they are attached, each form a ring selected from heterocyclyl and heteroaryl rings optionally substituted with one or two or three substituents $R^9$; $R^9$ is selected from halogen, haloalkyl, alkyl, alkenyl, cycloalkyl, aryl, heteroaryl, heterocyclyl, alkynyl, oxo, -alkyl-$NR^aR^b$, —CN, —$OR^a$, —$NR^aR^b$, —$COR^a$, —$CO_2R^a$, —$CONR^aR^b$, —C(=$NR^a$)$NR^bR^c$, nitro, —$NR^aCOR^b$, —$NR^aCONR^aR^b$, —$NR^aCO_2R^b$, —$SO_2R^a$, —$SO_2$aryl, —$NR^aSO_2NR^bR^c$, $NR^aSO_2R^b$ and —$NR^aSO_2$aryl, wherein said cycloalkyl, aryl, heteroaryl or heterocyclyl are each independently substituted with one or two or three substituents selected from halogen, alkyl and haloalkyl, wherein $R^a$, $R^b$ and $R^c$ are each independently selected from H, haloalkyl, alkyl, alkenyl, alkynyl, cycloalkyl, heterocyclyl, aryl and heteroaryl, or ($R^a$ and $R^b$) and/or ($R^b$ and $R^c$) together with the atom(s) to which they are attached, each form a ring selected from heterocyclyl and heteroaryl rings optionally substituted with halogen and alkyl.

In one embodiment, the condensation reaction of an amine of Formula Ia and a protected carbamoyl compound of Formula Ib is conducted in an organic solvent. In one embodiment, the condensation reaction is conducted with a solution of an amine of Formula Ia in an organic solvent and a protected carbamoyl compound of Formula Ib. In one embodiment, the condensation reaction is conducted with an amine of Formula Ia and a solution of a protected carbamoyl compound of Formula Ib in an organic solvent.

In one embodiment, the condensation reaction is conducted in an anhydrous condition. In one embodiment, the condensation reaction is conducted by adding a protected carbamoyl compound of Formula Ib into a solution of an amine of Formula Ia in an organic solvent.

In one embodiment, the organic solvent is typically selected from the group consisting of a non-polar solvent, a polar protic solvent and a polar aprotic solvent, or a mixture thereof. Suitable polar aprotic solvents include, but are not limited to, N-methylpyrrolidone, N-methylmorpholine, methyl isobutyl ketone, methyl ethyl ketone, tetrahydrofuran, dichloromethane, ethyl acetate, acetone, N, N-dimethylformamide, acetonitrile and dimethyl sulfoxide. Suitable polar protons solvents include, but are not limited to, methanol, ethanol, n-propanol, isopropanol, n-butanol, isobutanol, tert-butanol, and acetic acid. Suitable non-polar solvents include, but are not limited to, dioxane, toluene, hexane, cyclohexane and diethyl ether.

In a further embodiment, the organic solvent is a polar aprotic solvent. In still further embodiments, the organic solvent is N-methylpyrrolidone, N-methylmorpholine, methyl isobutyl Ketone, methyl ethyl ketone, tetrahydrofuran, dichloromethane, ethyl acetate, acetone, N, N-dimethylformamide, acetonitrile and dimethyl sulfoxide, or a mixture of two or more. In a further embodiment, the organic solvent is N-methylmorpholine, dimethyl sulfoxide or a mixture of both.

In one embodiment, there is no particular limitation to the amount of the organic solvent, provided that the amine of Formula Ia is sufficiently dissolved.

In one embodiment, the condensation reaction is conducted in vacuum. In a further embodiment, the condensation reaction is conducted in a vacuum as low as about −0.10 MPa.

In one embodiment, the condensation reaction is conducted at a temperature of about 10 to 50° C. or at a temperature of about 15 to 25° C. In a further embodiment, the condensation reaction is conducted at a temperature of about 20±5° C.

In one embodiment, the condensation reaction is carried out for at least about 0.5 hours, at least about 1 hour, at least about 2 hours, at least about 3 hours, at least about 4 hours. In a further embodiment, the condensation reaction is carried out for about 3 hours.

In one embodiment, the content of impurity-1 in the product of the condensation reaction is below 0.5%, even less than 0.05% (detected by HPLC) at the best mode.

In one embodiment, $R^1$ and $R^2$ are both hydrogen.

In one embodiment, $R^5$ is aryl, optionally substituted with one or two or three substituents $R^9$. In a further embodiment, $R^5$ is phenyl, optionally substituted with one or two or three halogen. In a still further embodiment, $R^5$ is 2, 4, 5-trifluorophenyl.

In one embodiment, the compound of Formula I is 1-((1S, 1aS, 6bS)-5-((7-oxo-5, 6, 7, 8-tetrahydro-1, 8-naphthyridin-4-yl)oxy)-1a, 6b-dihydro-1H-cyclopropa[b]benzofuran-1-yl)-3-(2, 4, 5-trifluorophenyl)urea or a pharmaceutically acceptable salt thereof.

Although there is no particular limitation to the leaving group, in one embodiment, LG is alkyl, cycloalkyl, aryl, heteroaryl, heterocyclyl or —$OR^a$, wherein the alkyl, cycloalkyl, aryl, heteroaryl or heterocyclyl is optionally substituted with one or more substituents selected from halogen, nitro, hydroxy or alkoxy, and wherein $R^a$ is alkyl, cycloalkyl, aryl, heteroaryl or heterocyclyl, optionally substituted with one or more substituents selected from halogen, nitro, —CN, hydroxy or alkoxy. In a further embodiment, LG is —$OR^a$, wherein $R^a$ is phenyl, optionally substituted with one or more substituents selected from halogen, nitro, —CN, hydroxy or alkoxy. In a still further embodiment, LG is unsubstituted phenoxy.

In a still further embodiment, the compound of Formula Ib is

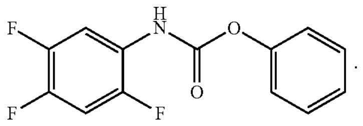 [SMILES: O=C(Nc1cc(F)c(F)cc1F)Oc1ccccc1]

In one embodiment, the compound of Formula Ia is prepared by reacting a compound of Formula Ia-2 in an organic solvent in the presence of an acid,

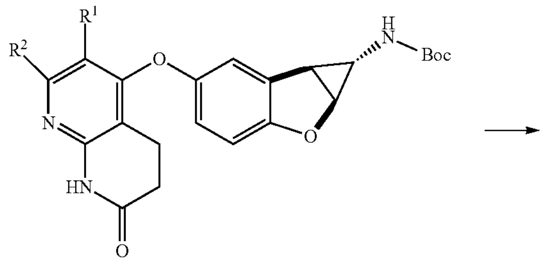

Ia-2

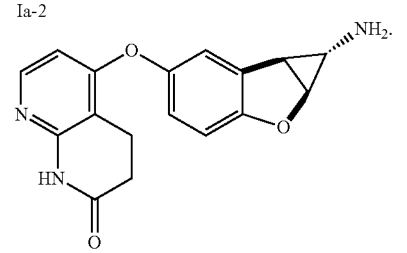

Ia

In a further embodiment, the organic solvent is selected from the group consisting of a non-polar solvent, a polar protic solvent, and a polar aprotic solvent, or a mixture thereof. Suitable polar aprotic solvents include, but are not limited to, N-methylpyrrolidone, N-methylmorpholine, methyl isobutyl ketone, methyl ethyl ketone, tetrahydrofuran, dichloromethane, ethyl acetate, acetone, N, N-dimethylformamide, acetonitrile and dimethyl sulfoxide. Suitable polar protic solvents include, but are not limited to, methanol, ethanol, n-propanol, isopropanol, n-butanol, isobutanol, tert-butanol and acetic acid. Suitable non-polar solvents include, but are not limited to, dioxins Alkane, toluene, hexane, cyclohexane and diethyl ether. In a still further embodiment, the solvent is ethanol or dichloromethane In a further embodiment, the acid is a mineral acid, for example selected from the group consisting of hydrochloric acid, phosphoric acid, hydrobromic acid, sulfuric acid, sulfurous acid and nitric acid; and an organic acid, for example selected from the group consisting of malic acid, maleic acid, and fumaric acid, tartaric acid, succinic acid, citric acid, lactic acid, methanesulfonic acid, p-toluenesulfonic acid, 2-hydroxyethanesulfonic acid, benzoic acid, salicylic acid, stearic acid, alkanoic acid (such as acetic acid and $HOOC—(CH_2)_n—COOH$, wherein n is selected from 0-4).

There is no particular limitation to the reaction temperature, which is usually carried out at room temperature.

In one embodiment, the compound of Formula Ia-2 is prepared by reacting a compound of Formula Ia-1 in $(Boc)_2O$/t-BuOH in the presence of a catalyst.

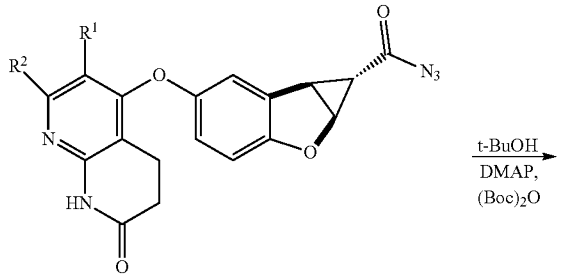

Ia-1

-continued

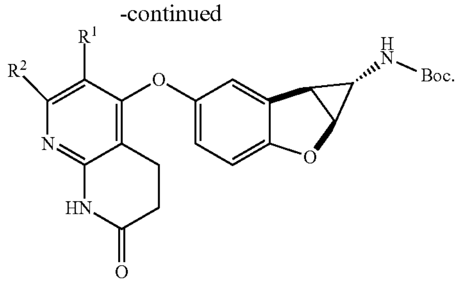

Ia-2

The preparation of the compound of Formula Ia-2 from the compound of formula Ia-1 is usually carried out at a temperature of about 70-100° C., preferably about 85±5° C.

Although Impurity-1 is also formed during the Curtis rearrangement reaction of the acyl azide of formula Ia-1 and t-butanol, the solubility and polarity of Impurity-1 differ greatly from Formula Ia-2. Therefore, Impurity-1 can easily be removed by filtering with a silica gel pad during the reaction, thereby obtaining the intermediate amine of the formula Ia free of impurities. In one embodiment, Impurity-1 may be removed after formation of the t-butyl carbamate of Formula Ia-2 from the acyl azide of Formula Ia-1. In another embodiment, Impurity-1 may be removed after the formation of an amine of Formula Ia from the tert-butyl carbamate of formula Ia-2, which further reduces the cost and is more convenient. The method of removing Impurity-1 includes a conventional method such as silica gel pad or diatomaceous earth filtration and the other suitable industrial procedure.

In one embodiment, the catalyst is DMAP.

Also disclosed herein is a compound of Formula Ia

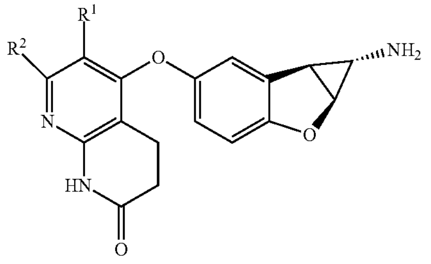

or a pharmaceutically acceptable salt thereof, wherein $R^1$ and $R^2$ are defined as above. In one embodiment, the compound of Formula Ia is

INTQ-18

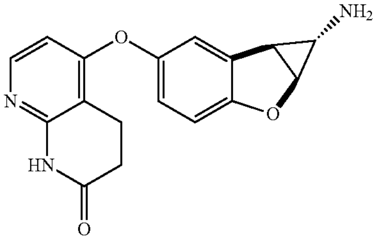

or a pharmaceutically acceptable salt thereof. In a further embodiment, the compound of Formula Ia is

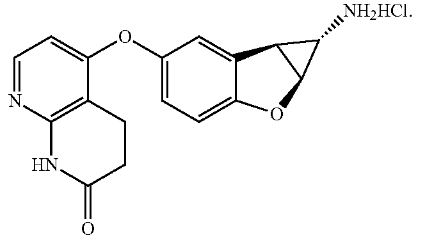

In the eighth aspect, disclosed herein is a method for treating or preventing a disease or disorder responsive to inhibition of Raf kinases in a subject, comprising administering to said subject a therapeutically effective amount of Compound 1, wherein Compound 1 is in the amorphous solid dispersion as disclosed herein or in the complex as disclosed herein or the crystalline form disclosed herein or the neat amorphous form disclosed herein.

In one embodiment, the disease or disorder is a cancer selected from the group consisting of brain cancer, lung cancer, kidney cancer, bone cancer, liver cancer, bladder cancer, breast, head and neck cancer, ovarian cancer, melanoma, skin cancer, adrenal cancer, cervical cancer, lymphoma, or thyroid tumors and their complications.

In another embodiment, the disease is BRAF (V600E or non-V600E) or NRAS or KRAS mutant cancer selected from brain cancer, lung cancer, kidney cancer, bone cancer, liver cancer, bladder cancer, breast, head and neck cancer, ovarian cancer, melanoma, skin cancer, adrenal cancer, cervical cancer, lymphoma, or thyroid tumors and their complications.

In another embodiment, the administered dosage of Compound 1 is 1-200 mg/day, and the administration frequency is one to three times a day.

In another embodiment, the administered dosage of Compound 1 is 2.5-100 mg/day, and the administration frequency is one to three times a day.

In another embodiment, the administered dosage of Compound 1 is 5-50 mg/day, and the administration frequency is one time a day.

In one embodiment, the subject is rat, dog, or human being.

In a six aspect, disclosed herein is a pharmaceutical composition comprising an effective amount of Compound 1, in particular Compound 1 in any of Form A, A*, A**, B, C, D, E, F, G, H, I, J or K disclosed herein. The active compound(s) can be 1-99% (by weight), preferably 1-50% (by weight), or more preferably 1-30% (by weight), or most preferably, 1-20% (by weight), of the composition.

The pharmaceutical compositions can be administrated orally in forms such as capsules, tablets, pills, powders, sustained release injection in such form as a sterile solution, suspension or emulsion; through a local treatment form such as paste, cream, or ointment; or via a rectal form such as suppositories. The pharmaceutical compositions may be in a unit dosage form that is suitable for precise dosing applications.

Suitable pharmaceutical carriers include water, various organic solvents and various inert diluents or fillers. If necessary, the pharmaceutical compositions may contain various additives, such as spices, adhesives and excipients. For oral administration, tablets and capsules can contain various excipients such as citric acid, a variety of disintegrant agents such as starch, alginic acids, and some silicates, and a variety of adhesives such as sucrose, gelatin and Arabic gum. In addition, lubricants including magnesium stearate and talc fillers are commonly used in the production of tablets. The same types of solid components can also be used to formulate soft and hard gelatin capsules. When an aqueous suspension is needed for oral administration, the active compound can be mixed with a variety of sweeteners or flavoring agents, pigments or dye combinations. If necessary, a variety of emulsifiers can be employed or suspensions generated; diluents such as water, ethanol, propylene glycol, glycerin, or their combination can be utilized.

The above-described pharmaceutical compositions are preferably administrated orally.

The above-described pharmaceutical compositions are preferably in the capsule or tablet form.

As used herein, the following words, phrases and symbols are generally intended to have the meanings as set forth below, except to the extent that the context in which they are used indicates otherwise. The following abbreviations and terms have the indicated meanings throughout:

The term "alkyl" herein refers to a hydrocarbon group selected from linear and branched saturated hydrocarbon groups comprising from 1 to 18, such as from 1 to 12, further such as from 1 to 10, more further such as from 1 to 6, carbon atoms. Examples of the alkyl group can be selected from methyl, ethyl,1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group can be selected from 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$) and 3,3-dimethyl-2-butyl ($—CH(CH_3)C(CH_3)_3$) groups.

The term "alkenyl" herein refers to a hydrocarbon group selected from linear and branched hydrocarbon groups comprising at least one C═C double bond and from 2 to 18, such as from 2 to 6, carbon atoms. Examples of the alkenyl group may be selected from ethenyl or vinyl ($—CH═CH_2$), prop-1-enyl ($—CH═CHCH_3$), prop-2-enyl ($—CH_2CH═CH_2$), 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, and hexa-1,3-dienyl groups.

The term "alkynyl" herein refers to a hydrocarbon group selected from linear and branched hydrocarbon group, comprising at least one CC triple bond and from 2 to 18, such as from 2 to 6, carbon atoms. Examples of the alkynyl group include ethynyl ($—C≡CH$), 1-propynyl ($—C≡CCH_3$), 2-propynyl (propargyl, $—CH_2C≡CH$), 1-butynyl, 2-butynyl, and 3-butynyl groups.

The term "cycloalkyl" herein refers to a hydrocarbon group selected from saturated and partially unsaturated cyclic hydrocarbon groups, comprising monocyclic and polycyclic (e.g., bicyclic and tricyclic) groups. For example, the cycloalkyl group may comprise from 3 to 12, such as 3 to 8, further such as 3 to 6, 3 to 5, or 3 to 4 carbon atoms. Even further for example, the cycloalkyl group may be selected from monocyclic group comprising from 3 to 12, such as 3 to 8, 3 to 6 carbon atoms. Examples of the monocyclic cycloalkyl group include cyclopropyl, cyclobutyl, cyclopentyl, cyclohexyl, cycloheptyl, cyclooctyl, cyclononyl, cyclodecyl, cycloundecyl, and cyclododecyl groups. Examples of the bicyclic cycloalkyl groups include those having from 7 to 12 ring atoms arranged as a bicyclic ring selected from [4,4], [4,5], [5,5], [5,6] and [6,6] ring systems, or as a bridged bicyclic ring selected from bicyclo [2.2.1]heptane, bicyclo[2.2.2]octane, and bicyclo[3.2.2] nonane. Further examples of the bicyclic cycloalkyl groups include those arranged as a bicyclic ring selected from [5,6] and [6,6] ring systems, such as

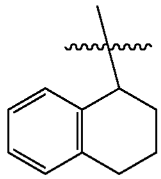

and

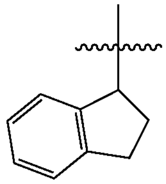

wherein the wavy lines indicate the points of attachment. The ring may be saturated or have at least one double bond (i.e. partially unsaturated), but is not fully conjugated, and is not aromatic, as aromatic is defined herein.

The term "Aryl" herein refers to a group selected from:

5- and 6-membered carbocyclic aromatic rings, for example, phenyl;

bicyclic ring systems such as 7 to 12 membered bicyclic ring systems wherein at least one ring is carbocyclic and aromatic, selected, for example, from naphthalene, indane, and 1,2,3,4-tetrahydroquinoline; and tricyclic ring systems such as 10 to 15 membered tricyclic ring systems wherein at least one ring is carbocyclic and aromatic, for example, fluorene.

The term "halogen" or "halo" herein refers to F, Cl, Br or I.

The term "heteroaryl" herein refers to a group selected from:

5- to 7-membered aromatic, monocyclic rings comprising at least one heteroatom, for example, from 1 to 4, or, in some embodiments, from 1 to 3, heteroatoms, selected from N, O, and S, with the remaining ring atoms being carbon;

8- to 12-membered bicyclic rings comprising at least one heteroatom, for example, from 1 to 4, or, in some embodiments, from 1 to 3, or, in other embodiments, 1 or 2, heteroatoms, selected from N, O, and S, with the remaining ring atoms being carbon and wherein at least one ring is aromatic and at least one heteroatom is present in the aromatic ring; and 11- to 14-membered tricyclic rings comprising at least one heteroatom, for example, from 1 to 4, or in some embodiments, from 1 to 3, or, in other embodiments, 1 or 2, heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" herein refers to a ring selected from 4- to 12-membered monocyclic, bicyclic and tricyclic, saturated and partially unsaturated rings comprising at least one carbon atoms in addition to at least one heteroatom, such as from 1-4 heteroatoms, further such as from 1-3, or further such as 1 or 2 heteroatoms, selected from oxygen, sulfur, and nitrogen. "Heterocycle" herein also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl. "Heterocycle" herein also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinyl, imidazolinyl, pyrimidinonyl, 1,1-dioxo-thiomorpholinyl, 3-azabicyco [3.1.0]hexanyl, 3-azabicyclo[4.1.0]heptanyl and azabicyclo [2.2.2]hexanyl. A substituted heterocycle also includes a ring system substituted with one or more oxo moieties, such as piperidinyl N-oxide, morpholinyl-N-oxide, 1-oxo-1-thiomorpholinyl and 1,1-dioxo-1-thiomorpholinyl.

The term "about" as used herein, unless indicated otherwise, denotes that a number (e.g., temperature, pH, volume, etc.) can vary within ±10%, preferably within ±5%.

The following synthetic methods, specific examples, and efficacy tests further describe certain aspects of the present invention. They shall not limit or restrict the scope of the present invention in any way.

EXAMPLES

The examples below are intended to be exemplary and efforts have been made to ensure accuracy with respect to numbers used (for example, amounts, temperature, etc.), but some experimental errors and deviations should be accounted for. Unless indicated otherwise, temperature is in degrees Centigrade. Reagents were purchased from commercial suppliers such as Sigma-Aldrich, Alfa Aesar, or TCI, and were used without further purification unless otherwise indicated.

Unless otherwise indicated, the reactions set forth below were performed under a positive pressure of nitrogen or argon or with a drying tube in anhydrous solvents; the reaction flasks were fitted with rubber septa for the introduction of substrates and reagents via syringe; and glassware was oven dried and/or heat dried.

Unless otherwise indicated, column chromatography purification was conducted on a Biotage system (Manufacturer: Dyax Corporation) having a silica gel column or on a silica SepPak cartridge (Waters), or was conducted on a Teledyne Isco Combiflash purification system using prepacked silica gel cartridges.

$^{1}H$ NMR spectra and $^{13}C$ NMR were recorded on a Varian instrument operating at 400 MHz.

X-ray intensity data from a colorless plate-like crystal were measured at 173(2) K using a Bruker CCD diffractometer (Cu Kα radiation, λ=1.54178 A). Polarized light microscopic picture was captured at room temperature.

In the following examples, the abbreviations below may be used:

AcOH Acetic acid
ACN Acetonitrile
API Active pharmaceutical ingredient
Aq Aqueous
Brine Saturated aqueous sodium chloride solution
Bn Benzyl
BnBr Benzyl Bromide
$CH_2Cl_2$ Dichloromethane
DMA N,N-Dimethylacetamide
DMF N,N-Dimethylformamide
Dppf 1,1'-bis(diphenylphosphino)ferrocene
DBU 1,8-diazabicyclo[5.4.0]undec-7-ene
DIEA or DIPEA N,N-diisopropylethylamine
DMAP 4-N,N-dimethylaminopyridine
DMF N,N-dimethylformamide
DMSO Dimethyl sulfoxide
EtOAc Ethyl acetate
EtOH Ethanol
$Et_2O$ or ether Diethyl ether
g Grams
h or hr Hour
HATU O-(7-Azabenzotriazol-1-yl)-N,N,N',N'-tetramethyluronium hexafluorophosphate
HCl Hydrochloric acid
HPLC High-performance liquid chromatography
HPMCAS Hypromellose Acetate Succinate
IPA or i-PrOH 2-propanol or Isopropyl alcohol
mg Milligrams
mL Milliliters
Mmol Millimole
MeCN Acetonitrile
MeOH Methanol
Min Minutes
ms or MS Mass spectrum
$Na_2SO_4$ Sodium sulfate
PE petroleum ether
PPA Polyphosphoric acid
Rt Retention time
Rt or rt Room temperature
TBAF tetra-Butyl ammonium fluoride
TB SCl tert-Butyldimethylsilyl chloride
TFA Trifluoroacetic acid
THF Tetrahydrofuran
TLC thin layer chromatography
TMSCl Trimethylsilyl chloride
μL Microliters
XRPD X-ray particle diffraction

Example 1

Example 1A-Preparation of Compound 1 Crystalline Forms A

Step 1: Synthesis of INTQ-1

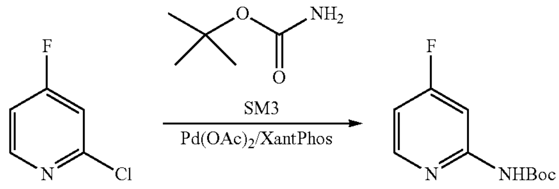

SM1 INTQ-1

1,4-Dioxane (1.5 volumes) was added to 2 L 4-necked round-bottom flask and the flask was evacuated and flushed three times with nitrogen. Then $Pd(OAc)_2$ (2 wt %, 0.50 kg) and XantPhos (9 wt %, 2.25 kg) was add into the flash, and the flask was evacuated and flushed three times with nitrogen. The mixture was stirred at room temperature for 0.5~1 hour under nitrogen atmosphere. NaOH (12.25 kg, 1.6 eq), $H_2O$ (1 volumes, 25 L) and 1,4-dioxane (8 volumes, 200 L) were charged into a 20 L reactor. The mixture was stirred until clear, and then SM3 (26.75 kg, 1.2 eq) was added into the mixture. The solution of the catalyst was transferred to the above reactor under nitrogen atmosphere. Then SM1 (25.00 kg, 1.0 eq) was dropwise added into the reactor. The system was heated to 65±5° C. and maintained at 65±5° C. for at least 5 hrs. HPLC was used to monitor the reaction until the content of SM1 was not more than 1.0%. The reaction mixture was cooled to 30±5° C., and then filtered and the cake was washed with 1,4-dioxane (1.0 volumes). $H_2O$ (4 volumes) was added into the filtrate and concentrated to 5 volumes. Then $H_2O$ (2 volumes) was added into the residue and concentrated to 5 volumes. The residue was cooled to room temperature and filtered. The cake was washed with $H_2O$ (2 volumes). Then the filter cake was slurried with IPA (2 volumes) at 25±5° C. for 3 hrs. The mixture was filtered and the filter cake was washed with IPA (0.5 volumes). The solid was dried in an oven under reduced pressure.

Steps 2&3: Synthesis of INTQ-3

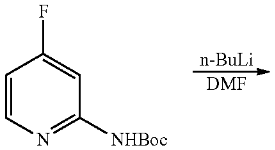

INTQ-1

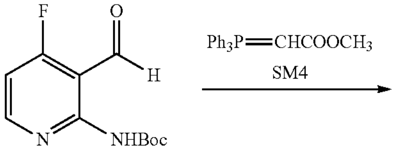

INTQ-2

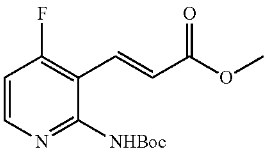

INTQ-3

THF (25 volumes), and INTQ-1 (16.00 kg, 1.0 eq) were charged into the reactor. The mixture was stirred and cooled to −80~−70° C. Then n-BuLi (n-hexane solution, 2.5M, 51.20 kg, 2.5 eq) was dropwise added into the mixture at −80~−70° C. The reaction was monitored by TLC after reacting for 1-2 hrs at −80~−70° C. Then DMF (9.92 kg, 1.8 eq) solution in THF (1.4 volumes) at −80~−70° C. was dropwise added into the reaction system. The reaction was monitored by TLC after reacting for 1-2 hrs at −80~−70° C. AcOH solution in THF (1.4 volumes) was dropwise added into the mixture to adjust the value of PH to 6-7 at −80~−70° C. Then TEA (8.00 kg, 1.05 eq) was charged into the reaction at −80~−70° C. The solution of methyl triphenylphosphoranylidene acetate (26.4 kg, 1.05 eq) in DCM (19 volumes) was dropwise added into the reaction mixture. The mixture was stirred for 10 hrs at −80~−70° C., then the reaction was monitored by TLC. $H_2O$ (10.5 volumes) and citric acid (32.00 kg, 2.1 eq) were charged into another reactor. The mixture was stirred to dissolve and cooled to 0-5° C. The temperature was cooled to −20° C. and the solution was transferred into the above 3 L 4-necked round-bottom flash. Then the mixture was stirred for 1 hour below 20° C. and the value of pH was confirmed to be between 4~7. The organic layer was separated and washed with 25% NaCl (17 volumes). Then the organic phase was concentrated to 5 volumes and EtOAc (17 volumes) was charged into the mixture and concentrated to 5 volumes. EtOAc (17 volumes) was charged into the mixture and concentrated to 5 volumes. The solution was used for the next step directly.

Step 4: Synthesis of INTQ-4

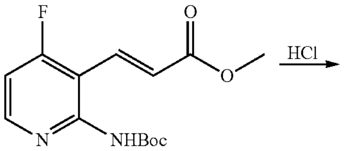

INTQ-3

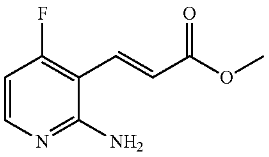

INTQ-4

The solution of INTQ-3 in EtOAc was charged into a reactor. The solution was stirred and cooled to −5~5° C. HCl was introduced into the mixture at −5~5° C. for 2 hrs. Then the mixture was heated to 20~30° C. HPLC was used to monitor the reaction every 2 hrs after reacting for 5 hrs until the content of INTQ-3 was less than 0.5%. The reaction mixture was concentrated to 10 volumes and cooled to 0~5° C. The residue was stirred for 1 hour at 0~5° C. The mixture was filtered and the filter cake was charged into $H_2O$ (15 volumes). The mixture was stirred for 2 hrs at 20~30° C. The mixture was filtered and the filter cake was washed with $H_2O$ (3 volumes). Then the filtrate was transferred to another reactor and $Na_2CO_3$ was charged into the mixture to adjust the value of PH to 8~9. Then the mixture was filtered and the filter cake was washed with $H_2O$ (4 volumes). 20.73 kg (Yield: 69.0%, Purity: 95.0%) of INTQ-4 was given after drying in the vacuum oven.

Step 5: Syntheses of INTQ-5

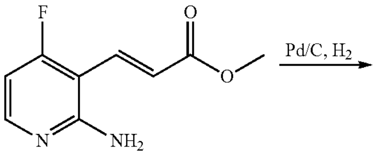

INTQ-4

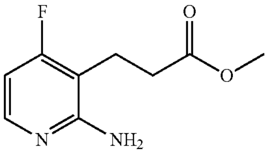

INTQ-5

INTQ-4 (10.40 kg, 1.0 eq), Pd/C (15% wt, 1.25 kg) and THF (11 volumes) were charged into a reactor. The mixture was stirred and heated to 30~35° C. Hydrogen was charged to a pressure of 10 atm. HPLC was used to monitor the reaction every 2 hrs after reacting for 15 hrs until the content of INTQ-4 was less than 0.5%. The reaction mixture was cooled to 20~30° C. and filtered through Celite (0.2 wt). The filter cake was washed with THF (2 volumes). The filtrate was concentrated to 3 volumes and EtOH (6 volumes) was added into the mixture. The solution was concentrated to 3 volumes and EtOH (6 volumes) was charged into the mixture. The mixture was concentrated to 3 volumes and used for the next step directly.

Step 6 Syntheses of BGB-INTQ-6

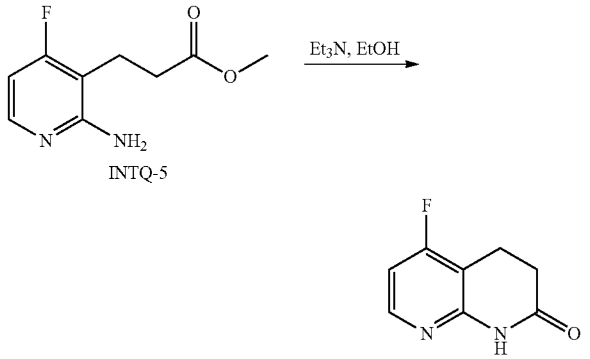

INTQ-5

INTQ-6

The solution of INTQ-5 (From the previous step) in EtOH (3 volumes), EtOH (7 volumes) and $Et_3N$ (22% wt, 2.29 kg) were charged into the rector. The solution was heated to 70~80° C. HPLC was used to monitor the reaction every 2 hrs after reacting for 15 hrs until the content of INTQ-5 is less than 1.0%. The reaction mixture was cooled to 30~40° C. and concentrated to 5 volumes. The mixture was cooled to −5~0° C. and stirred for 2 hrs. The mixture was filtered and the filter cake was washed with EtOH (1 volumes). 7.58 kg (Yield: 87.1%, Purity: 99.5%) of INTQ-6 was given after drying under oven at 45±5° C.

Step 7: Synthesis of INTQ-7

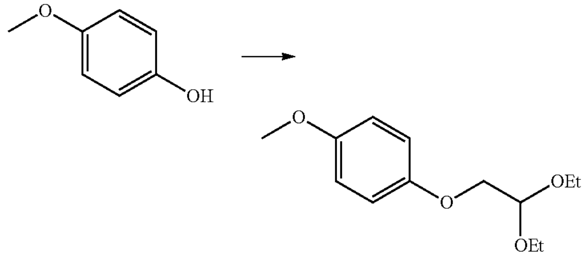

INTQ-7

Potassium hydroxide (49.9 Kg, 1.7 equiv) was added to a solution of 4-methoxyphenol (65 Kg, 1.0 equiv) in DMSO (65 L, 1 volumes). The system was heated to 120° C. Bromoacetaldehyde diethyl acetal (123.8 Kg, 1.2 equiv) was dropwise added while maintaining the temperature at 120~140° C. The reaction mixture was cooled to 20~40° C. after reaction completion as monitored by HPLC. N-heptane (2 volumes) and water (2 volumes) was charged to the reaction mixture. The mixture was filtered through Celite (0.2 wt) and the filter cake was washed with n-heptane (0.5 volumes). The filtrate was stood for at least 30 minutes. The organic layer was separated and the aqueous layer was extracted with n-heptane (2 volumes). The combined organic layer was washed with 2 N aqueous NaOH (2 volumes). The organic layer was washed with 15% aqueous NaCl (2 volumes) two times. The organic layer was concentrated to 3 volumes. Toluene (3 volumes) was added and continued to concentrate to 3 volumes. The toluene solution of INTQ-7 was used for next step directly.

Step 8: Synthesis of INTQ-8

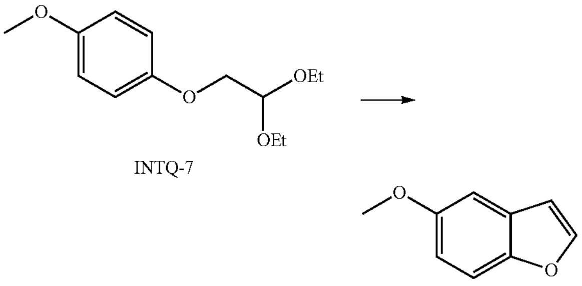

INTQ-7

INTQ-8

Amberlyst-15 (3.8 Kg, 0.1 wt) was added to toluene (760 L, 20 volumes). The system was heated to 110° C. under $N_2$ protection. The solution of INTQ-7 (38 Kg/Batch, 3 batches, 1.0 equiv) in toluene was dropwise added while maintaining the temperature at 105~110° C. The reaction system was concentrated under constant pressure at 105~110° C. to 17 volumes after reacting 1 hour. Toluene (3 volumes) was charged to the system. The reaction mixture was cooled to 20~40° C. after reaction completion as monitored by HPLC. The mixture was filtered through Celite (0.1 wt) and the filter cake was washed with toluene (0.5 volumes). The filtrate was washed with 2 N aqueous NaOH (2 volumes). The organic layer was washed with 20% aqueous NaCl (2 volumes) two times. The organic layer was concentrated to 2 volumes. The crude product was distilled below 110° C. to given INTQ-8 as off-white solid (43 Kg, Yield=61.2%, Purity≥98.0%.

Step 9: Synthesis of INTQ-9

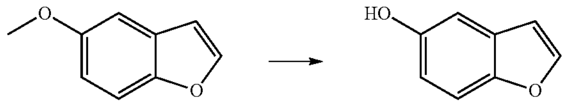

INTQ-8 INTQ-9

1-Dodecanethiol (147.0 Kg, 3.5 equiv) was added to a solution of INTQ-8 (43 Kg, 1.0 equiv) in NMP (260 L, 6 volumes). The system was heated to 75±5° C. Sodium ethoxide (69.0 Kg, 3.5 equiv) was added in portions while maintaining the temperature below 120° C. The reaction mixture was heated to 130±5° C. The mixture was sampled each hour for HPLC until the content of INTQ-8≤3.0% after reacting for 16 hours at 130±5° C. The reaction mixture was cooled to 60±5° C., and then 8 volumes water was charged to the mixture. The reaction mixture was cooled to 25±5° C., and then 3 volumes petroleum ether was charged to the mixture. The mixture was stirred for at least 30 minutes and stood for at least 30 minutes, separated. The organic phase was temporary storage. The aqueous phase was adjusted to pH=1~2 with 6 N HCl. The aqueous phase was extracted with 5 volumes and 3 volumes ethyl acetate, respectively. The residue aqueous was combined with the temporary organic phase, and then 4 volumes ethanol and 4 volumes petroleum ether were charged. The mixture was stirred for at least 30 minutes and stood for at least 30 minutes, and then separated. The aqueous phase was adjusted to pH=1~2 with 6 N HCl. The aqueous phase was extracted with 5 volumes ethyl acetate. The organic phase of ethyl acetate was combined and concentrated to 3 volumes under pressure below 50° C. 5 volumes n-heptane was charged to the residue and the mixture was adjusted to PH=9~10 with 5% NaOH. The mixture was stirred for at least 30 minutes and stood for at least 30 minutes, separated. The aqueous phase was adjusted to pH=1~2 with 6 N HCl. The aqueous phase was extracted with 5 volumes and 3 volumes ethyl acetate, respectively. Then the organic phases of ethyl acetate were combined and washed with 6 volumes 10% $H_2O_2$ and con. HCl (0.15 wt). Then the organic phase was washed with 6 volumes 5% $H_2O_2$ and con. HCl (0.15 wt). The organic layer was washed with 4 volumes 5% $Na_2SO_3$. The organic layer was washed with 3 volumes brine three times. The organic layer was concentrated to 3 volumes. Dichloromethane (5 volumes) was added and continued to concentrate to no obvious fraction. The crude product of INTQ-9 was used for next step directly.

Step 10: Synthesis of INTQ-10

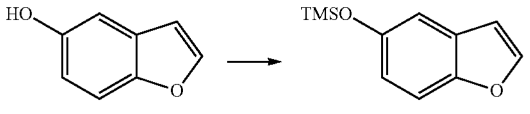

INTQ-9 INTQ-10

$Et_3N$ (48.2 Kg, 2.0 equiv) was added to the solution of INTQ-9 (32 Kg, 1.0 equiv) in dichloromethane (10 volumes) below 40° C. The mixture was cooled to −5±5° C. TMSCl (1.3 equiv) in dichloromethane (1 volumes) was dropwise added while maintaining the temperature at −5±5° C. The mixture was sampled each hour for gas chromatography until the content of INTQ-9≤2.0% after reacting for 1 hour at −5±5° C. The mixture was concentrated to 3 volumes under pressure below 40° C. 15 volumes of n-hexane was charged to the residue and the mixture was stirred for at least 30 minutes. The mixture was filtered and the filtrate was concentrated to no obvious fraction under pressure below 40° C. The crude product was distilled below 120° C. to given INTQ-10 as light yellow oil (40 Kg, Yield=81.4%, Purity≥97.5%).

Step 11: Synthesis of INTQ-11

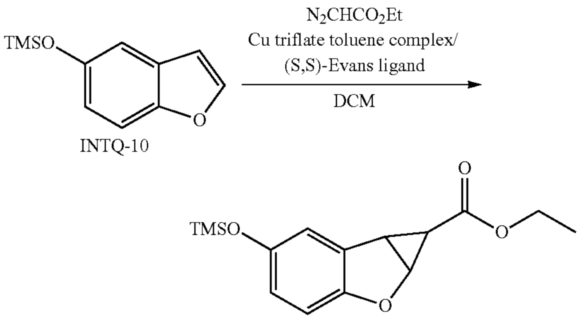

INTQ-10

INTQ-11

INTQ-10 (20 Kg/Batch, 2 batches, 1.0 eq) in dichloromethane (5 volumes) was slurried with CuI (0.1 wt) for 2~3 hours at 25±5° C. Copper (I) triflate (2:1 complex with toluene, 0.11% wt) and (S,S)-2,2-Bis (4-phenyl-2-oxazolin-2-yl)propane(0.15% wt) were stirred in dichloromethane (4 volumes) at 20~30° C. under $N_2$ atmosphere for 2~3 hours. The solution of INTQ-10 in dichloromethane was added through microspores filter, the solution of ethyl diazoacetate (2.0 eq) in dichloromethane (10 volumes) was dropwise added slowly in 15~25 hours at 20~30° C. The mixture was stirred for 30~60 minutes at 20~30° C., the mixture was washed with 4 volumes 0.05N aqueous disodium edetate dihydrate three times at 20~30° C. The organic section was washed with 3 volumes 25% aqueous NaCl two times. The organic section was concentrated under vacuum below 35° C. until the system was not more than 3 volumes. The crude product of INTQ-11 was used for next step directly.

Steps 12 &13: Synthesis of INTQ-13

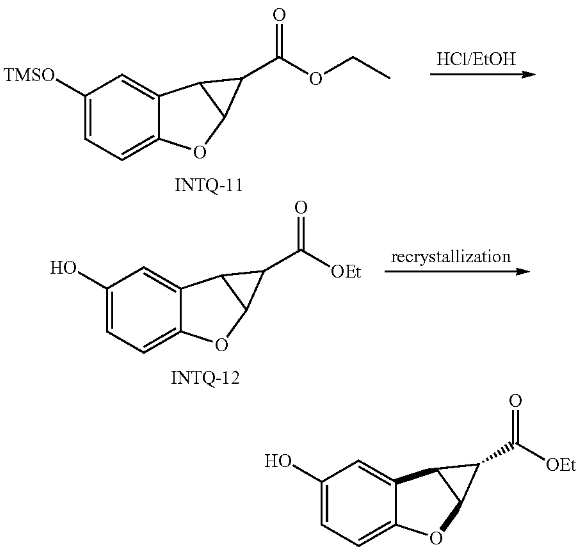

INTQ-11

INTQ-12

INTQ-13

Step 12: The crude product of INTQ-11 was dissolved in methanol (3 volumes), 38% HCl in EtOH (0.1 volumes) was added into the mixture and stirred 2~3 hours at 20~30° C. $Et_3N$ was dropwise added into the mixture to adjust PH=7. The mixture was concentrated under pressure to 2 volumes. Ethyl acetate (2 volumes) was charged and continued to concentrate under pressure to 2 volumes. N-heptane (2 volumes) was charged and continued to concentrate under pressure to 2 volumes. Dichloromethane (2 volumes) was charged for the material was dissolved completely. The residue was purified by silica gel chromatography (eluted with EtOAc:PE=1:5, about total 100 volumes) to give INTQ-12 as a yellow solid.

Step 13: INTQ-12 was charged to EtOAc (1.5 volumes) and n-heptane (20 volumes), the mixture was heated to 75~85° C. until to clear. The clear solution was stirred for 1 hour at 75~85° C. and then gradually cooled to 15~20° C. The mixture was filtered and washed with n-heptane (2 volumes) to afford the product. The wet product was dried at 55±5° C. for at least 16 hours to give INTQ-13 as light yellow to off-white solid.

Steps 14&15: Synthesis of INTQ-15

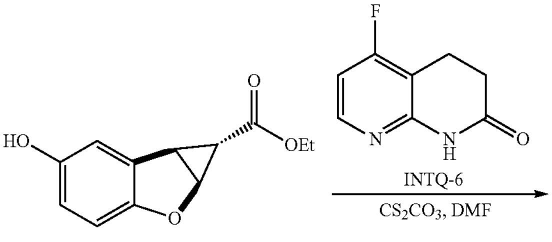

INTQ-13

-continued

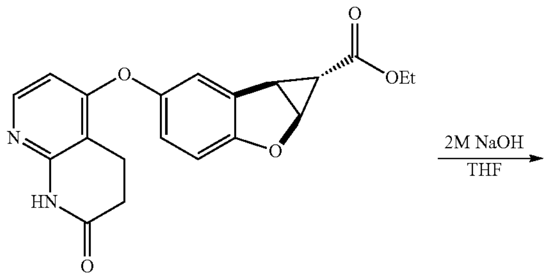

INTQ-14

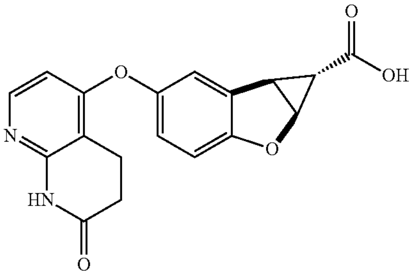

INTQ-15

Step 14: INTQ-13 (16 Kg, 1.0 equiv) and INTQ-6 (12.7 Kg, 1.05 equiv) were added to DMF (5 volumes). The system was heated to 55±5° C. Cesium carbonate (29.6 Kg, 1.25 equiv) was added. The reaction mixture was heated to 110±5° C. The mixture was sampled each hour for HPLC until the content of INTQ-13≤0.5% after reacting for 2 hours at 110±5° C. The reaction mixture was cooled to 30±5° C., and then adjusted to pH=6 with acetic acid (5 wt) at 30±5° C. Water (30 volumes) was added to the mixture at 25±5° C. The mixture was stirred for 1~2 hours and filtered to afford wet product. The wet product was re-slurry with water (5 volumes). The filter cake was used for next step directly.

Step 15: The wet product of INTQ-14 was added to mixture of 1 N NaOH(10 volumes) and THF (20 volumes). The system was stirred at 25±5° C. Sample each hour for HPLC until the content of INTQ-14≤0.5% after reacting for 4 hours at 25±5° C. The system was adjusted to pH=4~5 with 4 N HCl at 25±5° C. and stirred for 1 hour. The system was concentrated to 8 volumes under pressure below 50° C. and then filtered to afford wet product. The wet product was re-slurry with THF (10 volumes). The mixture was stirred for 1~2 hours and filtered to afford the wet product. The wet product was dried at 55±5° C. for at least 30 hours to give INTQ-15 as light brown to off-white solid.

Steps 16&17&18: Synthesis of INTQ-18

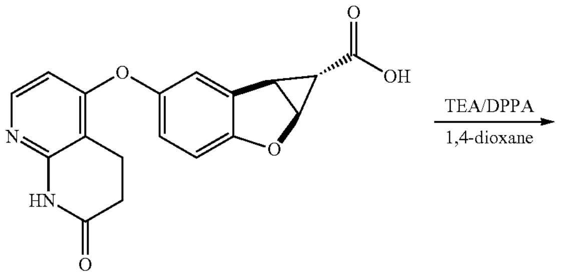

INTQ-15

-continued

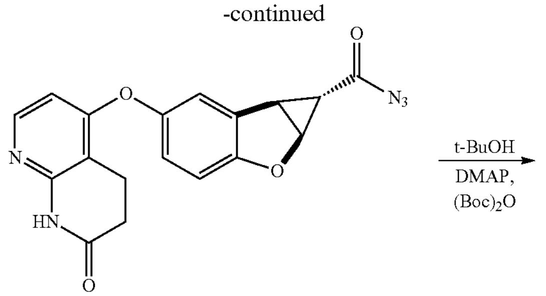

INTQ-16

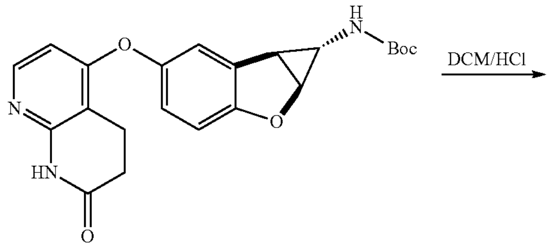

INTQ-17

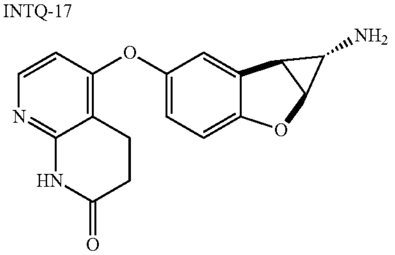

INTQ-18

A reactor was vacuumed to ≤−0.08 MPa and then charged with inert nitrogen to atmosphere. 1,4-dioxane (10.0 volumes), INTQ-15 (3.6 kg, 1.0 eq) were added to the reactor. The mixture was concentrated to 6.0-6.5 volumes below 50° C. and the mixture was sampled for the content of water. $Et_3N$ (1.1 eq) was charged to the reactor. The mixture was heated to 30±5° C., and DPPA (1.1 eq) was dropwise added into the reactor. The mixture was sampled for HPLC analysis after reacting 2 hours at 30±5° C. until the content of INTQ-15≤1.0%. The solution of INTQ-16 was obtained.

Another reactor was vacuumed to ≤−0.08 MPa and then charged with inert nitrogen to atmosphere. t-BuOH (20.0 volumes), $(Boc)_2O$ (0.5 eq), and DMAP (0.02 eq) were charged to the reactor. The mixture was heated to 85±5° C., stirred for at 2~3 hours and the mixture was sampled for the content of water. The criterion is KF≤0.01%. The solution of INTQ-16 was dropwise added into the above reactor of t-BuOH system at 85±5° C. (duration of at least 3 hours). The mixture was sampled for HPLC analysis after react 2 hours at 85±5° C. until the content of INTQ-16≤1.0%. The mixture was then cooled to less than 50° C., and concentrated to 3.0-4.0 volumes below 50° C.

DCM (10.0 volumes×2) was charged to the residue and the mixture was concentrated to 3.0-4.0 volumes below 50° C. DCM (10.0 volumes) was charged to the residue. Then 1 wt % NaOH aqueous (20.0 volumes) was charged to reactor and stir at 25±5° C. at least 1 hours. The mixture was filtered through Celite and then separated. The organic phase was washed with water (5.0 volumes) and separated. The organic phase was further washed with 25 wt % brine (5.0 volumes) and separated through silica gel to remove some impurities. The organic phase was concentrated to 6.0-7.0 volumes below 40° C. DCM was charged to 7.0 volumes. The mixture was then cooled to no more than 15° C., and hydrochloric acid (1.2 volumes) was added dropwise to the reactor at the temperature not more than 15° C. The mixture was sampled for HPLC analysis after reacted 3 hours at 15±5° C. until the content of INTQ-17≤4.0%. The mixture was heated to 25±5° C., water (3.0 volumes) was added to the reactor.

INTQ-16: $^1H$ NMR (400 MHz, DMSO-d6) δ 10.48 (s, 1H), 7.95 (d, J=5.6 Hz, 1H), 7.34 (d, J=2.4 Hz, 1H), 7.05 (d, J=8.4 Hz, 1H), 7.00 (dd, J=8.8, 2.4 Hz, 1H), 6.25 (d, J=5.6 Hz, 1H), 5.42 (d, J=5.2 Hz, 1H), 3.56 (dd, J=5.2, 2.8 Hz, 1H), 2.92 (t, J=7.6 Hz, 2H), 2.54 (d, J=8.0 Hz, 2H), 1.51 (d, J=3.2 Hz, 1H). MS: M/e 364 $(M+1)^+$.

INTQ-17: $^1H$ NMR (400 MHz, DMSO-d6) δ 10.49 (s, 1H), 7.94 (d, J=6.0 Hz, 1H), 7.34 (s, 1H), 7.18 (s, 1H), 6.96-6.83 (m, 2H), 6.22 (d, J=5.6 Hz, 1H), 4.86 (d, J=5.6 Hz, 1H), 2.92 (t, J=7.6 Hz, 2H), 2.86 (d, J=4.8 Hz, 1H), 2.54 (t, J=7.6 Hz, 2H), 2.12 (s, 1H), 1.39 (s, 9H). MS: M/e 410 $(M+1)^+$.

pH adjustment process: The solution of 4 wt % NaOH aq. was added dropwise into the reactor to adjust pH value to 2.7-3.1. If pH >3.1, hydrochloric acid (0.2 volume) was charged, then the solution of 4 wt % NaOH aq. was dropwise added into the reactor to adjust pH value to 2.7-3.1 (Precision pH test paper, range 2.7-4.7); the mixture was separate and the emulsion phase was collected as aqueous phase. The mixture was filtered through Celite, and the resulting aqueous phase was washed with DCM (2.0 volumes) once. Into the remaining aqueous phase in the reactor, DCM (6.0 volumes) and EtOH (5.0 volumes) were charged. 10.0 wt % $Na_2CO_3$ solution was added dropwise into the reaction to adjust the value of pH to 8-9 at 25±5° C. The mixture was stirred for 10-15 min and stood for 10-15 min. The mixture was separated and the aqueous phase was extracted with DCM (4.0 volumes) for 2 times. The organic phase was combined and washed with water (2.0 volumes), separated and the organic phase was washed with 25 wt % brine (5.0 volumes) once. The organic phase was concentrated to 3.0-4.0 volumes below 45° C., then n-heptane (4.0 volumes) was charged to the residual. The mixture was concentrated to 3.0-4.0 volumes below 45° C., and then n-heptane (4.0 volumes) was charged to the residual. The mixture was concentrated to 3.0-4.0 volumes below 45° C. The residual was cooled to 25±5° C., and then centrifuged and the solid was washed with n-heptane (2.0 volumes). The cake was transferred to a vacuum oven and the mixture was sampled for Loss on Drying (LOD) until LOD ≤1.0% after dry for 4 hours at 45±5° C. (box temperature). The purity of INTQ-18 (2.25 kg) was reported. The product was packaged in double LDPE plastic bags and stored at 2-30° C.

INTQ-18: $^1H$ NMR (400 MHz, DMSO-d6) δ 10.81 (s, 1H), 8.87 (s, 3H), 8.05 (d, J=6.0 Hz, 1H), 7.33 (t, J=1.2 Hz, 1H), 7.07-6.95 (m, 2H), 6.34 (d, J=6.0 Hz, 1H), 5.24 (d, J=6.0 Hz, 1H), 3.32 (dd, J=6.0, 2.0 Hz, 1H), 2.97 (t, J=7.6 Hz, 2H), 2.59 (t, J=7.6 Hz, 2H), 2.46 (s, 1H). MS: M/e 310 $(M+1)^+$.

Step 19: Synthesis of INTQ-19

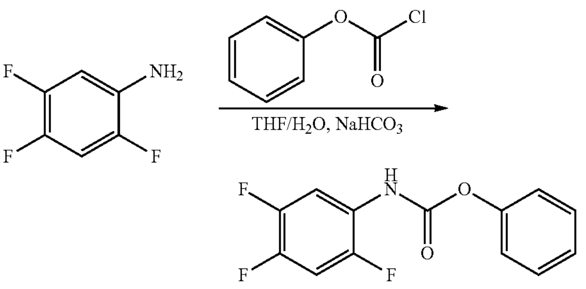

INTQ-19

The reactor was vacuumed to ≤−0.08 MPa and then charged with inert nitrogen to atmosphere. THF (6.0 volumes), $H_2O$ (3.0 volumes), 2,4,5-trifluoroaniline (1.0 eq), $NaHCO_3$ (1.2 eq) were charged to the reactor. The mixture was cooled to 0° C., phenyl chloroformate was added slowly at 0±5° C. The mixture was stirred for at least 2 hours. The mixture was sampled for LCMS until 2,4,5-trifluoroaniline ≤0.2%. EA (15.0 volumes) was then added. The organic phase was washed with $H_2O$ (5.0 volumes), and then washed with 5 wt % HCl aq. (5.0 volumes) for 2 times, washed with Sat. NaCl (5.0 volumes) for 2 times. The organic phase was concentrated to 10.0 volumes below 45° C. N-heptane (10.0 volumes) was charged to the residual. The mixture was concentrated to 10.0 volumes, and then n-heptane (10.0 volumes) was charged to the residual. The mixture was concentrated to 10.0 volumes and centrifuged and the solid was washed with n-heptane (2.0 volumes). The cake was sampled for LCMS analysis with the criterion of INTQ-19 >99%. The cake was then transferred to a vacuum oven and sampled for LOD until LOD ≤2.0% after dry for 10 hours at 35±5° C. (box temperature). The purity of INTQ-19 was reported. The product was packaged in double LDPE plastic bags and stored at 2-30° C.

INTQ-19: $^1H$ NMR (400 MHz, DMSO-d6) δ 10.20 (s, 1H), 7.82 (dt, J=12.0, 8.0 Hz, 1H), 7.66 (td, J=10.8, 7.6 Hz, 1H), 7.44 (t, J=7.6 Hz, 2H), 7.33-7.20 (m, 3H).

Step 20: Syntheses of Crystalline Form of Compound 1 (Form A)

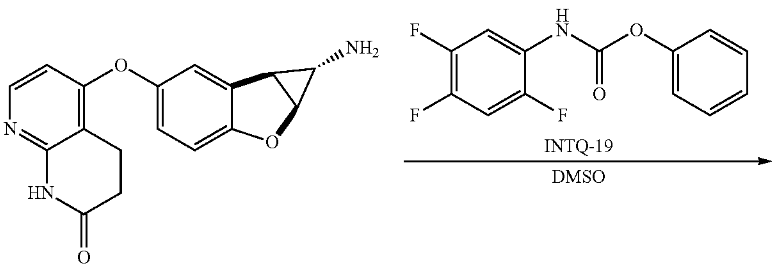

INTQ-18

-continued

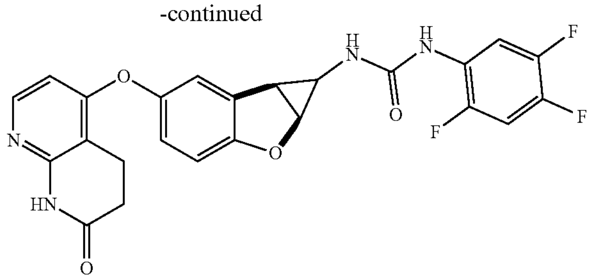

Compound 1 (Crystalline Form A)

The reactor was vacuumed to ≤−0.08 MPa and then charged with inert nitrogen to atmosphere. DMSO (9.0 volumes), INTQ-18 (1.63 kg, 1.0 eq) and N-methyl morpholine (1.0 eq) were charged to the reactor. The mixture was stirred for at least 0.5 hour at 20±5° C. INTQ-19 (1.27 kg, 0.9 eq) was charged to the reactor at 20±5° C. The mixture was sampled for HPLC analysis after reacting for 3 hours at 20±5° C. until the content of INTQ-19≤0.3%. After the completion of the reaction, the mixture of Compound 1 was dropwise added through microfilter into solution of 0.5% hydrochloric acid which was also filtered through a micron filter (30.0 volumes) slowly at 20±5° C. The mixture was stirred for at least 4 hours, and centrifuged. The filter cake was washed with purified water (5.0 volumes×2).

Slurry procedure: DMSO (9.0 volumes) and 0.5% hydrochloric acid were charged through a micron filter (30.0 volumes) to a reactor, and the filter cake was charged to the reactor and the mixture was stirred for at least 4 hours at 20±5° C., and then centrifuged. The filter cake was washed with purified water (5.0 volumes×2). The cake was sampled for HPLC analysis with the criterion of Compound 1 ≥98.0% If Compound 1<98.0%, "Slurry procedure" is repeated. Purified water (40.0 volumes) and filter cake were charged to a reactor, and the mixture was stirred for at least 4 hours at 20±5° C., and then centrifuged. The filter cake was washed with purified water (5.0 volumes×2). The cake was then dried under vacuum at 45±5° C. for at least 8 hours until LOD≤3.0%. If the solvent residue cannot meet the criteria, removal of residual solvent by slurry: purified water (40.0 volumes) and product were charged to a reactor, and the mixture was stirred for at least 4 hours at 20±5° C., and then centrifuged. The filter cake was washed with purified water (5.0 volumes×2). The cake was dried under vacuum at 45±5° C. for at least 8 hours until LOD≤3.0%. The cakes were sampled for solvent residue. If solvent residue cannot meet criteria, the procedure "removal of residual solvent by slurry" is repeated until solvent residue meets the criterion. The material was sampled for HPLC analysis with the criterion of Compound 1 ≥98.0% purity (2.02 kg) and the criterion of impurity-1 less than 0.5%. HPLC analysis determined that the content of Impurity-1 was less than 0.1% herein. The product was packaged in double LDPE bags with desiccant, stored at room temperature.

Compound 1: $^1$H NMR (400 MHz, DMSO-d6) δ 10.47 (s, 1H), 8.54 (s, 1H), 8.23-8.07 (m, 1H), 7.96 (d, J=5.6 Hz, 1H), 7.65-7.51 (m, 1H), 7.23 (s, 1H), 7.01 (d, J=2.0 Hz, 1H), 6.96-6.87 (m, 2H), 6.25 (d, J=5.6 Hz, 1H), 4.98 (d, J=6.0 Hz, 1H), 2.97 (dd, J=5.6, 1.6 Hz, 1H), 2.93 (t, J=7.6 Hz, 2H), 2.54 (t, J=7.6 Hz, 2H), 2.26 (s, 1H).

Figure 16:
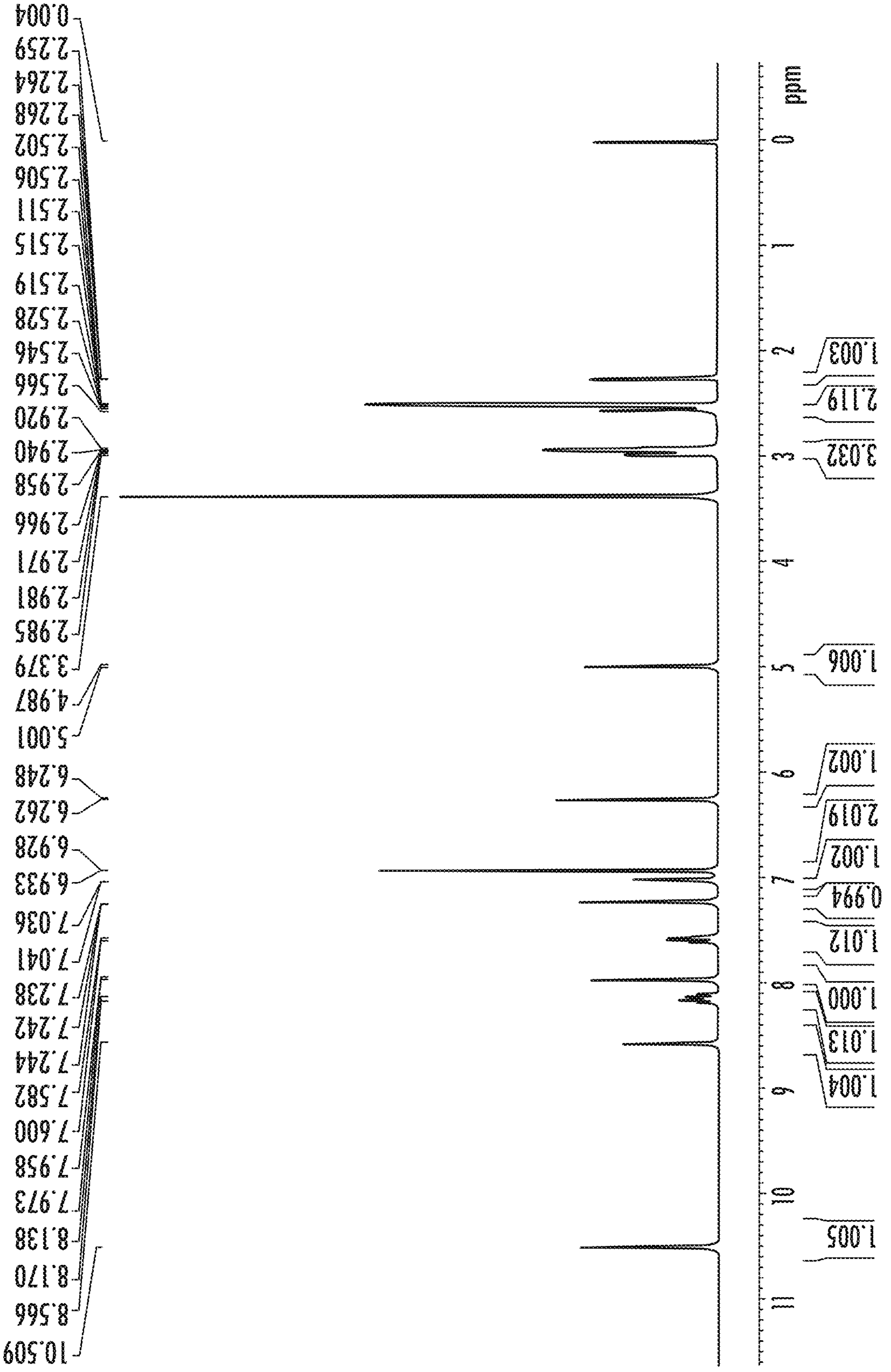
FIG. 16 shows a $^{1}$H-NMR spectrum of crystalline form of Compound 1 (Form A).
Figure 17:
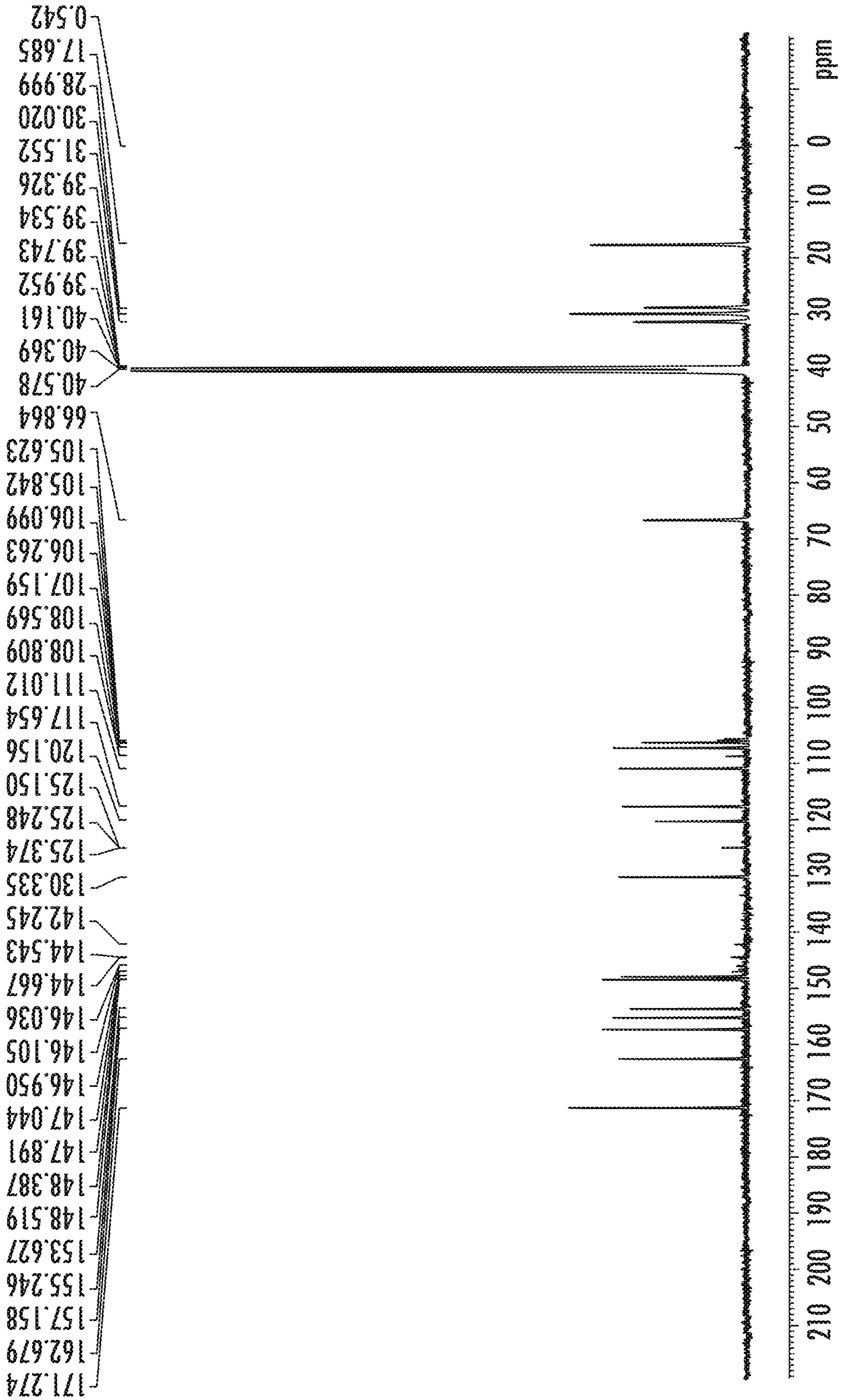
FIG. 17 shows a $^{13}$C-NMR spectrum of crystalline form of Compound 1 (Form A).

The resulting powder prepared in Example 1 was evaluated to amorphous or crystalline nature by the X-ray powder diffraction (XRPD) pattern technique. The resulting powder prepared in Example 1 was determined to be crystalline (sometimes referred to as "Form A" throughout the application) as evidenced by the crystalline peaks in the XRPD pattern in FIG. 1. The resulting power was also characterized by $^1$H-NMR spectra and $^{13}$C-NMR spectra, as shown FIG. 16 and FIG. 17, respectively.

The XRPD Pattern of the crystalline form of Compound 1 (Form A) has the following characteristic peak diffraction angles (where "spacing" is shown as the "d-value" in FIG. 1):

TABLE 1

XRPD Pattern of Crystalline Form of Compound 1 (Form A)

| Peak # | Diffraction angle (2-theta) | Spacing | Relative intensity |
|---|---|---|---|
| 1 | 4.709 | 18.75067 | 17.7 |
| 2 | 9.364 | 9.43727 | 95.9 |
| 3 | 10.189 | 8.6743 | 8.4 |
| 4 | 13.636 | 6.48883 | 23.4 |
| 5 | 14.042 | 6.30209 | 100 |
| 6 | 14.884 | 5.94706 | 44.6 |
| 7 | 15.59 | 5.67936 | 26.3 |
| 8 | 17.226 | 5.14372 | 11.8 |
| 9 | 17.417 | 5.08759 | 12.1 |
| 10 | 18.747 | 4.72958 | 21.3 |
| 11 | 19.966 | 4.44356 | 20.2 |
| 12 | 20.396 | 4.35075 | 22.9 |
| 13 | 21.176 | 4.1922 | 67.1 |
| 14 | 22.311 | 3.98139 | 27.9 |
| 15 | 24.346 | 3.65307 | 59.1 |
| 16 | 24.665 | 3.60654 | 51.5 |
| 17 | 25.071 | 3.54907 | 43.5 |
| 18 | 25.492 | 3.49136 | 32.1 |
| 19 | 26.756 | 3.32928 | 17.2 |
| 20 | 27.347 | 3.25857 | 19.1 |
| 21 | 27.77 | 3.20988 | 18.1 |
| 22 | 28.584 | 3.12038 | 18 |
| 23 | 29.081 | 3.06817 | 44.4 |
| 24 | 30.199 | 2.95703 | 22.2 |
| 25 | 31.826 | 2.80946 | 12 |
| 26 | 31.992 | 2.79533 | 10.3 |
| 27 | 33.119 | 2.70273 | 8.8 |
| 28 | 34.099 | 2.62723 | 11.3 |
| 29 | 34.61 | 2.58964 | 13.1 |

Long-Term Stability of Form A

The long-term stability studies of Form A showed there was no significant chemical purity change occurred when stored at 25° C.° C./60% RH for up to 24 months (total impurities: T0=1.0% and T24=1.0%) and at 40° C./75% RH condition for up to 6 months (total impurities: T0=1.0% and T6=1.0%). In addition, no optical purity changes were observed when stored at 25° C.° C./60% RH for up to 24 months and at 40° C./75% RH condition for up to 6 months. The XRPD data of the testing sample showed that Form A was stable at 6 months at 40° C./75% RH condition and Form A was also stable at 6 months at 25° C./60% RH condition but changed to the crystalline form (sometimes referred to as "Form A*") at 12 months.

The XRPD pattern of Form A* is shown FIG. 2. The XRPD pattern of Form A* has the following characteristic peak diffraction angles (where "spacing" is shown as the "d-value" in FIG. 2):

TABLE 2

XRPD Pattern of another crystalline form of Compound 1 (Form A*)

| Peak# | Diffraction angle (2-theta) | Spacing | Relative intensity |
|---|---|---|---|
| 1 | 9.21 | 9.59050 | 76.3% |
| 2 | 10.76 | 8.21514 | 2.4% |
| 3 | 12.26 | 7.21638 | 1.3% |
| 4 | 13.95 | 6.34232 | 100.0% |
| 5 | 15.37 | 5.75948 | 41.0% |
| 6 | 16.46 | 5.38091 | 3.2% |
| 7 | 18.14 | 4.88565 | 6.1% |
| 8 | 18.72 | 4.73555 | 17.7% |
| 9 | 19.29 | 4.59811 | 8.6% |
| 10 | 19.79 | 4.48301 | 9.9% |
| 11 | 20.53 | 4.32170 | 41.1% |
| 12 | 21.64 | 4.10256 | 5.7% |
| 13 | 22.31 | 3.98220 | 5.8% |
| 14 | 23.17 | 3.83593 | 1.8% |
| 15 | 23.97 | 3.70913 | 30.0% |
| 16 | 24.93 | 3.56837 | 30.0% |
| 17 | 26.69 | 3.33777 | 3.9% |
| 18 | 27.80 | 3.20666 | 2.7% |
| 19 | 28.72 | 3.10596 | 14.7% |
| 20 | 29.37 | 3.03820 | 14.9% |
| 21 | 30.92 | 2.88941 | 2.2% |
| 22 | 33.23 | 2.69417 | 1.9% |
| 23 | 37.87 | 2.37384 | 1.1% |
| 24 | 38.15 | 2.35726 | 1.1% |

The stability studies showed that Form A is chemically stable and can be stored for over 12 months without obvious decomposition.

Hygroscopicity of Form A was also assessed via dynamic vapor sorption (DVS) as shown in FIG. 19. FIG. 19 shows that Form A is moderately hygroscopic with the weight gain of 4.96% at 80% RH.

As will be discussed in the preclinical study below, the oral absorption of Form A was relatively poor in rats with a bioavailability of 21%, partially due to the low solubility of Form A (which was found to be less than 0.1 μg/mL in water).

Due to the low bioavailability observed in preclinical study, Form A therefore has limited use for direct pharmaceutical formulation. However, Form A is a good candidate for purifying API and used as the starting materials for manufacturing the amorphous solid dispersion due to the above-mentioned long-term stability of Form A (i.e., no significant chemical purity change occurred when stored at 25° C.° C./60% RH for up to 24 months and no optical purity changes were observed when stored at 25° C.° C./60% RH for up to 24 months and at 40° C./75% RH condition for up to 6 months). Although the change of the crystalline form (i.e., from Form A to Form A*) has been observed at 12 months at the above-mentioned condition, the long-term storage (i.e., 24 months) had no impact for the later amorphous MBP manufacture because Compound 1 is dissolved in DMA anyway before co-precipitation occurs.

The physicochemical properties of Form A prepared in Example 1 is summarized in Table 3.

TABLE 3

The main physicochemical properties of Form A

| | |
|---|---|
| Properties | White to off-white solid |
| Solubility* | The solubility in 0.1N HCl and pH 1.2 buffer solutions are 0.02 mg/mL and 0.015 mg/mL, respectively, while the solubility in water, pH 4.5 buffer solution, pH 6.8 buffer solution, pH 7.4 buffer solution, 5% Pluronic F68, and n-heptane is less than 0.1 μg/mL. Surfactants have found to improve the solubility to some extent, especially sodium lauryl sulfate (SLS) and hexadecyl trimethyl ammonium bromide (HTAB), 5% SLS and 5% HTAB increased the solubility to 1 mg/mL and 0.96 mg/mL. 20% hydroxypropyl-β-cyclodextrin (referred to as HP-β-CD) can increase the solubility of Form A up to 0.55 mg/mL. The solubility in 20% sulfobutyl ether-β-cyclodextrin (abbreviated as SBE-β-CD) is 0.55 mg/mL. In both DMSO and DMA, the sample of Form A was completely dissolved within 2 hours, with concentrations greater than 95.42 mg/mL (DMSO) and 371.83 mg/mL (DMA), respectively. |
| Hygroscopicity | The DVS results show that Form A is moderately hygroscopic with a sample weight gain of 4.96% at 80% relative humidity. |
| Thermogravimetric Analysis (TGA) and Differential Scanning Calorimetry (DSC) | The TGA results show that there is a total of 2.23% weight loss (two weight losses, 1.482% and 0.7509%, respectively) before sample decomposition. The DSC plot shows multiple thermal events. |
| | XRPD (XRPD): Compound 1 Crystal Form A has unique diffraction peaks. |
| Particle size distribution | D90 = 62.382 μm |

*The procedure of measuring solubility: About 5 mg of drug substance is weighed into 4 mL sample vials and then 1 mL of water, 0.1N HCl solution and buffers (pH 1.2, pH 4.5, pH 6.8 and pH 7.4) are added, respectively. The samples are placed into shaker and are kept shaking with the rate of 200 rpm at 25° C. At 2 and 24 hours, the samples are filtered and diluted to appropriate concentrations. The solubility of the drug substance is then analyzed by HPLC.

Example 1B

The intermediate INTQ-20 was synthesized in a similar manner to Example 1A, step 19, and then subjected to a condensation reaction with the intermediate INTQ-18 to obtain Compound 1.

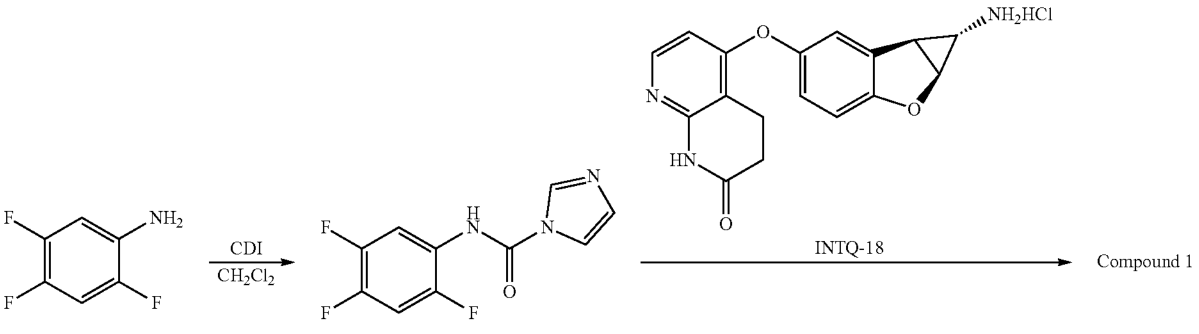

INTQ-20

However, INTQ-20 is unstable and most of the products comprising INTQ-20 are by-product Impurity-2, and Impurity-3 (possibly due to the reaction of the methanol used in the LCMS mobile phase for separating the intermediate INTQ-20).

Impurity-2

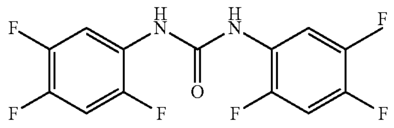

Impurity-3

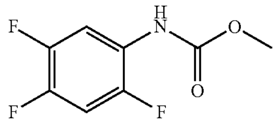

Although the synthesis route was optimized, that is, the intermediate INTQ-20 reaction solution and the intermediate INTQ-18 were directly subjected to one-pot reaction, the product still contained a large amount of Impurity-2.

Example 1C

The intermediate INTQ-21 was synthesized in a similar manner to Example 1A, step 19, and then subjected to a condensation reaction with the intermediate INTQ-18 to obtain Compound 1.

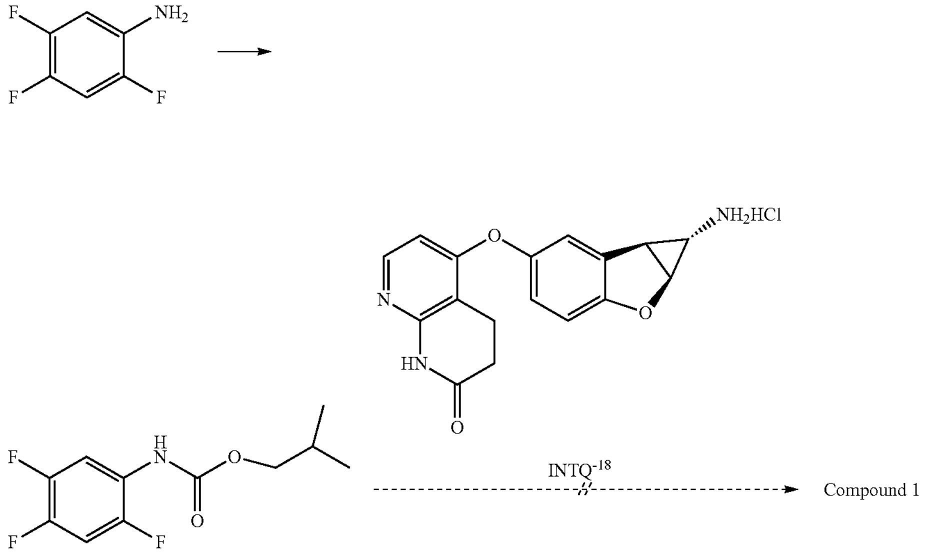

INTQ-21

However, the formation of Compound 1 was not detected at room temperature when the intermediate INTQ-21 was subjected to a condensation reaction with the intermediate INTQ-18; no Compound 1 was found even the reaction was carried out at the temperature of 100° C.

Example 1D

The intermediate INTQ-22 was synthesized in a similar manner to Example 1A, step 19, and then subjected to a condensation reaction with the intermediate INTQ-18 to obtain Compound 1.

TABLE 4

| Single Crystal Data and Structure Refinement of Form A** | |
|---|---|
| Identification code | 810323-07-A4 |
| Empirical formula | $C_{34}H_{17}F_3N_4O_4 \cdot C_4H_8O_2$ |
| Formula weight | 570.52 |
| Temperature | 119.97 K |
| Wavelength | Cu/Kα (λ = 1.54178 Å) |
| Crystal system, space group | Monoclinic, $P2_1$ |
| Unit cell dimensions | a = 8.7232(5) Å<br>b = 12.9311(7) Å<br>c = 24.0303(14) Å<br>α = 90°<br>β = 99.513(2)°<br>γ = 90° |
| Volume | 2673.4(3) $Å^3$ |
| Z, Calculated density | 4, 1.417 $g/cm^3$ |
| Absorption coefficient | 0.979 $mm^{-1}$ |
| F(000) | 1184.0 |
| Crystal size | 0.35 × 0.25 × 0.03 $mm^3$ |
| 2 Theta range for data collection | 7.788° to 133.368° |
| Limiting indices | −9 ≤ h ≤ 10<br>−14 ≤ k ≤ 15<br>−26 ≤ l ≤ 28 |
| Reflections collected/ Independent reflections | 38790/8431 [$R_{int}$ = 0.0573, $R_{sigma}$ = 0.0439] |
| Completeness | 88.85% |
| Refinement method | Full-matrix least-squares on $F^2$ |
| Data/restraints/parameters | 8431/61/741 |
| Goodness-of-fit on $F^2$ | 1.032 |
| Final R indices [I ≥ 2sigma(I)] | $R_1$ = 0.0883, $wR_2$ = 0.2419 |
| Final R indices [all data] | $R_1$ = 0.1064, $wR_2$ = 0.2610 |
| Largest diff. peak and hole | 0.89/−0.51 e · $Å^{-3}$ |
| Flack parameter | −0.03(7) |
| Bayesian statistics on Bijvoet differences[1] | Hooft y = −0.01(6), P2(true) = 1.000. P3(true) = 1.000, P3(rac-twin) = 0.3E−15, P3(false) = 0.5E−59, corr.coeff = 0.999 |

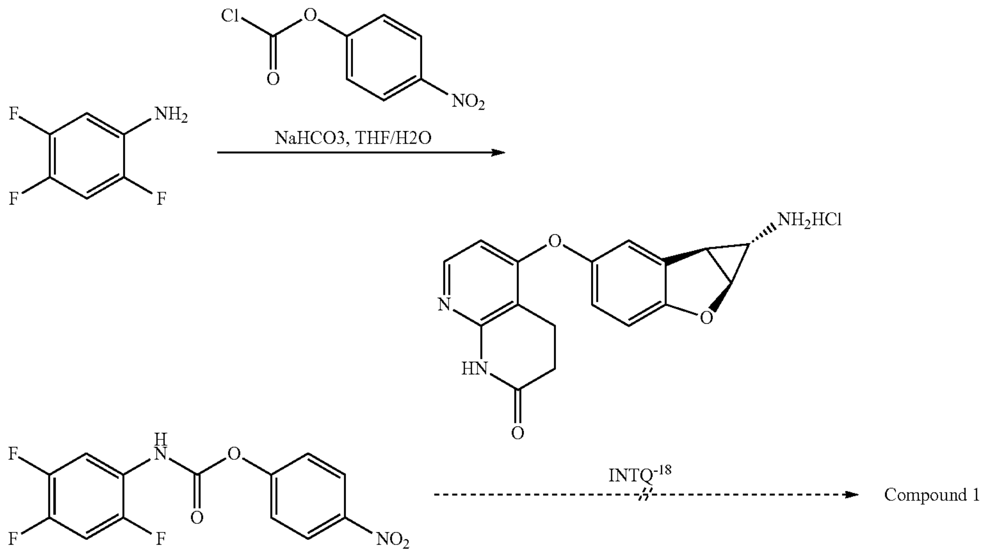

INTQ-22

However, INTQ-22 was not successfully isolated from the synthesis of the intermediate INTQ-22. The isolated products are mainly Impurity-2 (possibly due to the reason that the p-nitrophenol group can easily be removed so that Impurity-2 can easily be formed from the active ester and other trifluoroaniline molecule) and p-nitrophenol.

Example 2

Single Crystal of Compound 1 (Form A**)

The plate-shaped single crystals of Compound 1 EtOAc solvate used for single crystal X-ray diffractometry characterization were crystallized from EtOAc solvent by slow evaporation. The experimental details are elaborated below. First, 1.8 mg Compound 1 was weighed into a 3-mL glass vial with the addition of 0.5 mL EtOAc solvent. After being oscillated on a vortex and ultrasonically shaken to accelerate dissolution, the suspension was filtered through PTFE filter membrane (0.45 μM) and the filtrate was transferred to a clean 4-mL shell vial (44.6 mm×14.65 mm). Subsequently, the shell vial was sealed by the PE-Plug with one pinhole on it and placed in the fume hood for slow evaporation at ambient temperature and humidity. After six days, plate-shaped crystal sample (CP ID: 810323-A4) was obtained.

The structure of the plate-shaped crystal was determined using a set of diffraction data collected from a single crystal grown by slow cooling in EtOAc and was referred to as single crystal of Compound 1 or Form A. Crystal data and structure refinement of Form A are listed in FIG. 3-6.

Figure 3:
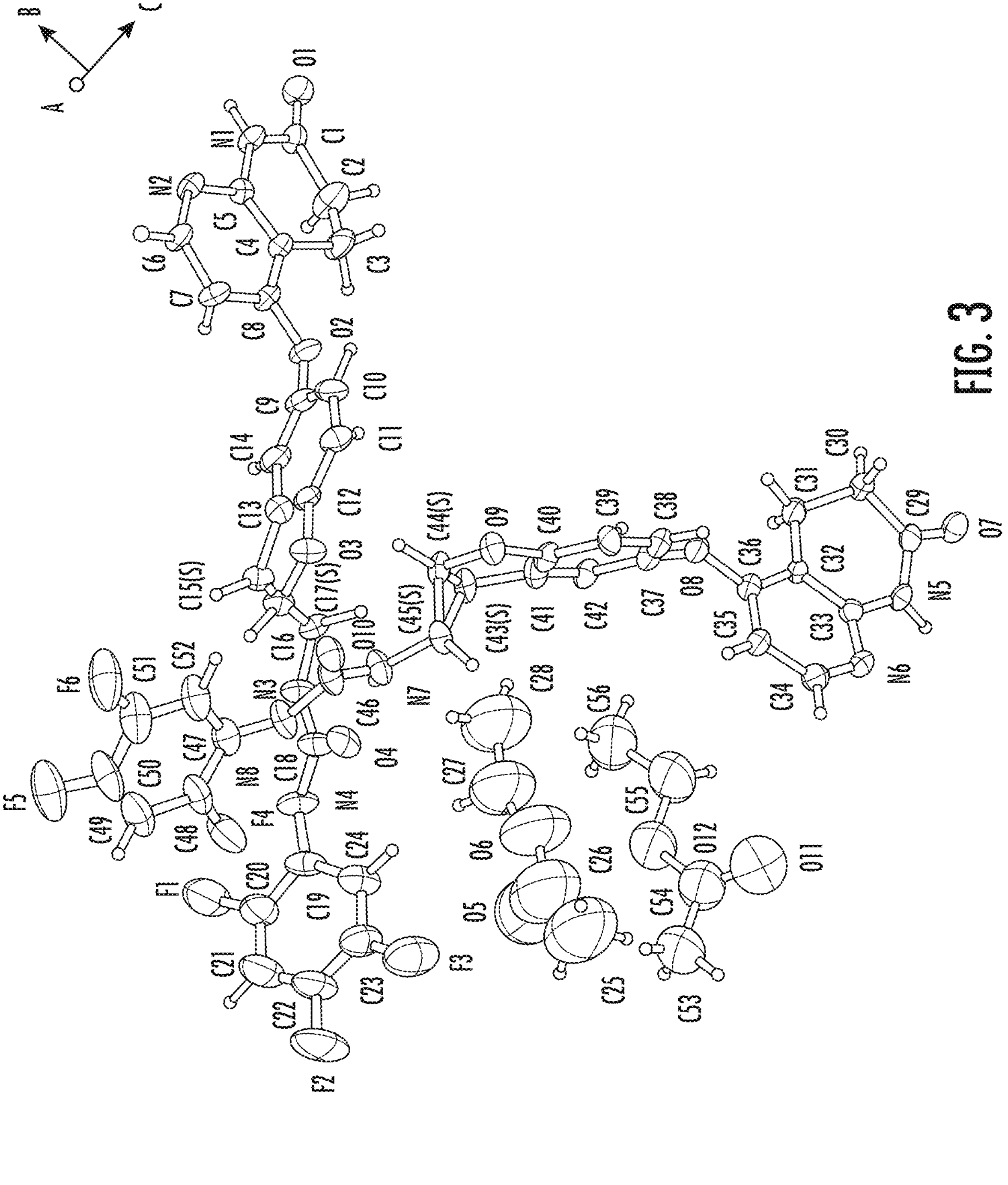
FIG. 3 shows the absolute structure of single crystalline of Compound 1 (Form A**) (single crystals obtained by crystallization from ethyl acetate/heptane).
Figure 4:
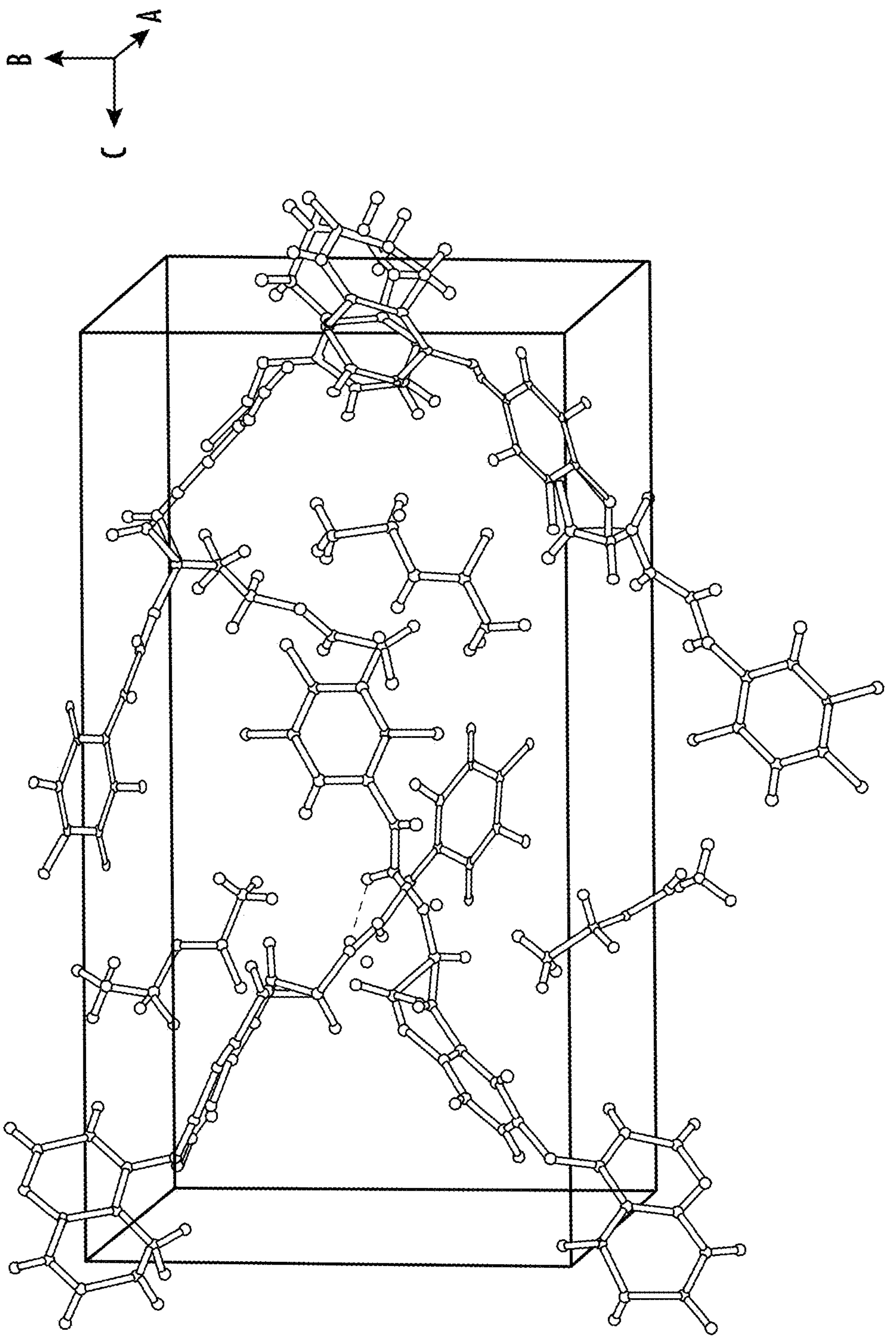
FIG. 4 shows a Crystal Packing of single crystalline of Compound 1 (Form A**).
Figure 5:
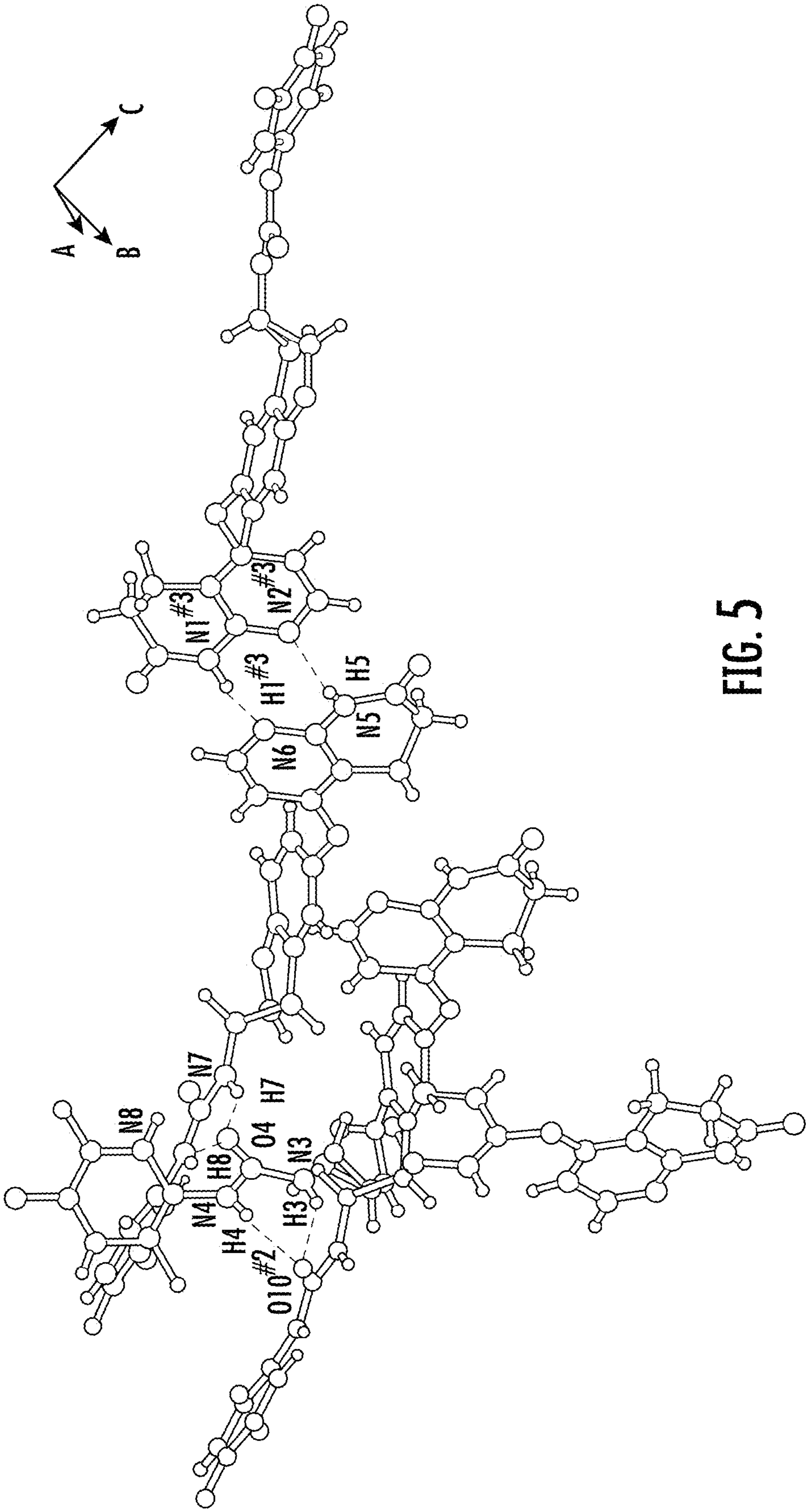
FIG. 5 illustrates hydrogen bonds of single crystalline of Compound 1 (Form A**).

As shown in FIG. 3, the asymmetric unit of the single structure is comprised of two independent Compound 1 molecules and two EtOAc solvent molecules, indicating the crystal is EtOAc solvate of Compound 1. The single crystal structure determination confirmed the absolute configuration of Compound 1 as {C15(S), C16(S), C17(S)}, when taking Compound 1 molecule as example. The unit cell of the single crystal is comprised of four Compound 1 molecules and four EtOAc solvent molecules, as shown in FIG. 4. The potential classic H-bonds in the single crystal structure is shown in FIG. 5. Theoretical XRPD pattern of single crystalline form of Compound 1 (i.e., Form A) calculated using the MERCURY software is shown in FIG. 6**.

Example 3

Preparation of Neat Amorphous Form of Compound 1 (Form B)

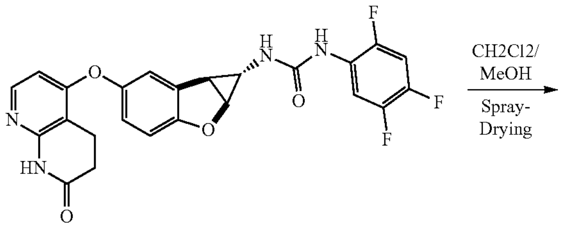

Compound 1 (Crystalline Form A)

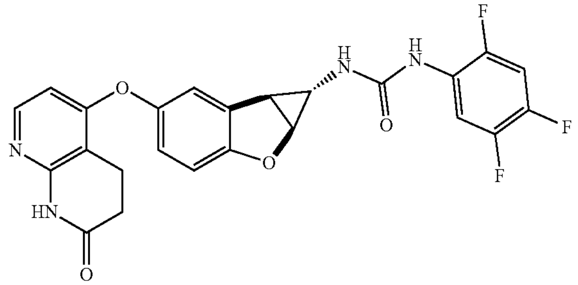

Compound 1 (Neat Amorphous Form B)

A solution of Form A of Compound 1 in DCM/MeOH (2:1) was spray-dried to give a white powder. The conditions of spray drying were as follows: A solution of Form A (2.0 g) of Compound 1 in 100 mL of a mixed solvent (DCM/MeOH=2:1 by volume) was sprayed by a spray dryer (BUCHI-290 & BUCHI-295). The powder of the product was dried by infrared lamp at 50° C. for 16 hours. 1.06 g powder was obtained. The operating parameters of the spray dryer (BUCHI-290 & BUCHI-295) were as follows: inlet temperature: 60° C.; outlet temperature: 35° C., Aspirator: 100%; pump %: 15%; nozzle cleaner: 2.

Figure 29:
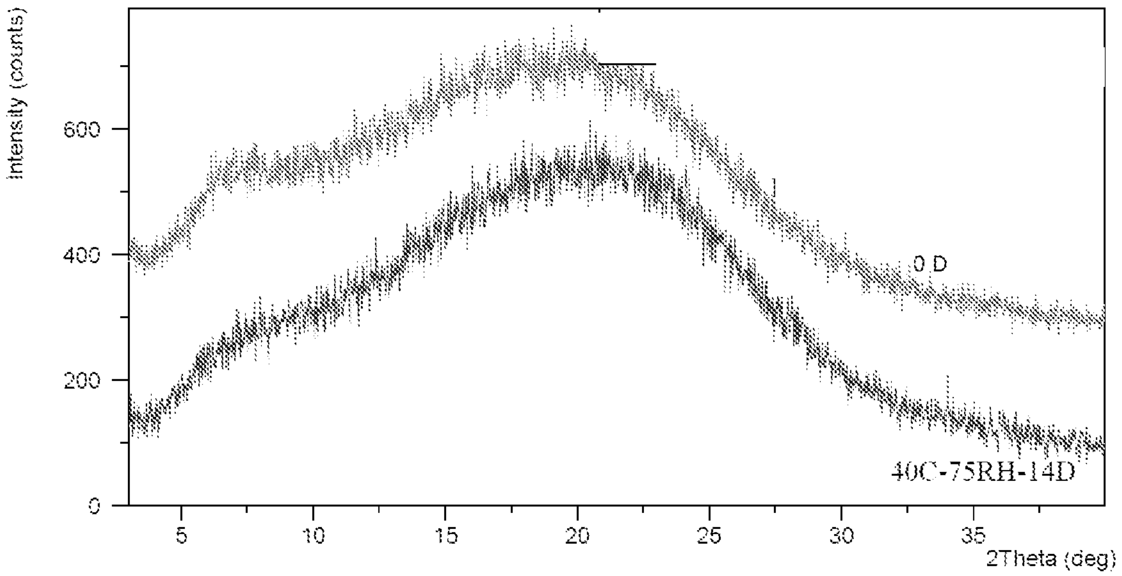
FIG. 29 shows XRPD overlay of neat amorphous form of Compound 1 (Form B)

The XRPD pattern method was used to characterize the structure of the resulting powder, which was confirmed to be amorphous, as FIG. 7 has no any peak diffraction angles. The amorphous form of Compound 1 is referred to as Neat Amorphous Form of Compound 1 or Form B throughout the application. $^1$H-NMR spectra for Form B is shown in FIG. 21. Form B was determined as having a glass transition temperature of 138.3° C. The sample was a white powder with particle sizes of D90=69.9 μm, D50=3.5 μm, D10=1.4 μm. The XRPD data of the testing sample showed that Form B was stable at 14 days at 40° C./75% RH condition as the XRPD pattern data of the testing sample at 14 days in FIG. 29 did not show any crystalline peaks.

Although the neat amorphous form of Compound 1 was found to have a relatively high bioavailability compared with the crystalline form (i.e. Form A), the long-term stability of Form Bis not certain.

Throughout the specification of the present application, HPMCAS-LF, HPMCAS-MF and HPMCAS-HF are commercially available from Shin-Etsu Chemical Co. Ltd unless indicated otherwise.

Example 4

Preparation of Amorphous Solid Dispersion of Compound 1 (Form C)

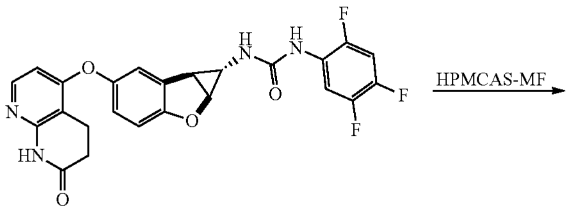

Compound 1

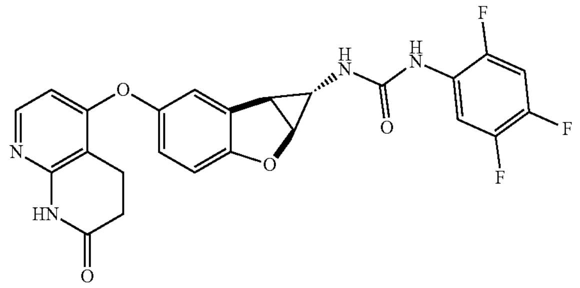

(HPMCAS-MF)m
Formula I

The amorphous solid dispersion of Compound 1 as micro-precipitation bulk powder was prepared as follows: Form A of Compound 1 as a poorly soluble drug and Hypromellose acetate succinate (HPMCAS-MF) in a ratio of 3:7 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the resulting solid was washed a few times with 0.01 N HCl solution and water, and then dried under vacuum at below 50° C. to give a microprecipitation bulk powder suitable for drug product manufacture.

Figure 8:
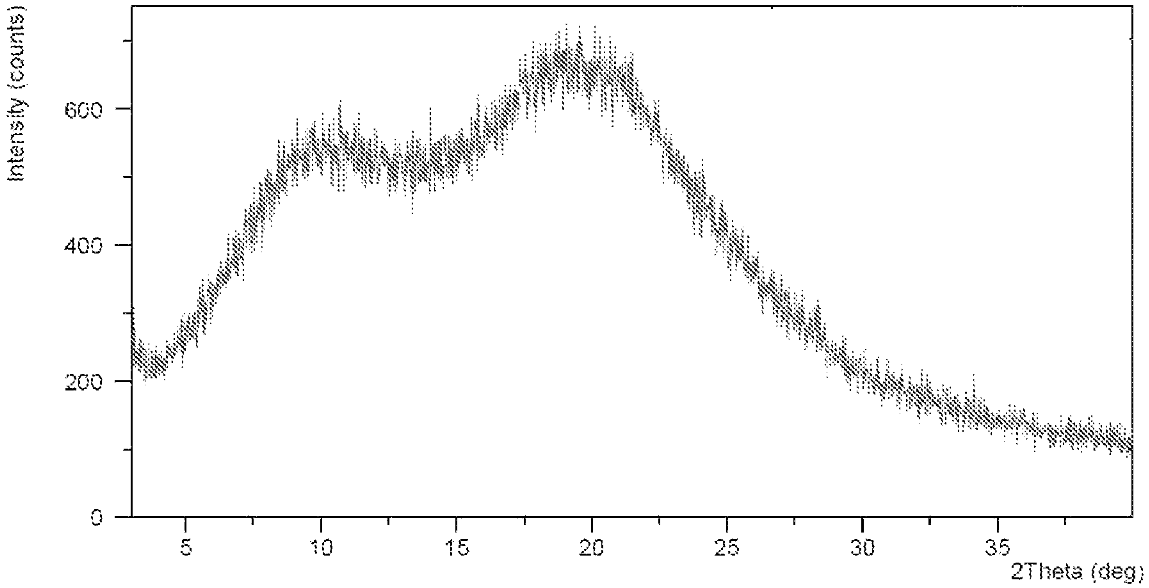
FIG. 8 shows an XRPD pattern of amorphous solid dispersion of Compound 1 as MBP (Form C) from 3:7 ratio of Compound 1:HPMCAS-MF.
Figure 22:
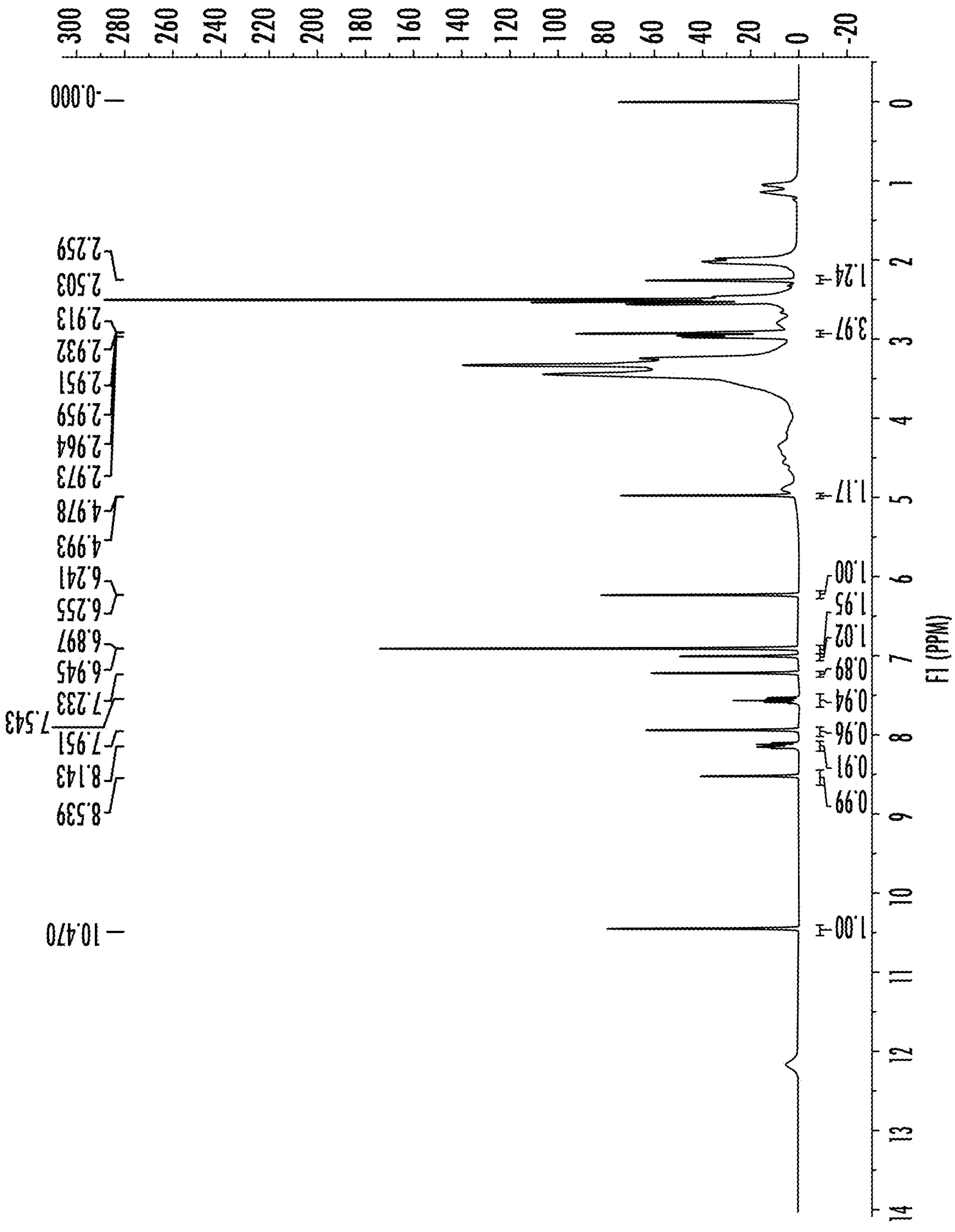
FIG. 22 shows a $^{1}$H-NMR spectrum of amorphous solid dispersion of Compound 1 as MBP (Form C) (Compound 1:MF=3:7)
Figure 30:
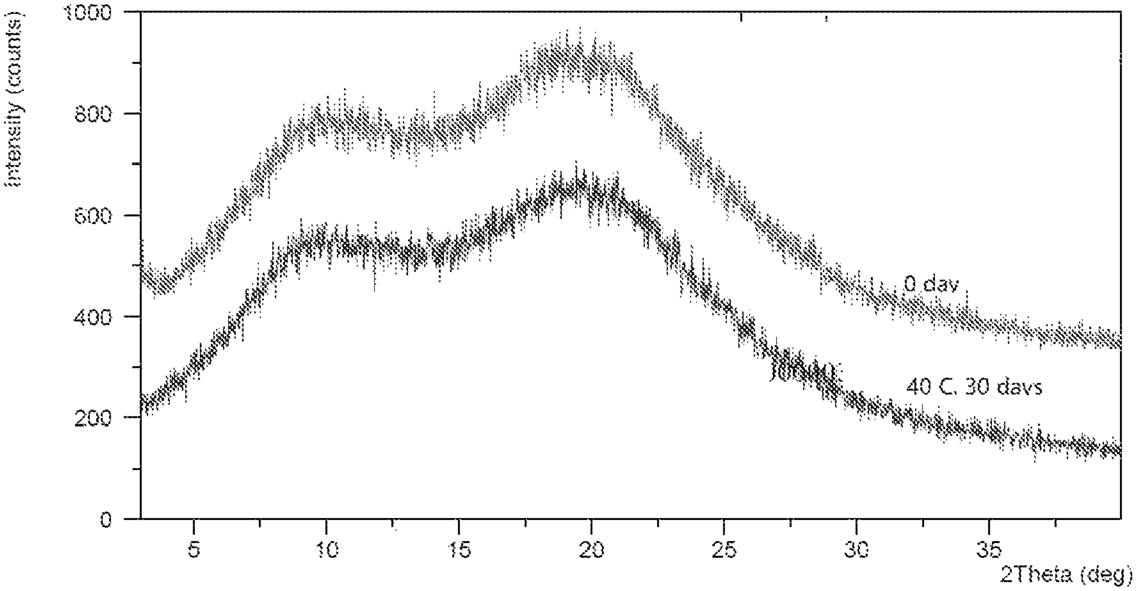
FIG. 30 shows XRPD overlay of amorphous solid dispersion of Compound 1 as MBP (Form C) from 3:7 ratio of Compound 1:HPMCAS-MF.

The resulting powder was evaluated by the XRPD pattern technique to determine its amorphous nature. As FIG. 8 does not show any crystalline peaks, the powder was determined to be amorphous (referred to as Form C or amorphous solid dispersion of Compound 1 of Form C). Form C was determined as having the glass transition temperature of 112.5° C. The drug loading was determined as 29.0%. The particle sizes were D90=173.3 μm, D50=60 μm, D10=12.3 μm. $^1$H-NMR spectra for Form C is shown in FIG. 22. The XRPD pattern data of the testing sample showed that Form C was stable at 1 month at 40° C./75% RH condition in as the XRPD pattern data of the testing sample at 14 days in FIG. 30 did not show any crystalline peaks.

Example 5

Preparation of Amorphous Solid Dispersion of Compound 1 (Form D)

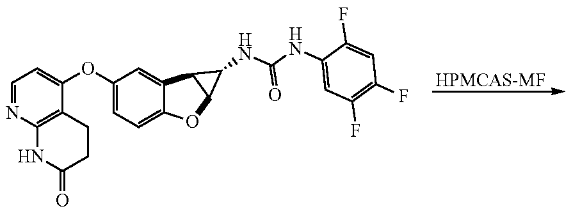

Compound 1

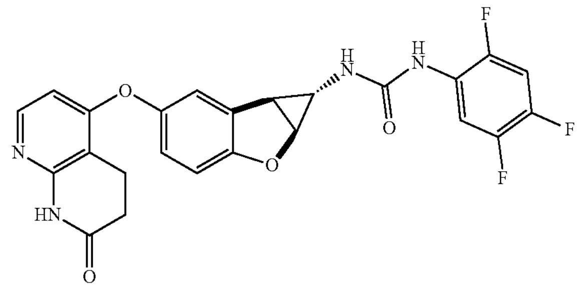

(HPMCAS-MF)m
Formula I

The amorphous solid dispersion of Compound 1 as micro-precipitation bulk powder was prepared as follows: Form A of Compound 1 as a poorly soluble drug and Hypromellose acetate succinate (HPMCAS-MF) in a ratio of 2:3 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 9:
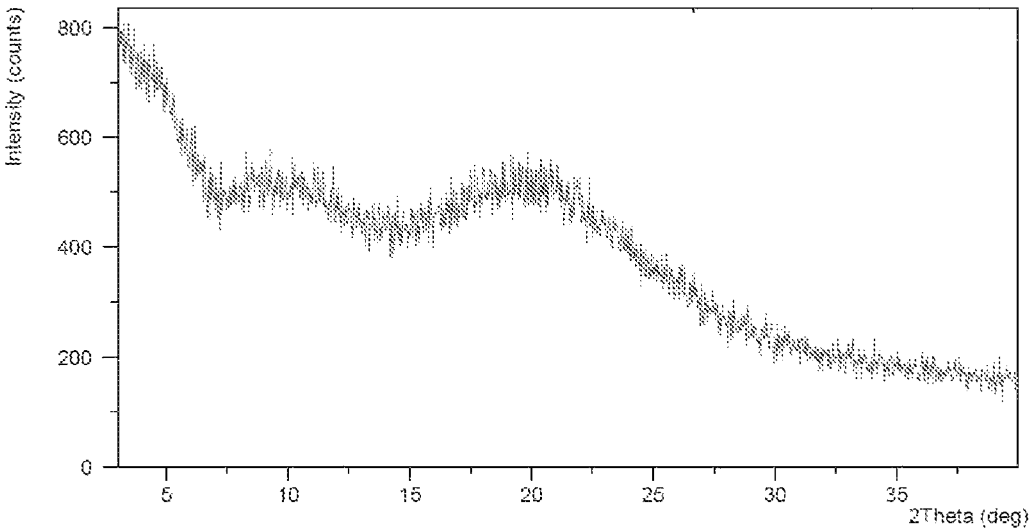
FIG. 9 shows an XRPD pattern of amorphous solid dispersion of Compound 1 as MBP (Form D) from 2:3 ratio of Compound 1:HPMCAS-MF.
Figure 23:
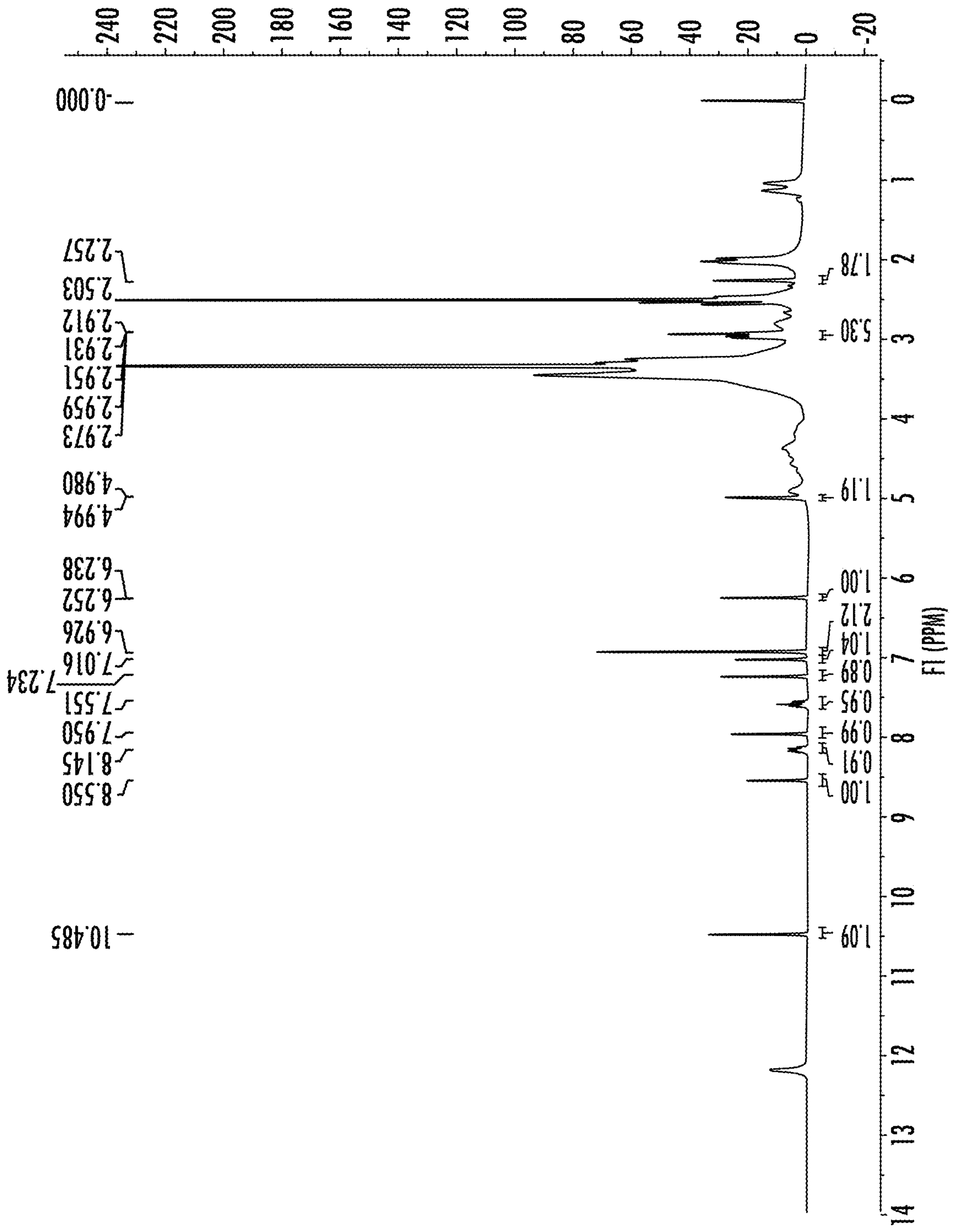
FIG. 23 shows a $^{1}$H-NMR spectrum of amorphous solid dispersion of Compound 1 as MBP (Form D) (Compound 1:MF=2:3)
Figure 31:
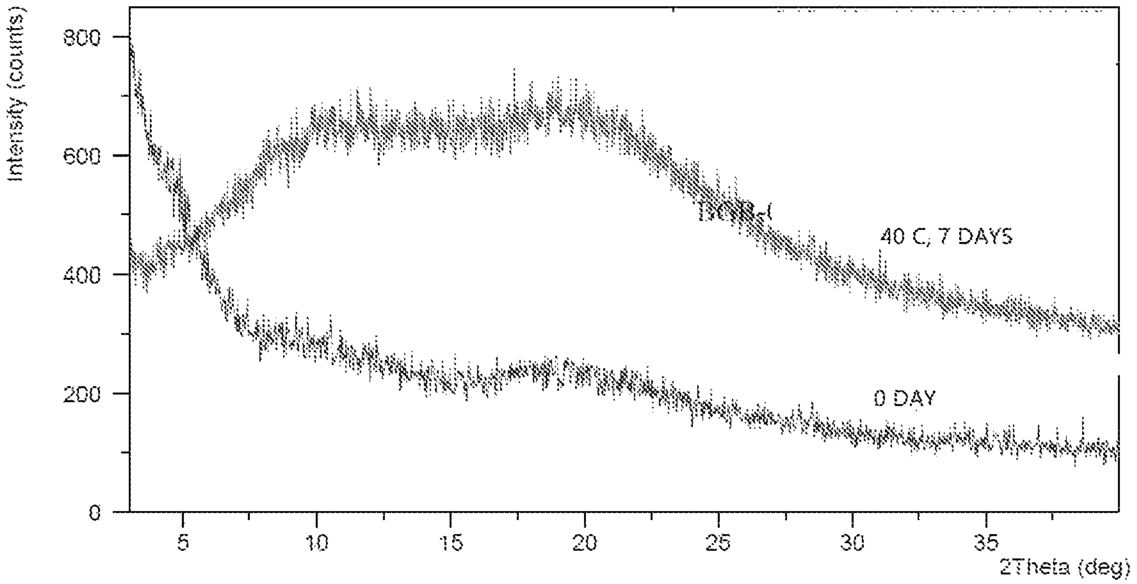
FIG. 31 shows XRPD overlay of amorphous solid dispersion of Compound 1 as MBP (Form D) from 2:3 ratio of Compound 1:HPMCAS-MF.

The resulting powder was evaluated by the XRPD pattern technique to determine its amorphous nature. As FIG. 9 does not show any crystalline peaks, the powder was determined to be amorphous (referred to as Form D or amorphous solid dispersion of Compound 1 of Form D). Form D was determined as having the glass transition temperature of 113.1° C. The drug loading was determined as 38.1%. The particle sizes were D90=244.8 μm, D50=81.4 μm, D10=16.2 μm. $^{1}$H-NMR spectra for Form D is shown in FIG. 23. The XRPD data of the testing sample showed that Form D was stable at 7 days at 40° C./75% RH condition in as the XRPD pattern data of the testing sample at 7 days in FIG. 31 did not show any crystalline peaks.

Example 6

Preparation of Amorphous Solid Dispersion of Compound 1 (Form E)

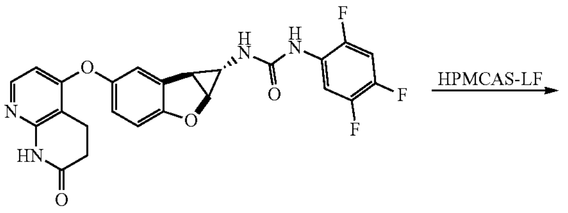

Compound 1

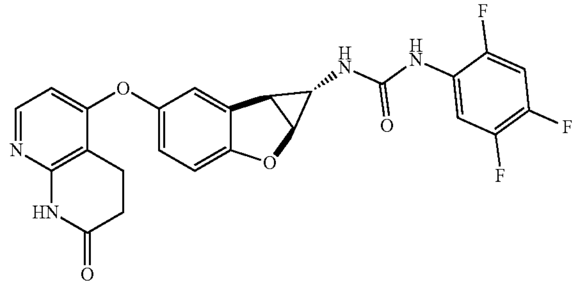

(HPMCAS-LF)m
Formula I

The amorphous solid dispersion of Compound 1 as micro-precipitation bulk powder was prepared as follows: Form A of Compound 1 as a poorly soluble drug and Hypromellose acetate succinate (HPMCAS-LF) in a ratio of 1:9 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 10:
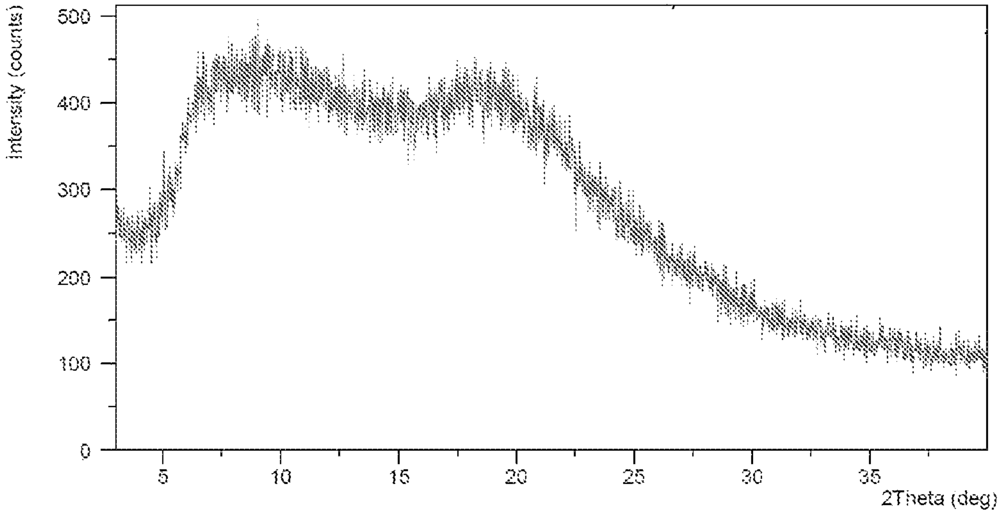
FIG. 10 shows an XRPD pattern of amorphous solid dispersion of Compound 1 as MBP (Form E) from 1:9 ratio of Compound 1:HPMCAS-LF.
Figure 24:
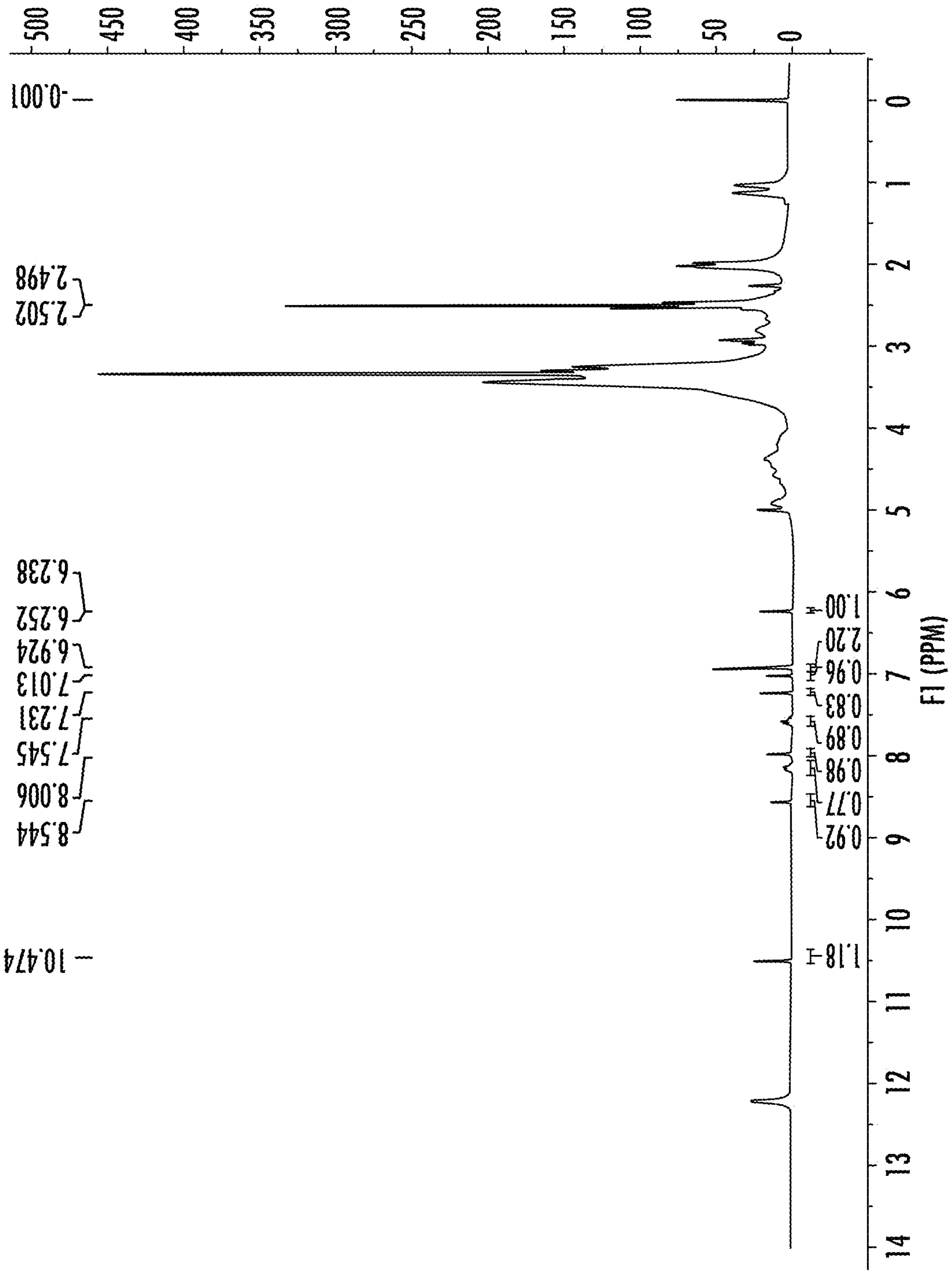
FIG. 24 shows a $^{1}$H-NMR spectrum of amorphous solid dispersion of Compound 1 as MBP (Form E) (Compound 1:LF=1:9)
Figure 32:
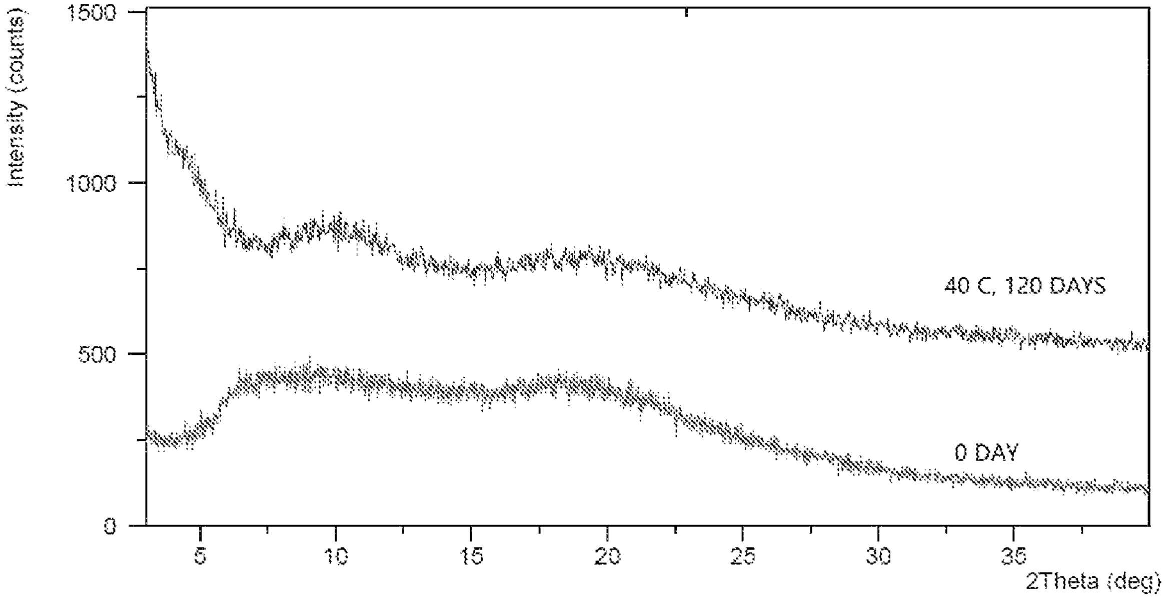
FIG. 32 shows XRPD overlay of amorphous solid dispersion of Compound 1 as MBP (Form E) from 1:9 ratio of Compound 1:HPMCAS-LF.

The resulting powder was evaluated by the XRPD pattern technique to determine its amorphous nature. As FIG. 10 does not show any crystalline peaks, the powder was determined to be amorphous (referred to as Form E or amorphous solid dispersion of Compound 1 of Form E). Form E was determined as having the glass transition temperature of 113.8° C. The drug loading was determined as 9.3%. The particle sizes were D90=575.8 μm, D50=265.9 μm, D10=101.4 μm. $^{1}$H-NMR spectra for Form E is shown in FIG. 24. The XRPD data of the testing sample showed that Form E was stable at 4 months at 40° C./75% RH condition in as the XRPD data of the testing sample at 4 months in FIG. 32 did not show any crystalline peaks.

Example 7

Preparation of Amorphous Solid Dispersion of Compound 1 (Form F)

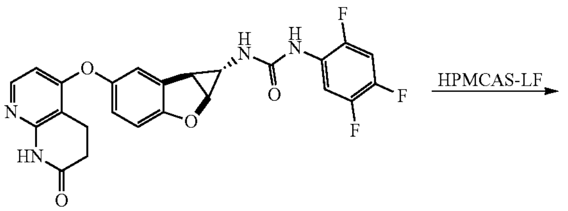

Compound 1

-continued

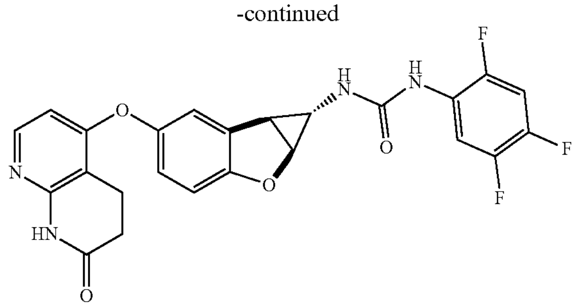

(HPMCAS-LF)m
Formula I

The amorphous solid dispersion of Compound 1 as micro-precipitation bulk powder was prepared as follows.

Reactor 1 was vacuumed to ≤−0.08 MPa and then charged with inert nitrogen to atmosphere. DMAc (32.9 kg, 25.0 volumes) via a 0.2 μm micron filter and Hypromellose Acetate Succinate (HPMCAS-LF) (5.6 kg, 4.0 wt) were charged to the reactor. The mixture was stirred for at least 2 hours at 20±5° C. until the mixture became clear. Compound 1 (1.4 kg, 1.0 wt) was then charged to the reactor, was stirred for at least 10 hours at 20±5° C. until the system became clear, labeled as System A.

Reactor 2 was vacuumed to ≤−0.08 MPa and then charged with inert nitrogen to atmosphere. 0.01 mol/L hydrochloric acid was charged to the reactor via a 0.2 μm micron filter, cooled to 0-5° C., labeled as System B.

Solidification: System A was charged to System B slowly at 0-5° C. The mixture was stirred for at least 2 hours, was then centrifuged. The filter cake was washed with purified water (10.0 volumes).

Slurry with diluted hydrochloric acid: 0.01 mol/L hydrochloric acid (125.0 volumes) was charged via a 0.2 μm micron filter to the reactor. The above-mentioned filter cake was charged to the reactor and stirred for at least 2 hours at 10±10° C. The mixture was centrifuged, and the filter cake was washed with purified water (10.0 volumes). Slurry with diluted hydrochloric acid was repeated one more time.

Slurry with purified water: purified water (125.0 volumes) was charged to the reactor. The above-mentioned filter cake was charged to the reactor and stirred for at least 2 hours at 10±10° C. The mixture was centrifuged, and the filter cake was washed with purified water (10.0 volumes).

The cake was then dried with $N_2$ flow at 20±5° C. for at least 10 hours and sampled for Karl-Fischer Titration Method until the water content ≤1.0%, and sampled for solvent residue with the criterion of DMAc≤1090 ppm. If the solvent residue does not meet the criterion, the cake is dried again under vacuum at 50±5° C. until the solvent residue meets the criterion.

The material collected after drying was sampled for HPLC analysis with the criteria being that the drug loading (% w/w) is between 19%-21%. The crude product of MBP was ground and filtered through 60 mesh screen, then jet-milled to D90<200 nm. The material was sampled for XRPD pattern analysis to determine the amorphous nature of the powder. The product was packaged in double LDPE bags sealed with cable ties, encased within a heat-sealed aluminum foil bag with desiccant, and store at 2-8° C.

Figure 11:
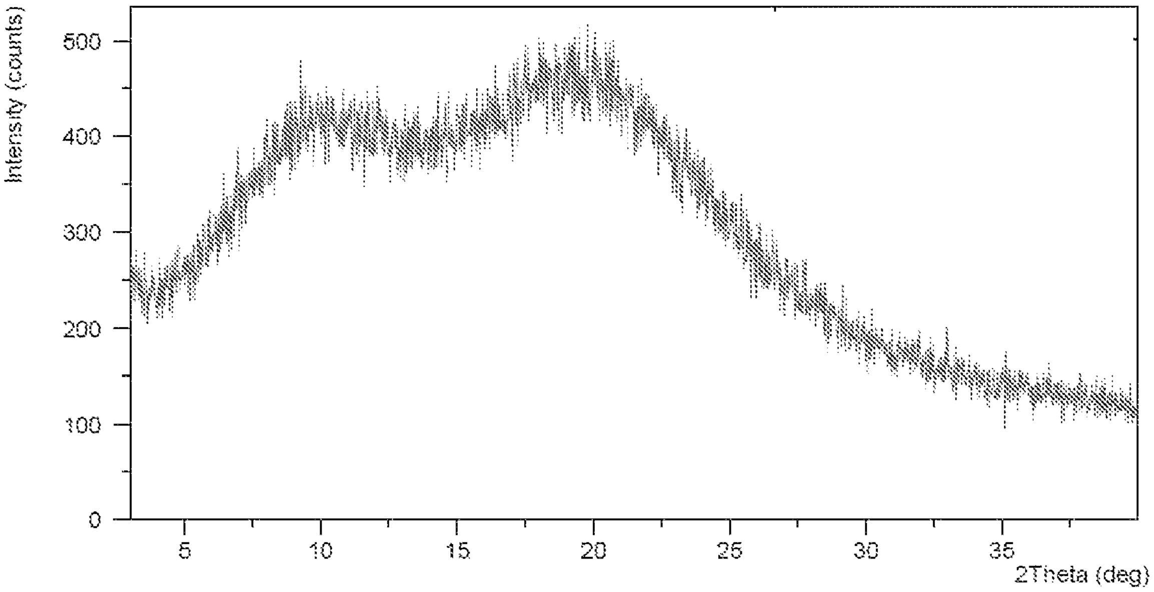
FIG. 11 shows an XRPD pattern of amorphous solid dispersion of Compound 1 as MBP (Form F) from 1:4 ratio of Compound 1:HPMCAS-LF.
Figure 18:
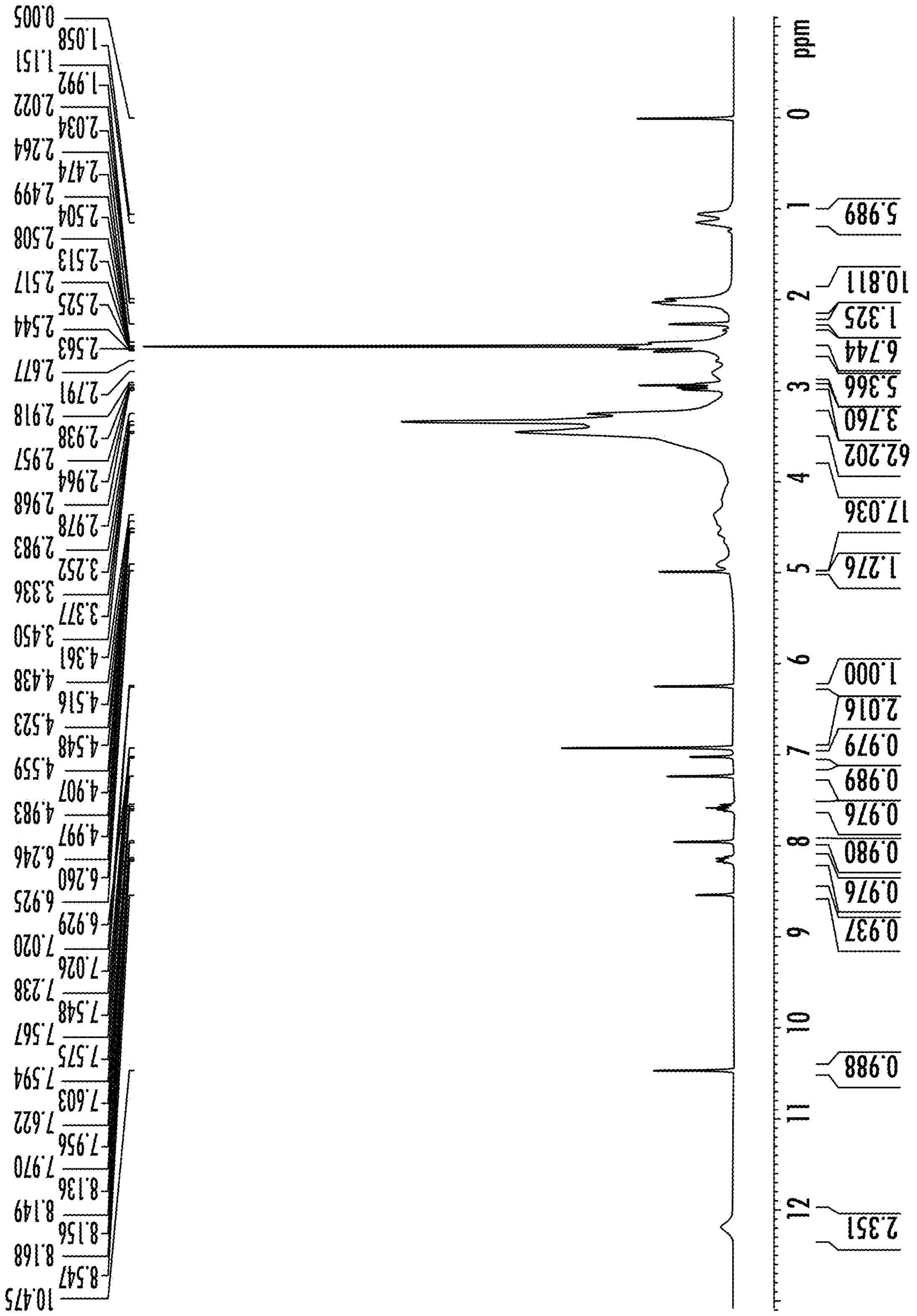
FIG. 18 shows a $^{1}$H-NMR spectrum of amorphous solid dispersion of Compound 1 as MBP (Form F) (Compound 1:LF=1:4)
Figure 20:
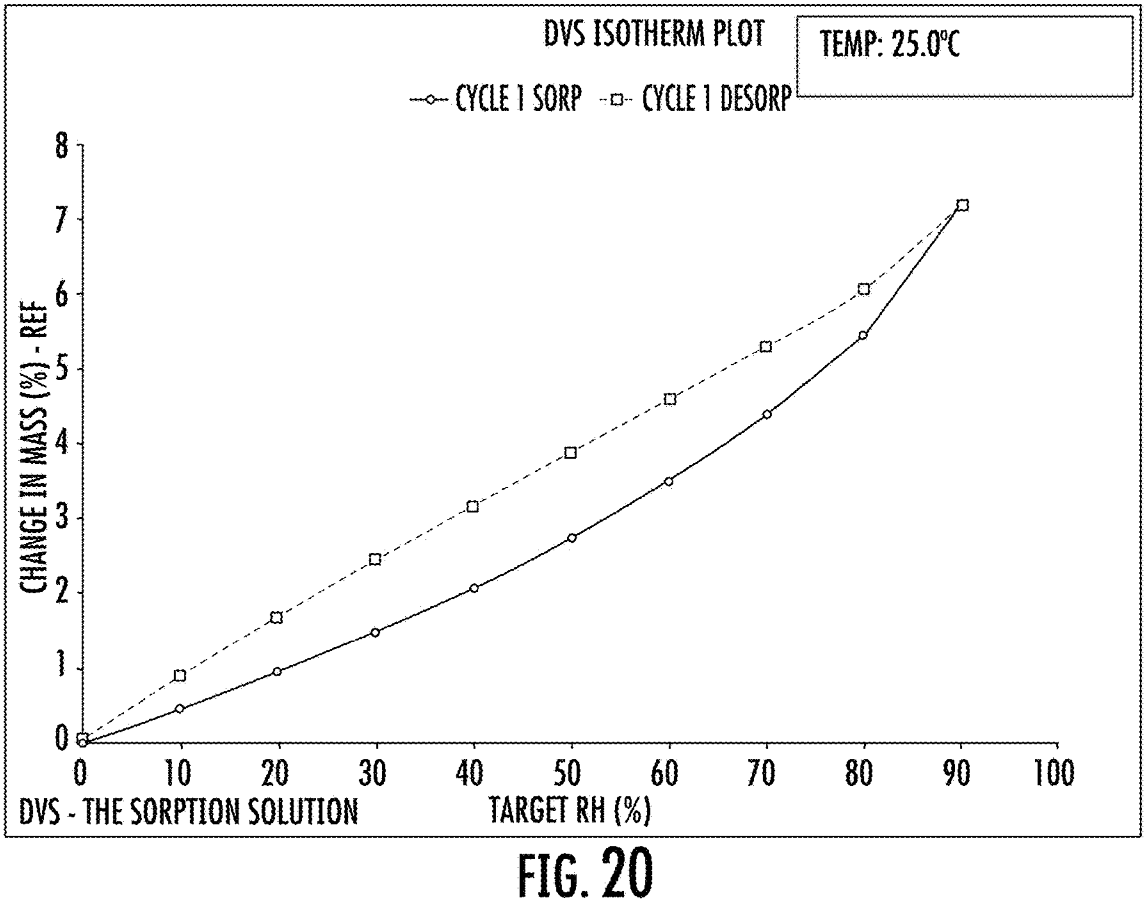
FIG. 20 shows hygroscopicity (i.e., moisture sorption) of amorphous solid dispersion of Compound 1 as MBP (Form F) (Compound 1:HPMCAS-LF=1:4) by DVS.

The drug loading was determined as 20.2%. As FIG. 11 does not show any crystalline peaks, the powder was determined to be amorphous (referred to as Form F or amorphous solid dispersion of Compound 1 of Form F). $^1$H-NMR spectra for Form F is shown in FIG. 18. Hygroscopicity (i.e., Moisture sorption) of Form F by DVS is shown in FIG. 20.

The long-term stability studies of Form F showed there was no significant chemical purity change occurred when stored at 25° C.°/60% RH for up to 24 months (total impurities: T0=1.0% and T24=0.9%) and at 40° C./75% RH condition for up to 6 months (total impurities: T0=1.0% and T6=1.1%). In addition, no optical purity changes were observed when stored at 25° C./60% RH for up to 24 months and at 40° C./75% RH condition for up to 6 months. Chiral purity and polymorph results had no changes when stored at 25° C./60% RH for up to 24 months. The water content of Form F was reported as 0.70% (initial and at 0 month), 0.80% (at 1 month), 1.39% (at 3 month), 1.86% (at 6 month), 0.62% (at 9 month), 0.89% (at 12 month), 2.35% (at 18 month) and 0.55% (at 24 month) and the variation of the water content was found to be consistent with that of environmental humidity and actually had no substantial change during the 24 month storage period.

The XRPD data showed that no conversion of amorphous form into crystalline form occurred after long-term storage at 2-8° C. or 25° C./60% RH for 24 months and at 40° C./75% RH condition for 6 months.

Figure 33:
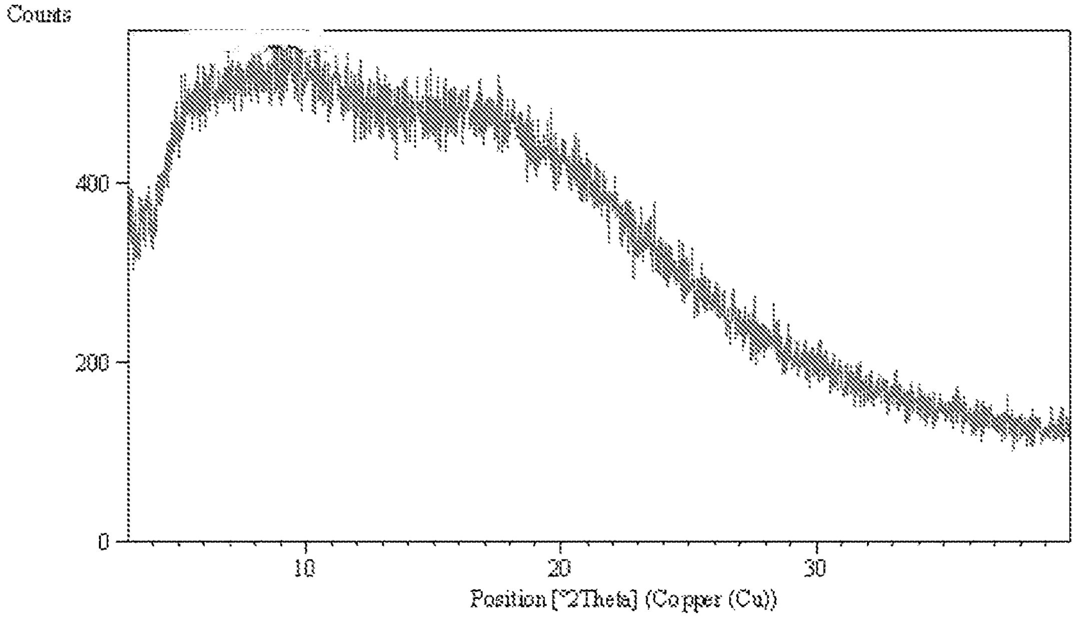
FIG. 33 shows XRPD of the recovered precipitate of Form F.

To mimic the absorption environment in GI system during oral dosing, an aged MBP sample was stirred in a buffer of pH 6.8 for 2 hours, the remaining precipitate was filtered, washed with water and dried in vacuum. The XRPD of the recovered precipitate showed there was no change of amorphous form in FIG. 33. Instead, the neat HPMCAS-LF was dissolved completely in the same buffer under the same condition. This extraordinary amorphous form stability plus the favorable physicochemical and mechanistic properties of Form F made it highly suitable for the drug product manufacture of clinical trial materials or commercial use.

TABLE 5

Physical stability of Form F sample in pH 6.8 buffer at 37° C.

| Sample | Weight of Sample | Stirred in pH 6.8 Buffer for 2 h at 37° C. | Precipitate Analysis |
|---|---|---|---|
| HPMCAS-LF | 500 mg | Completely dissolved in 200 mL of the buffer | |
| Form F (Stored at 2-8° C. for 15 months; Initial Assay by HPLC: 19.2%) | 250 mg | Partially dissolved in 100 mL of the buffer. The precipitate filtered, washed and dried in vacuum at 50° C. | The recovered solid was analyzed by:<br>1) XRPD: Amorphous Form<br>2) Assay: Increased from 19.2% to 31.1% by HPLC |

It was concluded that the amorphous solid dispersion of Form F is not a simple physical mixture of Compound 1 and HPMCAS and it has unique physicochemical properties as summarized in Table 6.

TABLE 6

The main physicochemical properties of Form F

| | |
|---|---|
| Properties | White to off-white solid |
| Solubility | The solubility of the sample is directly related to the pH of the solution, with a solubility of 0.24 mg/mL in 0.1N HCl and less than 5 µg/mL in both pH 4.5 buffer and pH 6.8 buffer. Surfactants improve the solubility to a large extent, especially sodium lauryl sulphate (SLS) and hexadecyl trimethyl ammonium bromide (HTAB), 1% SLS and 0.5% HTAB increased the solubility to 0.45 mg/mL and 0.31 mg/mL. At the same time, different concentrations of HTAB have different effects on solubility. |
| Hygroscopicity | At 80% relative humidity (RH), the sample had an actual moisture of 81.5% and a moisture absorption of about 5.425%; the sample was moderately hygroscopic. |
| Thermogravimetric Analysis (TGA) and Differential Scanning Calorimetry (DSC) | In the TGA and DSC spectra, the sample had 1.438% weight loss before 100° C. and the glass transition temperature was 111.07° C. |
| Crystal form | Under polarized light microscopy, samples were irregular shape. XRPD (XRPD): MBP Form F is an amorphous solid. |
| Particle size distribution | D90 = 118 µm |
| Flowability | Good |
| Stability | Form F is in amorphous form for 24 months at long-term condition (25° C./60% RH) as well as for 6 months at accelerated condition (40° C./75% RH) |
| Bulk density | 0.25 g/mL |
| Tap density | 0.42 g/mL |

Example 8

Preparation of Amorphous Solid Dispersion of Compound 1 (Form G)

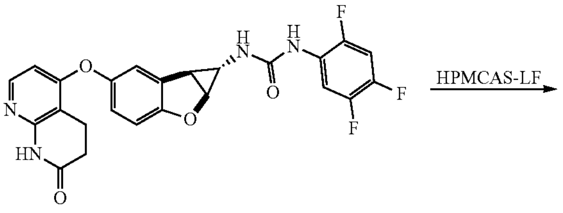

Compound 1

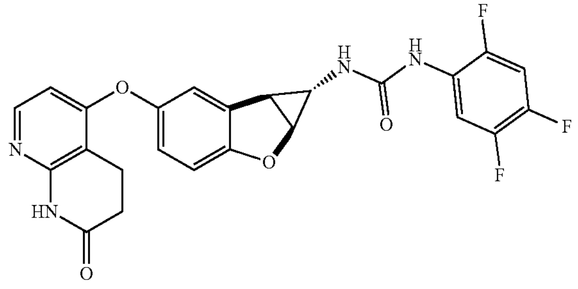

(HPMCAS-LF)m
Formula I

The amorphous solid dispersion of Compound 1 as micro-precipitation bulk powder was prepared as follows: Form A of Compound 1 as a poorly soluble drug and Hypromellose acetate succinate (HPMCAS-LF) in a ratio of 3:7 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 12:
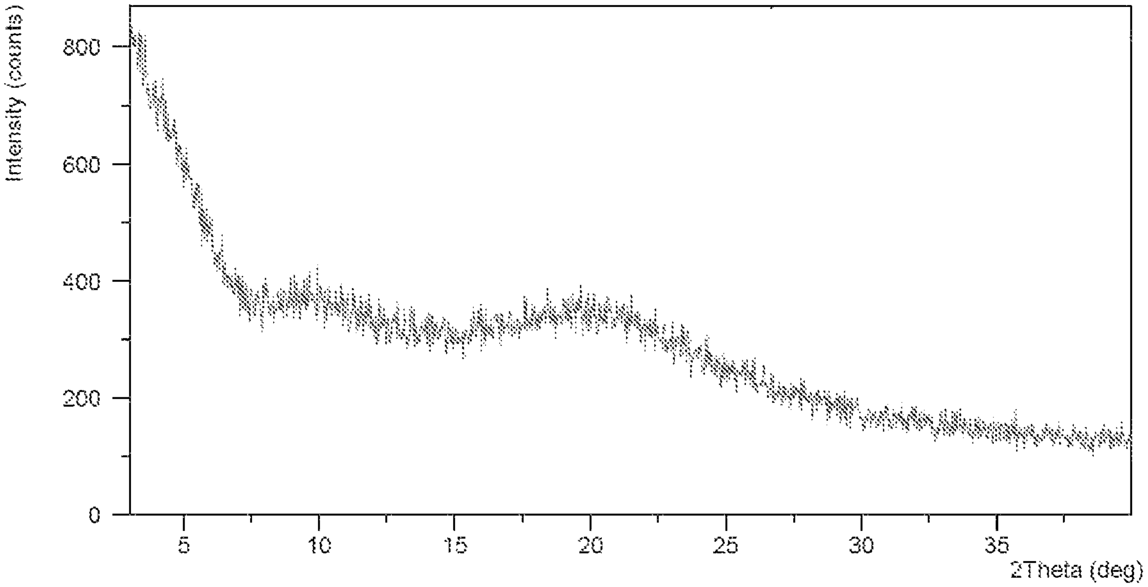
FIG. 12 shows an XRPD pattern of amorphous solid dispersion of Compound 1 as MBP (Form G) from 3:7 ratio of Compound 1:HPMCAS-LF.
Figure 25:
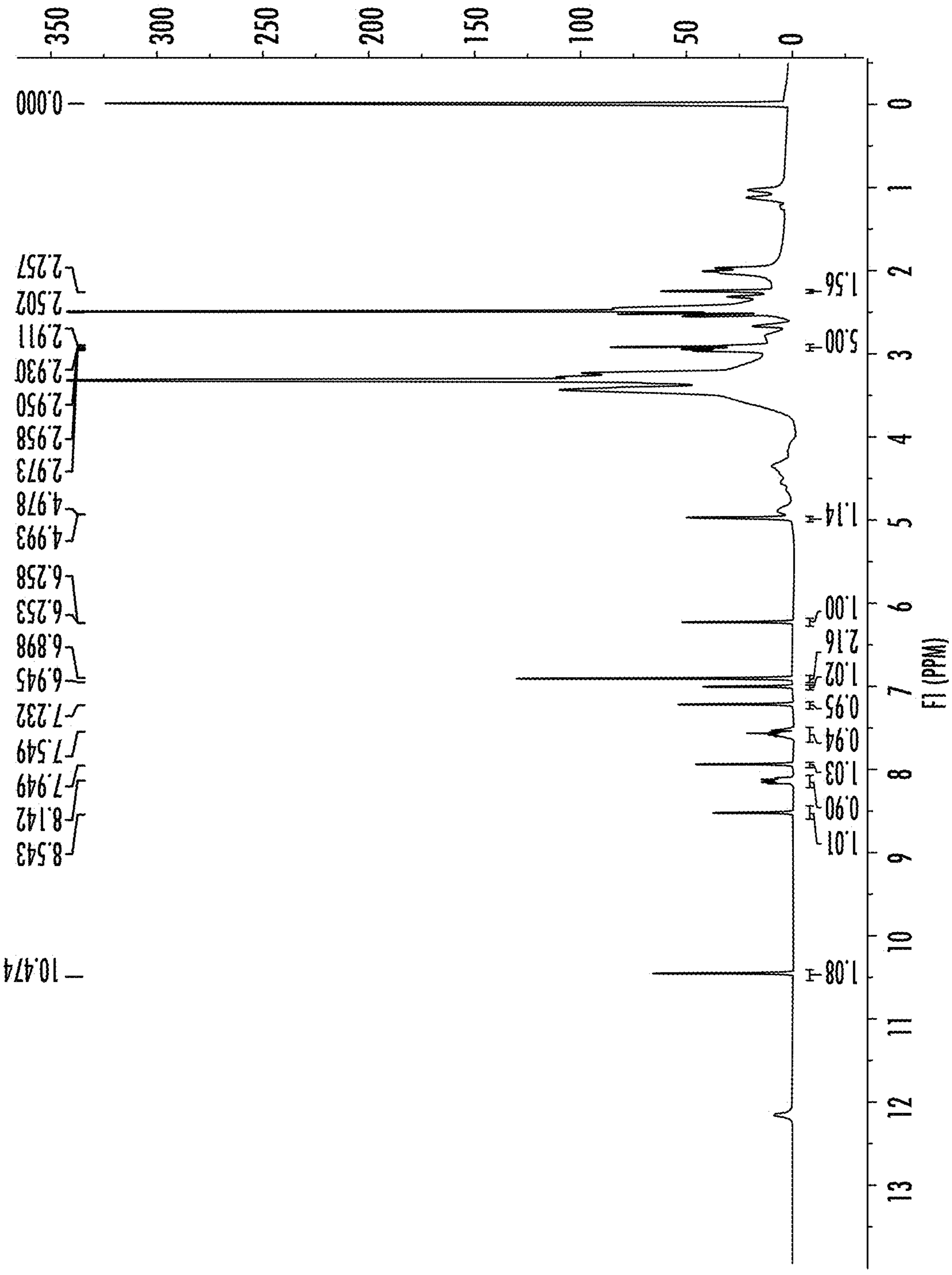
FIG. 25 shows a $^{1}$H-NMR spectrum of amorphous solid dispersion of Compound 1 as MBP (Form G) (Compound 1:LF=3:7)

The resulting powder was evaluated by the XRPD pattern technique to determine its amorphous nature. As FIG. 12 does not show any crystalline peaks, the powder was determined to be amorphous (referred to as Form G or amorphous solid dispersion of Compound 1 of Form G). Form G was determined as having the glass transition temperature of 111.5° C. The drug loading was determined as 30.3%. The particle sizes were D90=181.6 µm, D50=74.1 µm, D10=16.4 µm. $^1$H-NMR spectra for Form G is shown in FIG. 25.

Example 9

Preparation of Amorphous Solid Dispersion of Compound 1 (Form H)

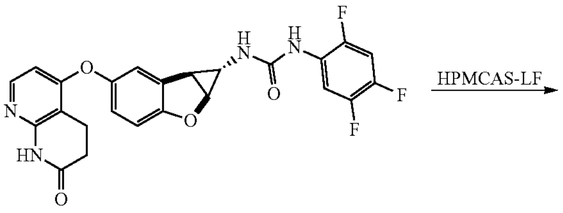

Compound 1

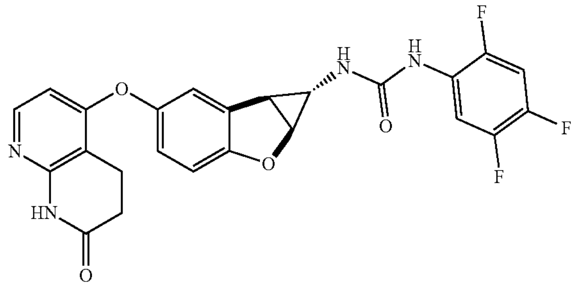

(HPMCAS-LF)m
Formula I

The amorphous solid dispersion of Compound 1 as micro-precipitation bulk powder was prepared as follows: Form A of Compound 1 as a poorly soluble drug and Hypromellose acetate succinate (HPMCAS-LF) in a ratio of 2:3 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 13:
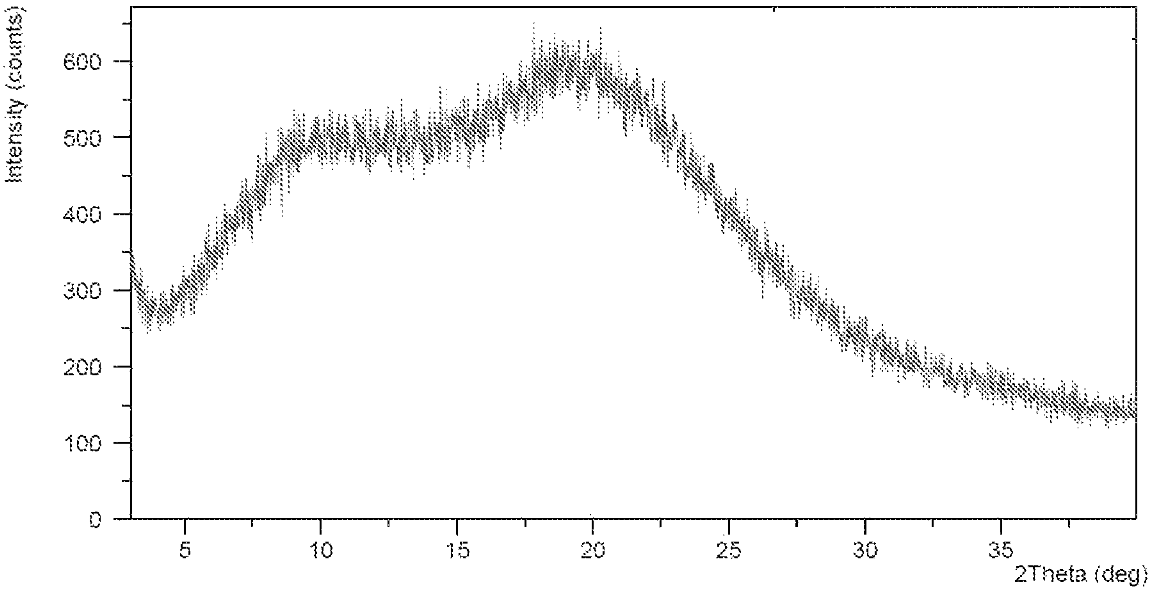
FIG. 13 shows an XRPD pattern of amorphous solid dispersion of Compound 1 as MBP (Form H) from 2:3 ratio of Compound 1:HPMCAS-LF.
Figure 26:
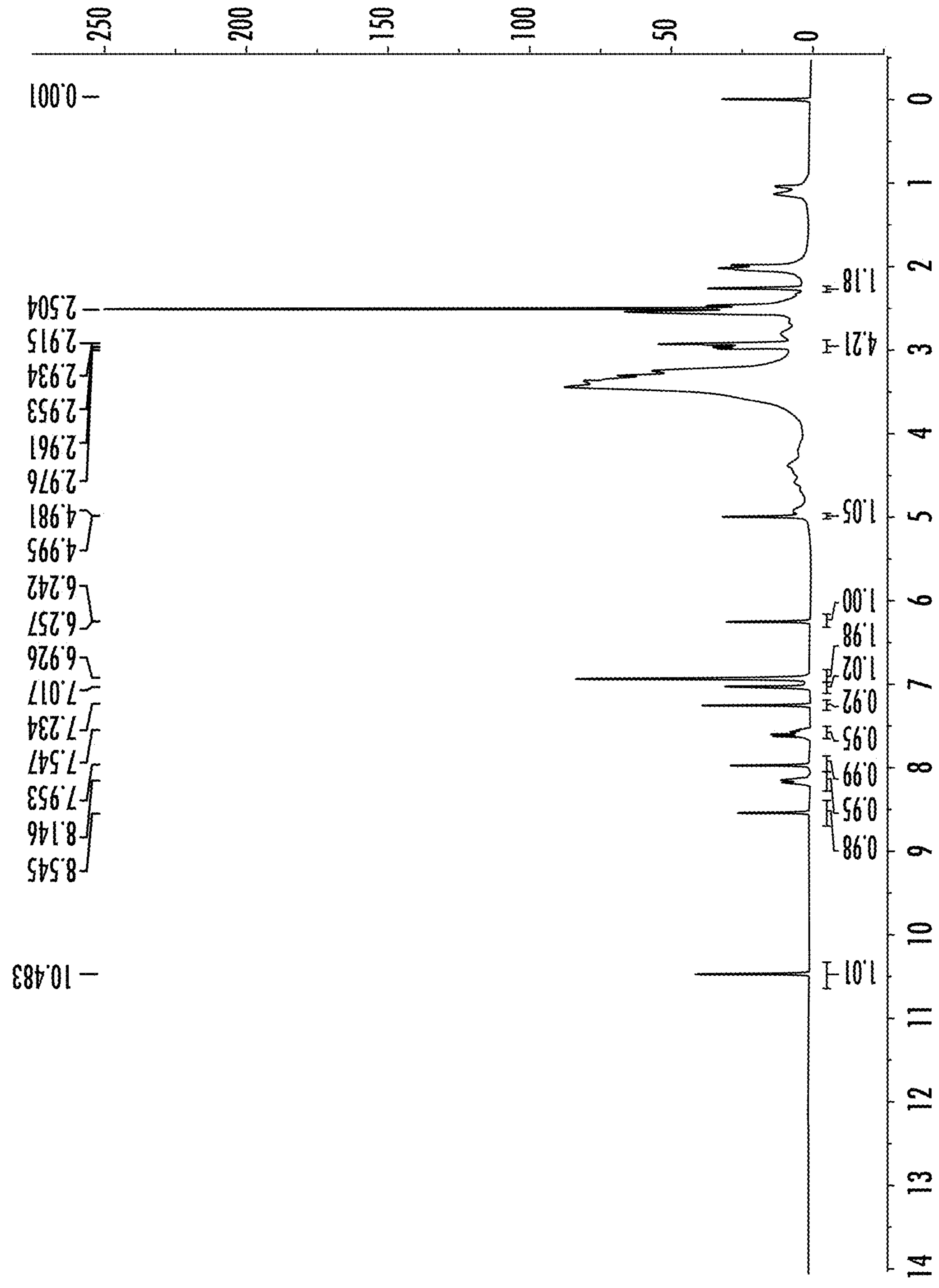
FIG. 26 shows a $^{1}$H-NMR spectrum of amorphous solid dispersion of Compound 1 as MBP (Form H) (Compound 1:LF=2:3)

The resulting powder was evaluated by the XRPD pattern technique to determine its amorphous nature. As FIG. 13 does not show any crystalline peaks, the powder was determined to be amorphous (referred to as Form G or amorphous solid dispersion of Compound 1 of Form G). Form G was determined as having the glass transition temperature of 114.2° C. The drug loading was determined as 39.4%. The particle sizes were D90=180.4 μm, D50=62.4 μm, D10=13.6 μm. $^1$H-NMR spectra for Form G is shown in FIG. 26.

Example 10

Preparation of Amorphous Solid Dispersion of Compound 1 (Form I)

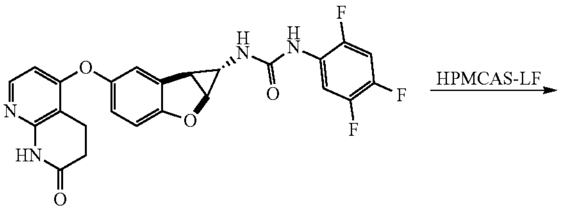

Compound 1

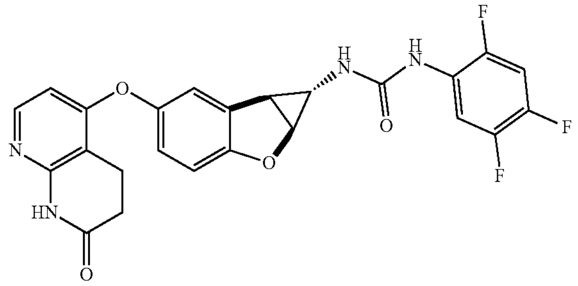

(HPMCAS-HF)m
Formula I

The amorphous solid dispersion of Compound 1 as microprecipitation bulk powder was prepared as follows: Form A of Compound 1 as a poorly soluble drug and Hypromellose acetate succinate (HPMCAS-HF) in a ratio of 1:4 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 14:
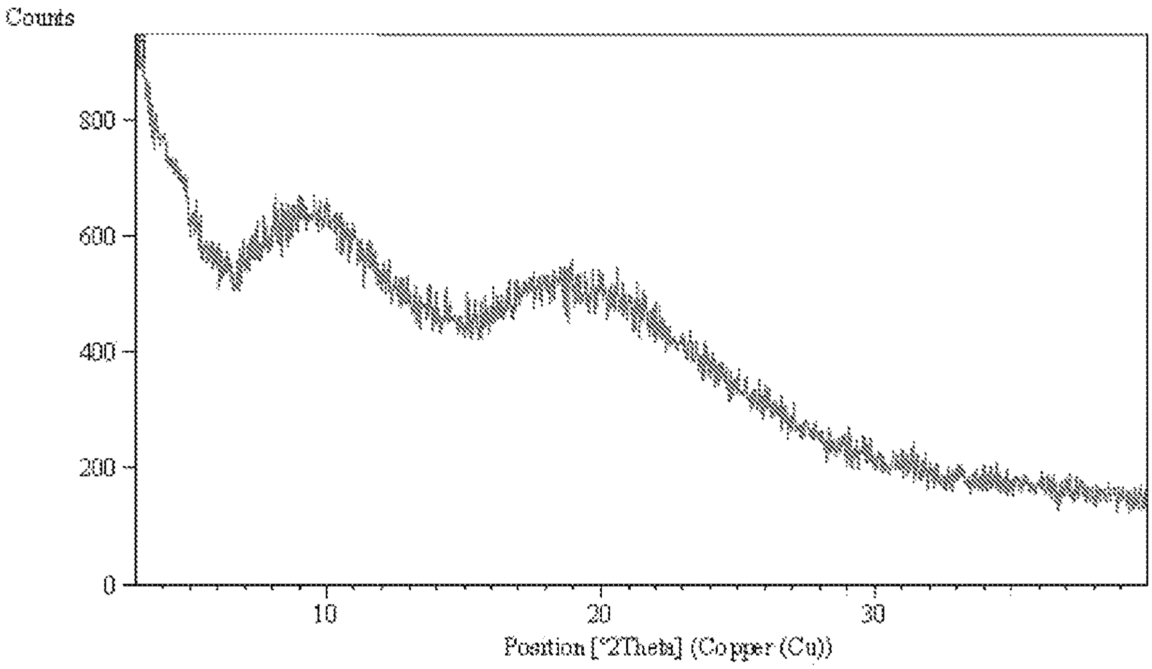
FIG. 14 shows an XRPD pattern of amorphous solid dispersion of Compound 1 as MBP (Form I) from 1:4 ratio of Compound 1:HPMCAS-HF.
Figure 27:
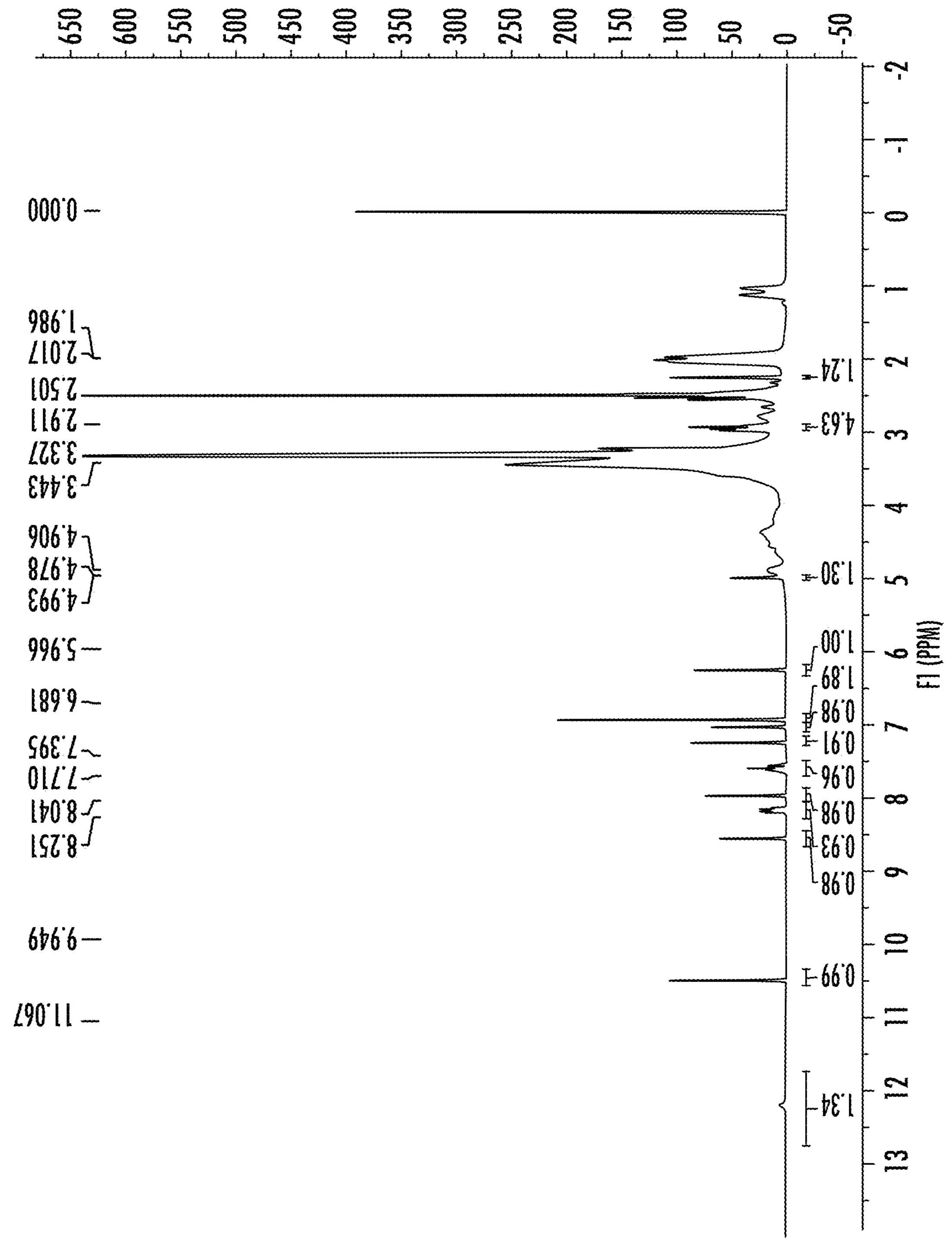
FIG. 27 shows a $^1$H-NMR spectrum of amorphous solid dispersion of Compound 1 as MBP (Form I) (Compound 1:HF=1:4)

The resulting powder was evaluated by the XRPD pattern technique to determine its amorphous nature. As FIG. 14 does not show any crystalline peaks, the powder was determined to be amorphous (referred to as Form I or amorphous solid dispersion of Compound 1 of Form I). Form I was determined as having the glass transition temperature of 111.6° C. The drug loading was determined as 19.5%. The particle sizes were D90=217.4 μm, D50=84.4 μm, D10=21 μm. $^1$H-NMR spectra for Form I is shown in FIG. 27.

Example 11

Preparation of Amorphous Solid Dispersion of Compound 1 (Form J)

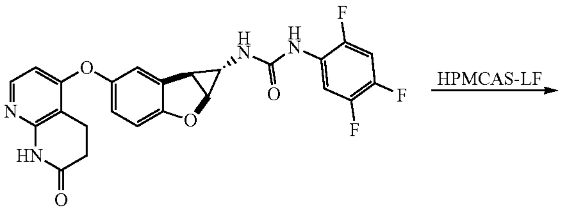

Compound 1

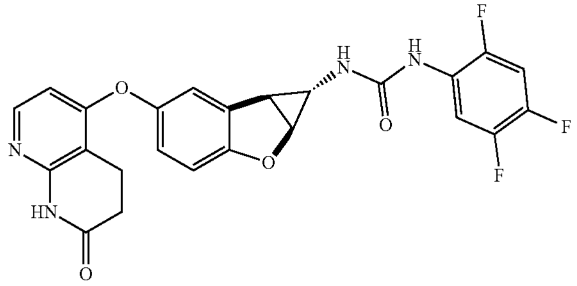

(HPMCAS-MF)m
Formula I

The amorphous solid dispersion of Compound 1 as microprecipitation bulk powder was prepared as follows: Form A of Compound 1 as a poorly soluble drug and Hypromellose acetate succinate (HPMCAS-MF) in a ratio of 1:4 (w/w) were dissolved in DMA or DMF. The resulting solution was added into a stirred acidic aqueous solution (0.01 N HCl) cooled at 2-8° C. The drug was then co-precipitated out with HPMCAS from the acidic aqueous solution. After further stirring and filtering, the solid was washed a few times with 0.01 N HCl solution and water and then dried under vacuum at below 50° C. to give a microprecipitation bulk powder suitable for drug product manufacture.

Figure 15:
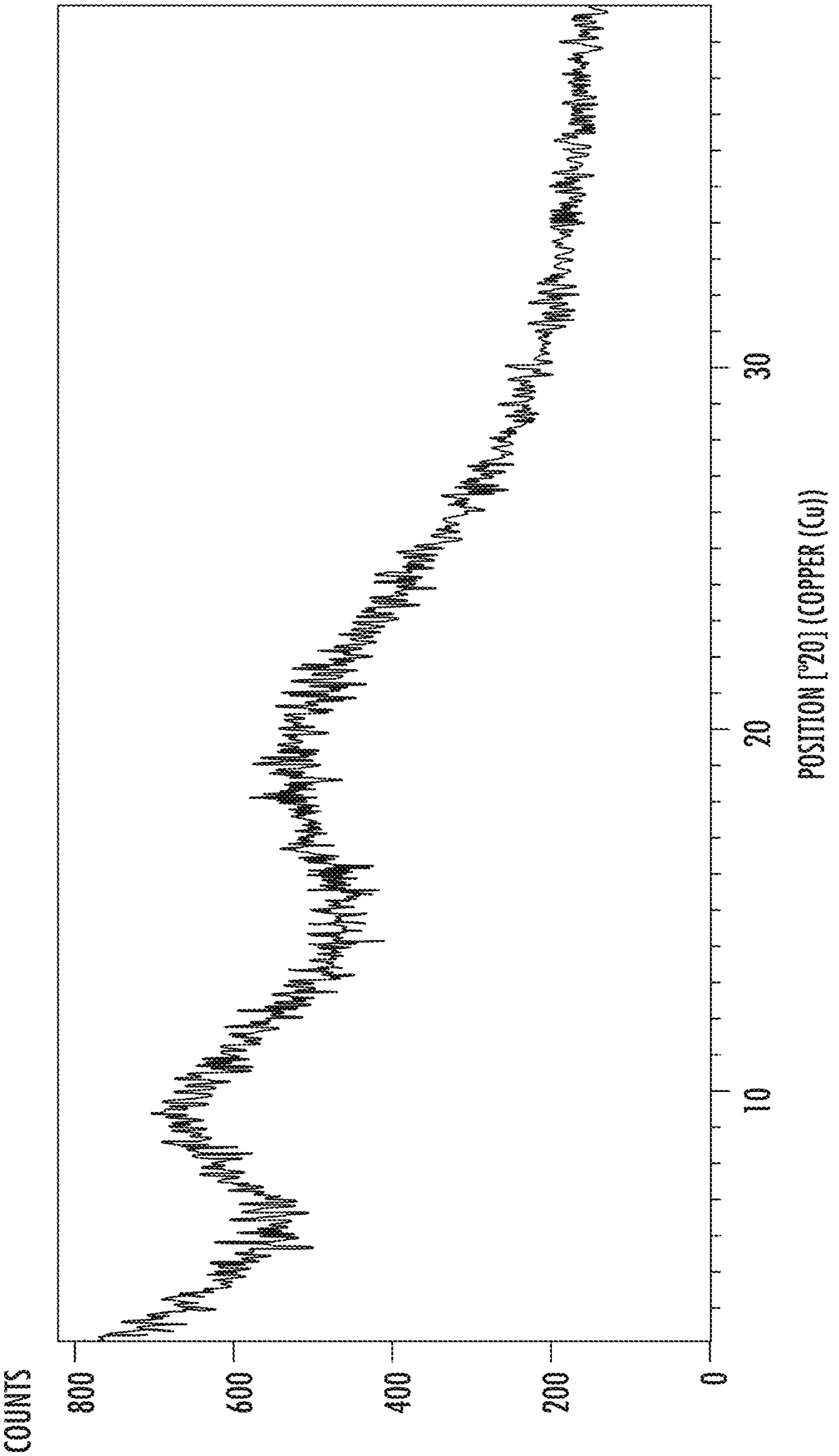
FIG. 15 shows an XRPD pattern of amorphous solid dispersion of Compound 1 as MBP (Form J) from 1:4 ratio of Compound 1:HPMCAS-MF.
Figure 28:
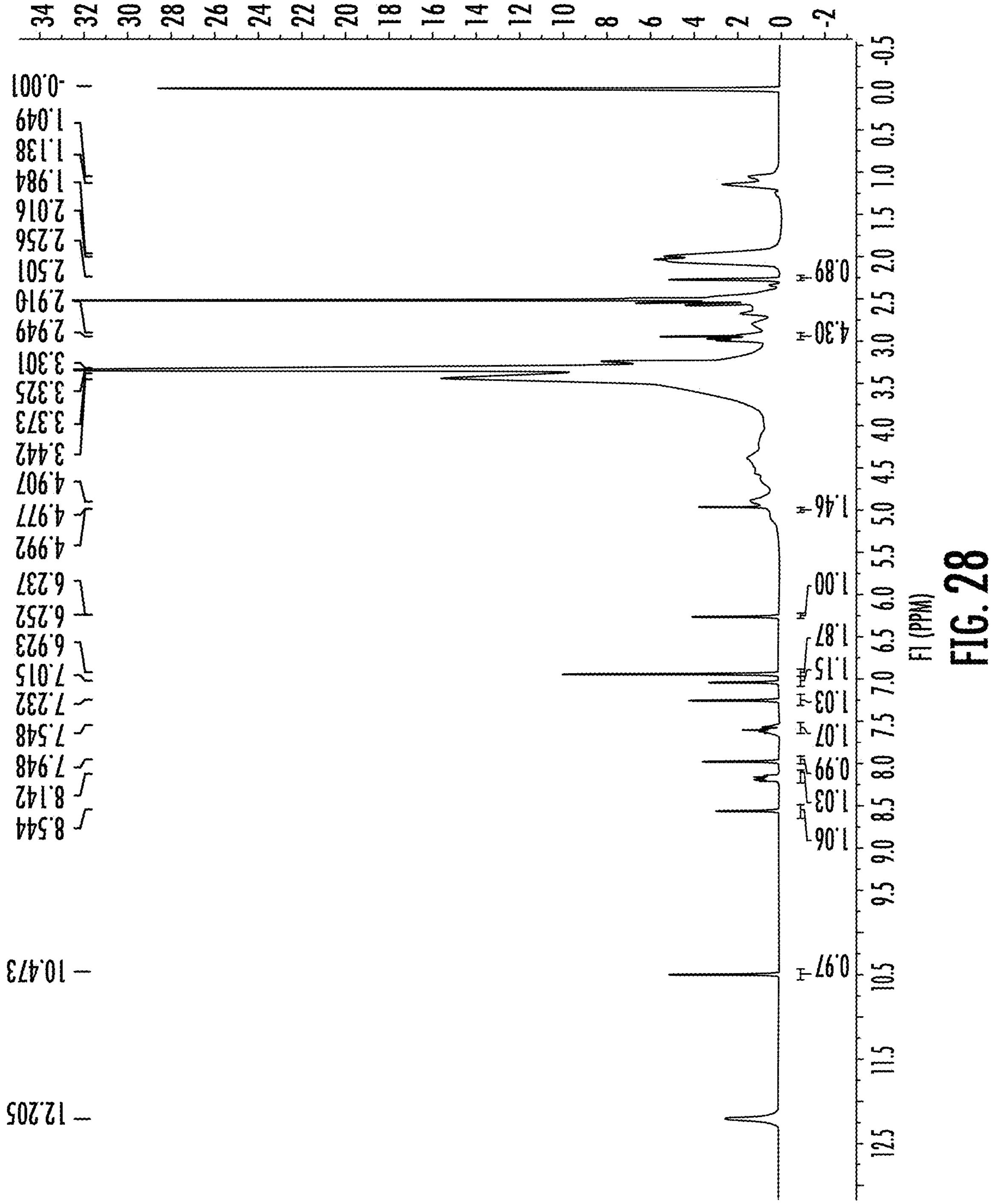
FIG. 28 shows a $^1$H-NMR spectrum of amorphous solid dispersion of Compound 1 as MBP (Form J) (Compound 1:MF=1:4)

The resulting powder was evaluated by the XRPD pattern technique to determine its amorphous nature. As FIG. 15 does not show any crystalline peaks, the powder was determined to be amorphous (referred to as Form J or amorphous solid dispersion of Compound 1 of Form J). Form J was determined as having the glass transition temperature of 115.3° C. The drug loading was determined as 18.2%. The particle sizes were D90=273.1 μm, D50=116.8 μm, D10=32.9 μm. $^1$H-NMR spectra for Form J is shown in FIG. 28.

Example 12

Preparation of Amorphous Solid Dispersion of Compound 1 (Form K)

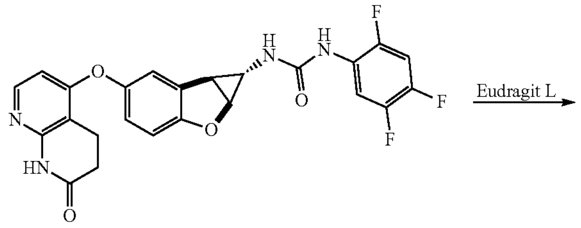

Compound 1

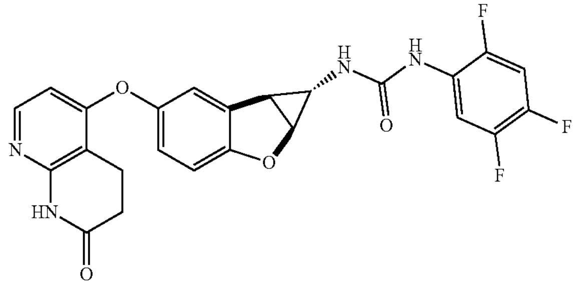

(Eudragit L)m
Formula I

The amorphous solid dispersion of Compound 1 as micro-precipitation bulk powder was prepared as follows: a mixture of Form A of Compound 1 (2.0 g) as a poorly soluble drug and Eudragit® L100-55 (8.0 g) in DMA (80 mL) was stirred for 16 hrs to give a clear solution A (thick solution). The resulting solution A was added dropwise by a drop funnel into a 5° C. mechanical stirred aqueous solution of HCl (0.01 N, 800 mL). Once addition was finished, all the solids were adhered to the agitator and could not be dispersed in the solution. It was failed to prepare Amorphous Solid Dispersion of Compound 1 using Eudragit® L100-55.

Example 13

Pharmacokinetics of Amorphous Solid Dispersion of Compound 1 as MBP (Form F)

The fully-validated LC-MS/MS method was well used for the pharmacokinetic (PK) studies of amorphous solid dispersion of Compound 1 as MBP (Form F) in Sprague-Dawley rats and beagle dogs following single- and multiple-dose administrations.

Amorphous solid dispersion of Compound 1 as MBP (Form F) has high oral bioavailability in both rats (18.4% to 74.8%) and dogs (68.6% to 112%). Its elimination half-lives ranged from 1.7 to 3.2 hours in rats and 12 to 28 hours in dogs after oral administration.

The kinetics was linear over the dose range of 0.5 to 5 mg/kg in rats and 0.2 to 2 mg/kg in dogs. After multiple dosing, an accumulation (~1.5-fold) was observed in rats. This slight accumulation was statistically significant in female rats, but not in male rats. No accumulation was noted after multiple dosing in dogs.

Example 14

Pharmacokinetic Comparison of Form a, B, C, D, E, F, G and H in Rats

1. Drugs and Reagents:

Powder of Form A with particle sizes of D90=62.4 μm after micronization. The material content (purity) was not less than 98.0%.

Powder of Form B with particle sizes of D90=69.9 μm, D10=3.5 um, D50=1.4 um after micronization. The material content (purity) was not less than 98.0%.

Powders of Forms C, D, E, F, G and H with particle sizes of D90<600 μm after micronization. The material content (purity) was not less than 98.0%.

2. Experiment Animals:

Rats, male and female, were used in this study.

3. Pharmaceutical Preparation:

An appropriate amount of each substance was weighted and was dispersed in 0.5% sodium carboxymethyl cellulose. A suspension was prepared at the desired concentration of Compound 1 for each substance. All the doses and concentrations of Compound 1 were calculated with freebase in this study.

4. Administration and Sample Collection:

The dosing solutions were freshly prepared prior to dose administration. The actual body weights and actual volume injected were recorded accordingly. The rats were fasted overnight and were allowed to intake food four hours after dosing. Each suspension was administrated orally to rats at a dose ranged from 0.5 to 5 mg/kg. Blood samples (~1.0 mL) were collected at pre-dose and at different times up to 36 hours post-dosing via cephalic vein plexus. Whole blood was processed by centrifugation and plasma samples were collected and kept at freezer prior to analysis. Plasma samples were processed by protein precipitation. Concentrations of Compound 1 in the plasma samples were determined using a validated liquid chromatography-tandem mass spectrometry (LC-MS/MS) method. The plasma concentration-time data were analyzed using a non-compartmental model using Pharsight WinNonlin. The $C_{max}$ and Area under the concentration-time curve for each substance is shown in Table 7.

TABLE 7

PK Profiles of Forms A, B, C, D, E, F, G and H of Compound 1 in Rats

| Cmp 1 | Form A | Form A | Form B | Form C (Cmp 1: MF = 3:7) | Form D (Cmp 1: MF = 4:6) | Form E (Cmp 1: LF = 1:9) | Form F (Cmp 1: LF = 1:4) | Form G (Cmp 1: LF = 3:7) | Form H (Cmp 1: LF = 2:3) |
|---|---|---|---|---|---|---|---|---|---|
| Dosage (mpk) | 1 (IV) | 5 (PO) | 5 (PO) | 5 (PO) | 5 (PO) | 5 (PO) | 5 (PO) | 5 (PO) | 5 (PO) |
| T1/2 (h) | 4.2 | 2.94 | 2.47 | 2.7 | 2.8 | | | | |
| $Vd_{ss}$ (L/kg) | 1.15 | | | | | | | | |
| CL ($mL \cdot kg^{-1} \cdot min^{-1}$) | 3.15 | | | | | | | | |

TABLE 7-continued

PK Profiles of Forms A, B, C, D, E, F, G and H of Compound 1 in Rats

| Cmp 1 | Form A | Form A | Form B | Form C (Cmp 1: MF = 3:7) | Form D (Cmp 1: MF = 4:6) | Form E (Cmp 1: LF = 1:9) | Form F (Cmp 1: LF = 1:4) | Form G (Cmp 1: LF = 3:7) | Form H (Cmp 1: LF = 2:3) |
|---|---|---|---|---|---|---|---|---|---|
| $C_{max}$ (ng/mL$^{-1}$) | | 832 | 2324 | 2971 | 2728 | 1895 | 3057 | 2095 | 2201 |
| $AUC_{0-t}$ (h · ng · mL$^{-1}$) | 5332 | 5716 | 13134 | 19135 | 19888 | 15146 | 16019 | 15843 | 18213 |
| F (%) | 100 | 21 | 49 | 72 | 75 | 57 | 60 | 59 | 69 |

Compared to the crystalline form (Form A), the neat amorphous form of Compound 1 (Form B) also exhibited higher $C_{max}$ (ng/mL), $AUC_{0-inf}$, (ng·h/mL) and F(%). The oral bioavailability of the neat amorphous form of Compound 1 (Form B) was about 50% of that of the intravenous injection, while the oral bioavailability of Form A was about 20% of that of the intravenous injection. Furthermore, the above experiment showed that the $C_{max}$ (ng/mL) and $AUC_{0-inf}$(ng·h/mL) of Forms C, D, E, F, G and H, i.e., the amorphous solid dispersion solid as MBP were as high as approximately 2-4 times that of Form A (i.e., crystalline form). As compared with the crystalline form, the neat amorphous form of Compound 1 (Form B) also exhibited higher $C_{max}$ (ng/mL) and $AUC_{0-inf}$, (ng·h/mL). However, the values of $C_{max}$ (ng/mL) and AUC0-inf (ng·h/mL) of Form B were lower than any of those of the amorphous solid dispersion solid. Therefore, the amorphous solid dispersion solid as MBP of the present application have significantly better relative bioavailability than the crystalline form and the neat amorphous form of Compound 1.

Example 15

Pharmacokinetic Comparison of Form A and Form F in Dogs

1. Drugs and Reagents:

Powder of Form A with particle sizes of D90=62.4 μm after micronization. The material content (purity) was not less than 98.0%.

Powder of Form B with particle sizes of D90=69.9 μm, D10=3.5 um, D50=1.4 um after micronization. The material content (purity) was not less than 98.0%.

Powder of Form F with particle sizes of D90<200 μm after micronization. The material content (purity) was not less than 98.0%.

2. Experiment Animals:

Beagle dogs, male and female, were used in this study.

3. Pharmaceutical Preparation:

An appropriate amount of each substance was weighed and was disperse in 0.5% sodium carboxymethyl cellulose. A suspension was prepared at the desired concentration of Compound 1 for each substance. All the doses and concentrations of Compound 1 were calculated with freebase in this study.

4. Administration and Sample Collection:

The dosing solutions were freshly prepared prior to dose administration. The actual body weights and actual volume injected were recorded accordingly. The dogs were fasted overnight and were allowed to intake food four hours after dosing. Each suspension was administrated orally to dogs at a dose ranged from 0.5 to 5 mg/kg. Blood samples (~1.0 mL) were collected at pre-dose and at different times up to 36 hours post-dosing via cephalic vein plexus. Whole blood was processed by centrifugation and plasma samples were collected and kept at freezer prior to analysis. Plasma samples were processed by protein precipitation. Concentrations of Compound 1 in the plasma samples were determined using a validated liquid chromatography-tandem mass spectrometry (LC-MS/MS) method. The plasma concentration-time data were analyzed using a non-compartmental model using Pharsight WinNonlin. The $C_{max}$ and area under the concentration-time curve for each compound is shown in Table 8.

TABLE 8

PK Profiles of Form A and Form F in Dogs

| Compound 1 | Form A | Form A | Form F (Cmp 1:LF = 1:4) |
|---|---|---|---|
| Dosage (mpk) | 0.5 (IV) | 5 (PO) | 5 (PO) |
| T½ (h) | 11 | 11 | 13 |
| $Vd_{ss}$ (L/kg) | 0.97 | | |
| CL(mL · kg$^{-1}$ · min$^{-1}$) | 1.22 | | |
| $C_{max}$(ng/mL) | | 1121 | 3738 |
| $AUC_{0-t}$(h · ng · mL$^{-1}$) | 6874 | 23367 | 63598 |
| F(%) | 100 | 34 | 92.5 |

The above experiment showed that the $C_{max}$ (ng/mL) and $AUC_{0-inf}$(ng·h/mL) of Compound 1 were dramatically improved in Form F (i.e., the amorphous solid dispersion as MBP) as compared with the crystalline form of Compound 1 (Form A). Therefore, Form F and its corresponding drug product have significantly better relative bioavailability than the crystalline form, suggesting the role of the amorphous solid dispersion of Compound 1 in the clinical use.

The foregoing examples and description of certain embodiments should be taken as illustrating, rather than as limiting the present invention as defined by the claims. As will be readily appreciated, numerous variations and combinations of the features set forth above can be utilized without departing from the present invention as set forth in the claims. All such variations are intended to be included within the scope of the present invention. All references cited are incorporated herein by reference in their entireties.

What is claimed is:

1. A stable amorphous solid dispersion comprising Compound 1 and a stabilizing polymer, wherein Compound 1 is 1-((1S,1aS,6bS)-5-((7-oxo-5,6,7,8-tetrahydro-1,8-naphthyridin-4-yl)oxy)-1a,6b-dihydro-1H-cyclopropa[b]benzofuran-1-yl)-3-(2,4,5-trifluorophenyl) urea, and Compound 1 is molecularly dispersed within a polymer matrix formed by the stabilizing polymer in its solid state, wherein the stabilizing polymer is hydroxypropyl methylcellulose acetate succinate, type LF (HPMCAS-LF), and the weight ratio of Compound 1 in the form of freebase and the polymer is 1:4, and wherein HPMCAS-LF has 5.0-9.0% of acetyl group and 14.0-18.0% of succinoyl group.

2. The stable amorphous solid dispersion according to claim 1, wherein the stable amorphous solid dispersion has a drug-loading content of Compound 1 ranging from 10% w/w to 40% w/w.

3. The stable amorphous solid dispersion according to claim 1, wherein the stable amorphous solid dispersion has a glass transition temperature ranging from 110-115° C.

4. The stable amorphous solid dispersion according to claim 1, wherein the stable amorphous solid dispersion is formulated into an orally administrated formulation.

* * * * *